United States Patent
Vacca

(10) Patent No.: US 10,654,852 B2
(45) Date of Patent: May 19, 2020

(54) ANTIBIOTICS AND METHODS OF USING SAME

(71) Applicant: THE BROAD INSTITUTE, INC., Cambridge, MA (US)

(72) Inventor: Joseph P. Vacca, Cambridge, MA (US)

(73) Assignee: THE BROAD INSTITUTE, INC., Cambridge, MA (US)

(*) Notice: Subject to any disclaimer, the term of this patent is extended or adjusted under 35 U.S.C. 154(b) by 0 days.

(21) Appl. No.: 16/342,903

(22) PCT Filed: Oct. 20, 2017

(86) PCT No.: PCT/US2017/057553
§ 371 (c)(1),
(2) Date: Apr. 17, 2019

(87) PCT Pub. No.: WO2018/075871
PCT Pub. Date: Apr. 26, 2018

(65) Prior Publication Data
US 2019/0240203 A1    Aug. 8, 2019

Related U.S. Application Data

(60) Provisional application No. 62/411,384, filed on Oct. 21, 2016.

(51) Int. Cl.
| | | |
|---|---|---|
| *A61K 31/439* | (2006.01) | |
| *C07D 471/08* | (2006.01) | |
| *A61K 31/4427* | (2006.01) | |
| *A61P 31/04* | (2006.01) | |

(52) U.S. Cl.
CPC .......... *C07D 471/08* (2013.01); *A61K 31/439* (2013.01); *A61K 31/4427* (2013.01); *A61P 31/04* (2018.01)

(58) Field of Classification Search
CPC .. C07D 471/00; C07D 471/08; A61K 31/439; A61P 31/04
See application file for complete search history.

(56) References Cited

U.S. PATENT DOCUMENTS

2015/0368196 A1   12/2015   Kolocouris et al.

OTHER PUBLICATIONS

"Syphilis-prevention", http://www.webmd.com/sexual-conditions/tc/syphilis-prevention?print=true,accessed Apr. 9, 2010, last updated Oct. 2, 2007 (Year: 2010).*
Eibl. Bioorganic and Medicinal Chemistry, 2013, 21(23), 7283-7308 (Year: 2013).*
Eibl et al., "The 3,7-diazabicyclo[3.3.1]nonane scaffold for subtype selective nicotinic acetylcholine receptor (nAChR) ligands: Part 1, The Influence of different hrydrogen bond acceptor systems on alkyl and (hetero)aryl substituents," BIoorg Med. Chem. vol. 21(23), pp. 7283-7308 (2013).
Smissman et al., "7-Aza Analogs of the Analgetic Agent Azabicyclane, Synthesis and Pharmacologic Analysis," J. Med. Chem., vol. 19(1), pp. 184-196 (1976).
PubChem-CID-10449646, Create date: Oct. 25, 2006 (Oct. 25, 2006), p. 3, Fig.
International Search Report and Written Opinion for corresponding PCT Patent Application No. PCT/US17/57553, dated Jan. 12, 2018 (16 pages).

* cited by examiner

*Primary Examiner* — Noble E Jarrell
(74) *Attorney, Agent, or Firm* — Melissa Hunter-Ensor; Scott Goncher; Greenberg Traurig, LLP

(57) ABSTRACT

The present invention includes novel 3,6-diazabicyclo [3.1.1]heptane antibiotic compounds and any salts or solvates thereof. The present invention further includes methods of preparing such compounds, and methods of treating bacterial infection in a subject using such compounds.

9 Claims, 2 Drawing Sheets

ANTIBIOTICS AND METHODS OF USING SAME

CROSS-REFERENCE TO RELATED APPLICATIONS

This application is the U.S. national phase application, pursuant to 35 U.S.C. § 371, of PCT International Application Ser. No.: PCT/US2017/057553, filed Oct. 20, 2017, designating the United States and published in English, which claims the benefit of and priority to U.S. Provisional Patent Application Ser. No. 62/411,384, filed Oct. 21, 2016, which is incorporated herein by reference in its entirety.

BACKGROUND OF THE INVENTION

The repeated use of the same antibiotics has led to increased bacterial resistance to known methods of treatment. As a result of these increases in resistance, some bacterial infections have become difficult to treat with known antibiotics or have become untreatable. New techniques are being developed in order to cause bacterial cell apoptosis, or prevent bacterial cell proliferation in strains of bacteria that have already developed a resistance to conventional antibiotics. For example, some methods of treatment involve the disruption of various mechanisms pertinent to bacterial cell growth or survival. One such mechanism is induced by type II topoisomerases.

Type II topoisomerases are ATP-consuming enzymes that cut both strands of a DNA helix simultaneously in order to manage DNA tangles and supercoils. Once cut, the ends of the DNA are separated, and a second DNA duplex is passed through the break of the separated DNA strand. Following passage, the cut DNA is religated. This reaction allows type II topoisomerases to increase or decrease the linking number of a DNA loop by two units, and it promotes chromosome disentanglement which is necessary for cell survival if other enzymes are to transcribe the sequences that encode proteins, or if the chromosomes are to be replicated.

Disruption of the essential mechanism of such topoisomerases leads to cell death. For example, DNA gyrase, a type II topoisomerase observed in *Escherichia coli* ("*E. coli*") and most other prokaryotes, introduces negative supercoils and decreases the linking number of DNA strands by 2 and is further able to remove knots from the bacterial chromosome thus providing necessary functions for *E. coli* cell growth. Some small molecules targeting type II topoisomerases are able to prevent or inhibit this mechanism induced by DNA gyrase and prevent the proliferation of bacterial cells.

Small molecules which target type II topoisomerase are divided into two classes: inhibitors and poisons. Inhibitors, such as mitindomide, work as non-competitive inhibitors of ATPase and prevent the separation of DNA induced by topoisomerases (i.e. decatenation activity). Poisons, which include etoposide, novobiocin, quinolones (including ciprofloxacin), and teniposide, target the DNA-protein complex in ways other than inhibition. Some poisons cause increased cleavage, whereas others, such as etoposide, inhibit religation of the DNA strands. Some fluoroquinolones selectively inhibit the topoisomerase II ligase domain, leaving the two nuclease domains intact. This modification, coupled with the constant action of the topoisomerase II in the bacterial cell, leads to DNA fragmentation via the nucleoside activity of the intact enzyme domains. Other fluoroquinolones are more selective for topoisomerase IV ligase domain, with enhanced Gram-positive activity. Some poisons of type II topoisomerases can target prokaryotic and eukaryotic enzymes preferentially. This may cause drug-resistant bacterial mutants to cluster around the active site for poisons leading to increasing amounts of strains resistant to the anti-bacterial medication.

There is a need in the art to develop novel antibiotics that are useful in treating or preventing bacterial infections in a subject in need thereof. The present invention meets this need.

SUMMARY OF THE INVENTION

As described below, the present invention generally features novel compounds with antibiotic activity, compositions comprising these compounds, and methods of treating bacterial infections using these compounds.

In one aspect, the invention provides a compound of formula (I):

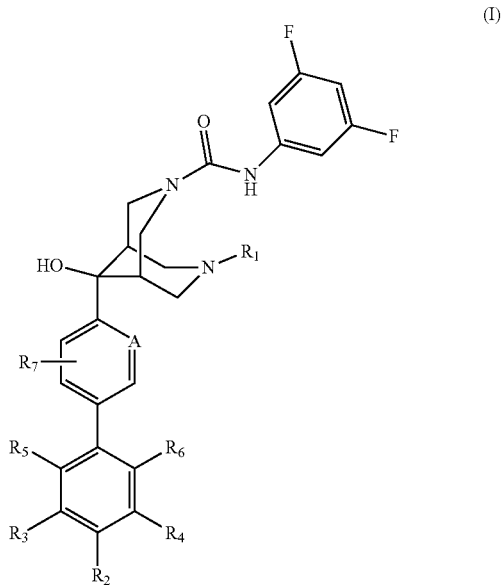

wherein A is N or $CR_7$;
$R_1$ is hydrogen or a $C_{1-5}$ alkyl hydrocarbon;
$R_7$ is independently hydrogen or fluorine at each occurrence; and
$R_2$-$R_6$ are independently selected at each occurrence from hydrogen, —X, -$L_1$-X, or -$L_1$-R;
where —X is independently selected at each occurrence from —CN, —$NH_2$ or —F;
$L_1$ is selected independently at each occurrence from —NH—, —N(R)—, —C(O)—, —$(CH_2)_{1-4}$—, —C(O)—N(R)—, —$(C(R)_2)_{1-3}$—N(R)—, or —$(C(R)_2)_{1-3}$—;
R is independently selected at each occurrence from hydrogen, or $C_{1-5}$ linear or branched alkyl;
wherein at least one of $R_2$-$R_4$ is a group -$L_1$-R;
or pharmaceutically acceptable salts thereof.

In another aspect, the invention provides a pharmaceutical composition comprising a pharmaceutically acceptable carrier and at least one compound of the invention.

In yet another aspect, the invention provides a method of treating or preventing a bacterial infection in a subject in need thereof, the method comprising administering to subject a pharmaceutical composition comprising at least one compound of formula (I), or a salt or solvate thereof. In some embodiments, the method comprises administering to a subject a therapeutically effective amount of a pharmaceutical composition comprising a compound of the invention. In some embodiments, the subject is a mammal (e.g., a human, a mouse, a rat, a primate, etc.). In some embodiments, the method is used to treat a bacterial infection caused by at least one strain of Gram-negative bacteria and/or Gram-positive bacteria. In some embodiments, the pharmaceutical composition is administered intravenously in the subject. In some embodiments, the method further comprises first determining the type of strain of bacteria which caused the bacterial infection before administering to the subject a therapeutically effective amount of an inventive compound.

In various embodiments of any of the above aspects or any other aspect of the invention delineated herein, the composition further comprises at least one additional antibacterial agent. In other embodiments, the subject is further administered at least one additional antibacterial agent. In yet other embodiments, the compound and the agent are coadministered to the subject. In yet other embodiments, the compound and the agent are coformulated. In yet other embodiments, the subject is a mammal. In yet other embodiments, the mammal is a human.

In various embodiments of any of the above aspects or any other aspect of the invention delineated herein, the antibacterial agent comprises at least one selected from the group consisting of amoxicillin, azithromycin, biaxin, biocef, cefaclor, cinoxacin, ciprofloxacin, clindamycin, doryx, emgel, enoxacin, fortaz, gatifloxacin, levofloxacin, linezolid, maxaquin, moxifloxacin, neomycin, ofloxacin, penicillin, rifampin, sparfloxacin, streptomycin, sulfatrim, tetracycline, trovafloxacin, vancomycin and zotrim. In other embodiments, the compound and the agent are coformulated in the composition.

In various embodiments of any of the above aspects or any other aspect of the invention delineated herein, the bacterial infection may be caused by at least one strain of Gram-negative bacteria. In other embodiments, the bacterial infection may be caused by at least one strain of Gram-positive bacteria. In yet other embodiments, the bacterial infection may be caused by at least one strain of Gram-negative bacteria and at least one strain of Gram-positive bacteria. In yet other embodiments, the compound may have bactericidal activity (i.e. kills bacterial cells) in the subject. In some embodiments, the compound may have bacteriostatic activity (i.e. prevents bacterial cell growth) in the subject. In some embodiments, the compound may have bactericidal and bacteriostatic activity in the subject.

The invention provides novel compounds with antibiotic activity, compositions comprising the same, and methods of treating bacterial infections. Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

DETAILED DESCRIPTION OF THE INVENTION

Figure 1:
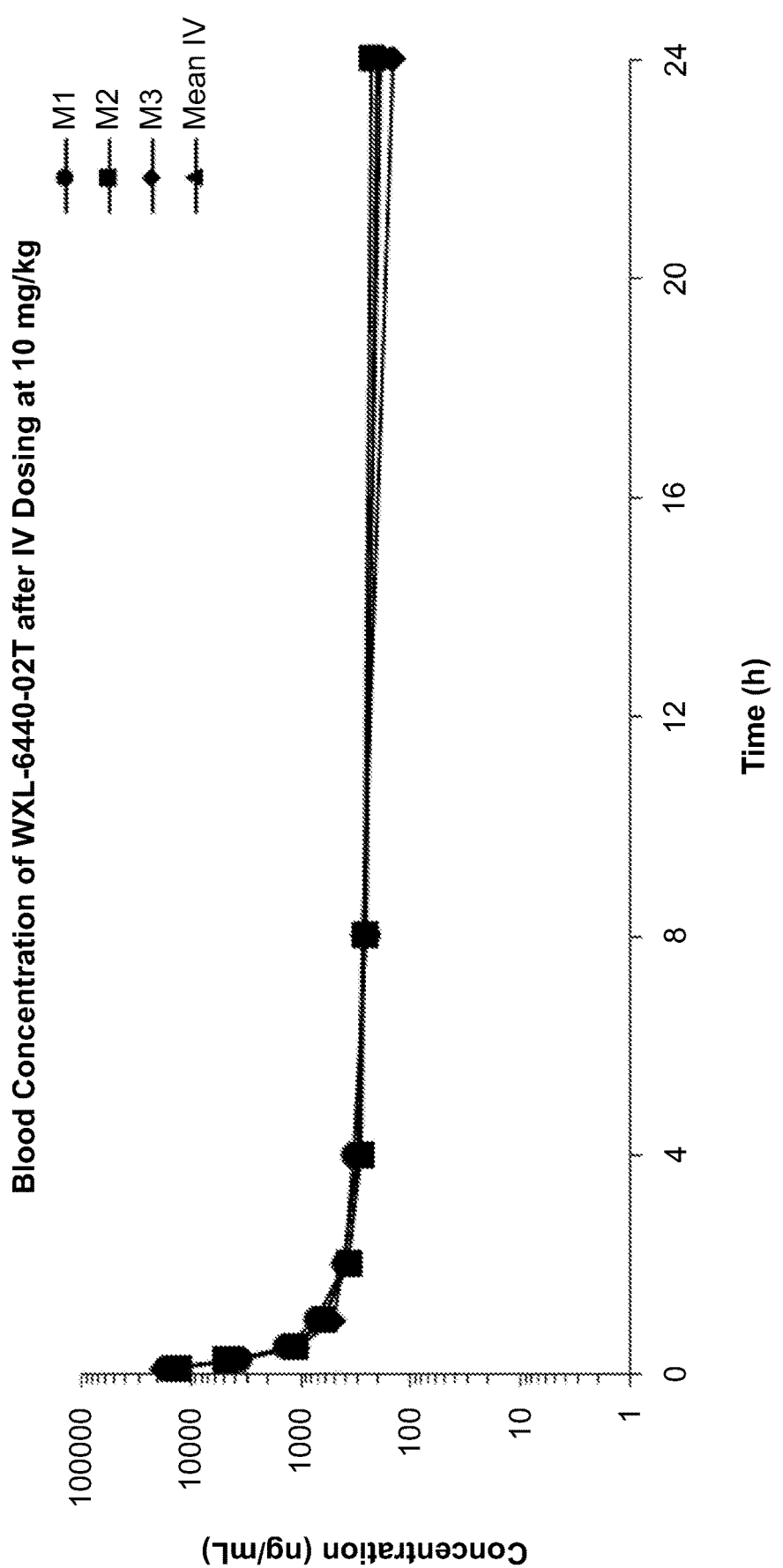
FIG. 1 is a plot representing the blood concentration of the specified agent in mice as a function of time after administration.

The present invention relates to the unexpected discovery of novel compounds with antibiotic activity, compositions comprising these compounds, and methods of treating bacterial infections using these compounds.

In one aspect, the invention provides novel bicyclic antibiotic compounds, comprising 3,7-diazabicyclo[3.3.1]nonane-3-carboxamides, and any salts or solvates thereof. In certain embodiments, the compounds of the invention have broad-spectrum antibiotic activity. In other embodiments, the compounds of the invention are active against one or more strains of Gram-negative bacteria and/or one or more strains of Gram-positive bacteria. In yet other embodiments, the compounds of the invention are bactericidal and/or bacteriostatic.

In certain embodiments, the compounds of the invention act by binding to bacterial gyrase. In other embodiments, the compounds of the invention inhibit the activity of bacterial gyrase. In yet other embodiments, the compounds of the invention are bactericidal. In yet other embodiments, resistance in Gram-negative bacteria against the compounds of the invention requires two or more mutations in at least two distinct Type IIa topoisomerases: gyrase and Topo IV. Without wishing to be limited by any theory, at least some compounds of the invention bind to and stabilize the non-covalent DNA-gyrase complex, thereby preventing DNA cleavage by the gyrase. Without wishing to be bound by theory, in certain embodiments, the compounds of the invention bind to the DNA-gyrase complex, wherein the $NR_1$ bicyclic nitrogen makes a hydrogen bond to the residue corresponding to the proton-donating residue Asp83 in the S. aureus gyrase (or Asp82 in the E. coli gyrase). In other embodiments, the compounds of the invention bind to the DNA-gyrase complex, wherein the $NR_1$ bicyclic nitrogen makes a hydrogen bond to a residue in each one of the four gyrase A proteins in the heterotetramer, wherein the residue in each gyrase A protein corresponds to Asp83 in the S. aureus gyrase (or Asp82 in the E. coli gyrase).

The compounds of the invention are useful to treat or prevent bacterial infections in a subject, such as but not limited to bacterial infections caused by Gram-negative bacteria. In certain embodiments, the compounds of the invention are bactericidal.

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "administration" means providing the composition of the present invention to a subject by any suitable method.

As used herein, the term "alkenyl" employed alone or in combination with other terms means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH$_2$—CH=CH$_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$-C$_3$) alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., C$_1$-C$_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is (C$_1$-C$_6$) alkyl, such as, but not limited to, ethyl, methyl, isopropyl, isobutyl, n-pentyl, n-hexyl and cyclopropylmethyl.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl" or "arene" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl (including 1- and 2-naphthyl). Preferred are phenyl and naphthyl, most preferred is phenyl.

As used herein, the term "aryl-(C$_1$-C$_3$) alkyl" means a functional group wherein a one to three carbon alkylene chain is attached to an aryl group, e.g., —CH$_2$CH$_2$-phenyl or —CH$_2$-phenyl (benzyl). Preferred is aryl-CH$_2$— and aryl-CH(CH$_3$)—. The term "substituted aryl-(C$_1$-C$_3$)alkyl" means an aryl-(C$_1$-C$_3$) alkyl functional group in which the aryl group is substituted. Preferred is substituted aryl (CH$_2$)—. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. Preferred is heteroaryl-(CH$_2$)—. The term "substituted heteroaryl-(C$_1$-C$_3$)alkyl" means a heteroaryl-(C$_1$-C$_3$)alkyl functional group in which the heteroaryl group is substituted. Preferred is substituted heteroaryl-(CH$_2$)—.

In one aspect, the terms "co-administered" and "co-administration" as relating to a subject refer to administering to the subject a composition of the invention, or salt thereof, along with a composition that may also treat any of the diseases contemplated within the invention. In one embodiment, the co-administered compositions are administered separately, or in any kind of combination as part of a single therapeutic approach. The co-administered composition may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier or excipient. The pharmaceutical composition facilitates administration of the compound to a subject.

As used herein, "concentration" of a reaction refers to increasing the concentration of one or more components in a reaction mixture.

As used herein, the term "δ" refers to chemical shifts in an NMR. Unless otherwise indicated, any numerical δ values are expressed in ppm.

As used herein, the term "DCM" refers to dichloromethane.

By "disease" or "disorder" is meant any condition (such as, but not limited to, infection and/or colonization by microorganisms, or physical and/or functional damage associated with same) that damages or interferes with the normal function of a cell, tissue, or organ. In certain embodiments, the disease comprises bacterial infection in a subject. Non-limiting examples of infectious bacteria contemplated within the invention include, but are not limited to, those listed in Table 1.

TABLE 1

| Species | Strain ID | Phenotype |
|---|---|---|
| *Acinetobacter baumannii* | | OXA-40, OXA-119 |
| *Enterobacter cloacae* | | Chromosomal AmpC |
| *Escherichia coli* | ATCC 25922 | |
| *Escherichia coli* (ΔtolC *E. coli*) | ATCC 25922 | ΔtolC |
| *Escherichia coli* | ATCC 35218 | TEM-1 |
| *Haemophilus influenzae* | ATCC 49247 | |
| *Klebsiella pneumoniae* | ATCC 700603 | SHV-18, OXO-2 |
| *Klebsiella pneumoniae* | | |
| *Pseudomonas aeruginosa* | PAO1 | |
| *Pseudomonas aeruginosa* (Δmex PAO1) | PAO1 | ΔmexABCDXY |
| *Enterococcus faecalis* | ATCC 29212 | |
| *Staphylococcus aureus* | ATCC 29213 | |
| *Staphylococcus aureus* | | MRSA, FQ$^R$ |
| *Staphylococcus aureus* | USA 100 | MRSA |
| *Streptococcus pneumoniae* | ATCC 49619 | |
| *Streptococcus pyogenes* | | |

As used herein, the term "DMSO" refers to dimethylsulfoxide.

By "effective amount" is meant the amount of a compound that is required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" or a "therapeutically effective" amount. An effective amount may be given by administration of an active ingredient to a subject once or more than once (e.g., two times, three times, ten times, twenty times, etc.). An effective amount may be administered to a subject at regular intervals (daily, weekly, bi-monthly, monthly, etc.).

As used herein, the term "EtOAc" refers to ethyl acetate.

As used herein, the term "Gram-negative" and "Gram-positive" in relation to bacteria refers to bacteria which do not or do retain the stain when using a triarylmethane dye (e.g. crystal violet or gentian violet) in the Gram staining of bacteria, respectively. Typically, a Gram stain differentiates bacteria by the chemical and physical properties of their cell walls and indicates the presence of peptidoglycan in the cell wall in Gram-positive bacteria. However, some bacteria cannot be classified as Gram-negative and Gram-positive. These bacteria are designated as "Gram-variable" or "Gram-indeterminate," both of which may also be affected by the compounds of the invention.

As used herein, the term "halo" or "halogen" employed alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S (=O)—CH$_3$. Up to two heteroatoms may be consecutive, such as, for example, —CH$_2$—NH—OCH$_3$, or —CH$_2$—CH$_2$—S—S—CH$_3$.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The phrase "individual in need thereof" denotes a subject or individual with an infection. In some embodiments, the individual in need thereof is a patient that has been diagnosed with an infection caused by one or more strains of bacteria. The term "prevent," as used herein, includes delaying the onset of a progression of a disease or physiological manifestation of disease. The term "treat" includes reducing, diminishing, eliminating, ameliorating, forestalling, and slowing the progression of, and/or delaying the onset of a given disease or physiological manifestation thereof.

As used herein, the term "instructional material" includes a publication, a recording, a diagram, or any other medium of expression that may be used to communicate the usefulness of the compositions and methods of the invention. In some instances, the instructional material may be part of a kit useful for treating a bacterial infection in a subject. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this invention.

As used herein, the term "MIC" refers to minimum inhibitory concentrations. Minimum inhibitory concentrations may be determined by broth microdilution according to the Clinical and Laboratory Standards Institute guidelines (see, e.g., *M07-A8. Methods for dilution antimicrobial susceptibility tests for bacteria that grow aerobically: approved standard*, 8$^{th}$ Ed.; Clinical and Laboratory Standards Institute, Vol. 26, No. 2). One example for measuring minimum inhibitory concentrations may be found in Reck et al., 2012, J. Med. Chem. 55:6916-6933, the disclosure of which is incorporated by reference. Inoculants may be incubated on blood agar plates for 18 to 24 hours. Incubation may occur at a temperature from about 35° C. to about 37° C. Compounds may be dissolved in 100% DMSO and diluted to 2% DMSO (v/v) in culture medium to 11 doubling dilutions from 64 to 0.06 µg/ml. In serum supplemented experiments, the testing medium (e.g., DMSO solution) and human serum may be mixed. The ratio of testing medium to human serum may be 1:1 (vol:vol). Plates may be read by spectrophotometry at 620 nm. Unless indicated otherwise, all inhibitory concentrations recited in the specification relate to MICs.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition, and disorder are used interchangeably herein.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "salt" refers to a salt of a compound contemplated within the invention, including inorganic acids, organic acids, inorganic bases, organic bases, solvates, hydrates, or clathrates thereof. As used herein, the term "salt" embraces addition salts of free acids or free bases that are compounds useful within the invention. Suitable acid addition salts may be prepared from an inorganic acid or an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy-ethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzyl-ethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "subject," "patient" or "individual" may be a human or non-human mammal or a bird. Non-human mammals include, for example, livestock and pets, such as ovine, bovine, equine, porcine, canine, feline and murine mammals. Preferably, the subject is human.

As used herein, the term "substituted" means that an atom or group of atoms has replaced hydrogen or the specified atom as the substituent attached to another group. Substitution of may occur along positions of a hydrocarbon chain. Unless stated otherwise, any group recited within the invention may be substituted. In some embodiments, any hydrocarbon or substituted hydrocarbon disclosed herein may be substituted with one or more substituents X, where X is independently selected at each occurrence from one or more (e.g., 1-20) heteroatoms or one or more (e.g., 1-10) heteroatom-containing groups, where, for example, X may be selected from —F; —Cl; —Br; —I; —OH, —OR*; —O—NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)(—N(R*)$_2$); —C(H)(=N—OH); —SH; —SR*; —S—, —S(=O)—, —CN; —NC; —C(=O)—R*; —CHO; —CO$_2$H; —CO$_2^-$; —CO$_2$; —CO$_2$R*; —C(=O)—R*, —C(=O)—S—R*; —O—(C=O)—H; —O—(C=O)—R*; —S—C(=O)—R*; —(C=O)—NH$_2$; —C(=O)—N(R*)$_2$; —C(=O)—NHNH$_2$; —O—C(=O)—NHNH$_2$; —C(=S)—NH$_2$; —(C=S)—N(R*)$_2$; —N(R*)—CHO; —N(R*)—C(=O)—R*; —C(=NR)—O—R*; —O—C(=NR*)—R*, —SCN; —NCS; —NSO; —SSR*; —N(R*)—C(=O)—N(R*)$_2$; —N(R*)—C(=S)—N(R*)$_2$; —S(=O)$_2$—R*; —O—S(=O)$_2$—R*; —S(=O)$_2$—OR*; —N(R*)—S(=O)$_2$—R*; —S(=O)$_2$—N(R*)$_2$; —O—SO$_3$—; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1-6}$CH$_3$; —PR*$_2$; —O—P(=O)(OR*)$_2$; and —P(=O)(OR*)$_2$, where, independently at each occurrence, R* may be H or a $C_{1-10}$ or $C_{1-8}$ or $C_{1-6}$ or $C_{1-4}$ hydrocarbon, including without limitation alkyl, alkenyl, alkynyl, aryl (e.g., phenyl), alkyl-aryl (e.g., benzyl), aryl-alkyl (e.g., toluyl), etc. In other embodiments, X may comprise a $C_1$-$C_8$ or $C_1$-$C_6$ or $C_2$-$C_4$ perfluoroalkyl. In other embodiments, X may a $C_1$-$C_8$ or $C_2$-$C_6$ or $C_3$-$C_5$ heterocycle (e.g., heteroaryl radical). The term "halo" or "halogen" refers to any radical of fluorine, chlorine, bromine or iodine. In some embodiments, X is independently selected at each occurrence from —OH, —O— SH, —NH$_2$; N(R*)$_2$; —F, —Cl, or —Br.

For aryl, aryl-($C_1$-$C_3$)-alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halogen, amino, acetamido and nitro. As used herein, where a substituent is an alkyl or alkoxy group, the carbon chain may be branched, straight or cyclic, with straight being preferred.

As used herein, the term "THF" refers to tetrahydrofuran.

The terms "treat" and "treating" and "treatment," as used herein, means reducing the frequency or severity with which symptoms of a disease or condition are experienced by a subject by virtue of administering an agent or compound to the subject.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

In one aspect, the invention provides novel antibiotic compounds. In certain embodiments, the compounds comprise a bicyclic 3,6-diazabicyclo[3.1.1]heptane. In other embodiments, the compounds of the invention have broad spectrum antibiotic activity. In yet other embodiments, the compounds of the invention inhibit one or more strains of Gram-negative bacteria. In yet other embodiments, the compounds of the invention are bactericidal.

In some embodiments of the invention, the compound for treating or preventing bacterial infections may have the structure of formula (I), or pharmaceutically acceptable salts thereof:

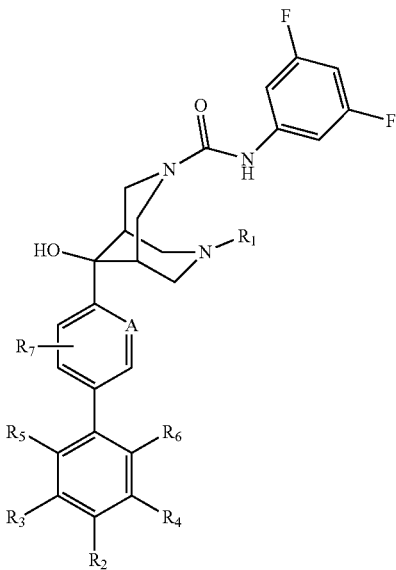

(I)

wherein A is N or CR$_7$;
R$_1$ is hydrogen or R;
R$_7$ is independently hydrogen, —X, or R; and
R$_2$-R$_6$ are independently selected at each occurrence from hydrogen, —X, L$_1$-X, or -L$_1$-R; where —X is independently selected at each occurrence from X is independently selected at each occurrence from the group consisting of —F; —Cl; —Br; —I; —OH; —OR*; —NH$_2$; —NHR*; —N(R*)$_2$; —N(R*)$_3$$^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)(—N(R*)$_2$); —C(H)(=N—OH); —SH; —SR*; —CN; —NC; —CCl$_3$, —CF$_2$Cl, —CFCl$_2$—C(=O)—R*; —CHO; —CO$_2$H; —CO$_2$$^-$; —CO$_2$R*; —C(=O)—S—R*; —O—(C=O)—H; —O—(C=O)—R*; —S—C(=O)—R*; —(C=O)—NH$_2$, —C(=O)—N(R*)$_2$; —C(=O)—NHNH$_2$; —O—C(=O)—NHNH$_2$; —C(=S)—NH$_2$; —(C=S)—N(R*)$_2$; —N(R*)—CHO; —N(R*)—C(=O)—R*; —C(=NR*)—O—R*; —O—C(=NR*)—R*; —SCN; —NCS; —NSO; —SSR*; —N(R*)—C(=O)—N(R*)$_2$; —N(R*)—C(=S)—N(R*)$_2$; —S(=O)$_{1-2}$—R*; —O—S(=O)$_2$—R*; —S(=O)$_2$—OR*; —N(R*)—S(=O)$_2$—R*; —S(=O)$_2$—N(R*)$_2$; —O—SO$_3$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1-6}$CH$_3$; —PR*$_2$; —O—P(=O)(OR*)$_2$; and —P(=O)(OR*)$_2$;

L$_1$ is a bivalent radical selected independently at each occurrence from —O—, —S—, —NH—, —N(R$^N$)—, —(CH$_2$)$_{1-4}$—, —(C(R)$_2$)$_{1-4}$—, —C=C—, —C≡C—, —(CH$_2$)$_{1-3}$—, —C(O)—, —(C$_2$)$_{1-3}$—C(O)—, —C(O)—(CH$_2$)$_{1-3}$—, —C(O)—O—(CH$_2$)$_{1-3}$—, —C(O)—N(R$^N$)—, —N(R$^N$)—C(O)—, —C(O)—N(R$^N$)—(CH$_2$)$_{1-3}$—, —(C(R)$_2$)$_{1-3}$—N(R)—, —(CH$_2$)$_{1-3}$—C(O)—N(R$^N$)—, —(CH$_2$)$_{0-3}$—NH—C(O)—, —(CH$_2$)$_{0-3}$—NH—C(O)—O—, —NH—S(O)$_{1-2}$—, —N(R$^N$)—S(O)$_{1-2}$—, —S—(CH$_2$)$_{1-3}$—, —NH—(CH$_2$)$_{1-3}$—, —N(R$^N$)—(CH$_2$)$_{1-3}$—, or —(OCH$_2$CH$_2$)$_{1-3}$—; and R is independently selected at each occurrence from hydrogen, or $C_{1-12}$ linear or branched alkyl. In some embodiments at least one of $R_2$-$R_4$ is a group -$L_1$-R. In some embodiments, R is selected from hydrogen or $C_{1-5}$ alkyl. In some embodiments, R is selected from hydrogen or $C_{1-3}$ linear or branched alkyl. In some embodiments R is hydrogen, methyl, or ethyl. In some embodiments, —X is independently selected at each occurrence from —CN, —NH$_2$ or —F. In some embodiments, $L_1$ is selected independently at each occurrence from —NH—, —N(R)—, —C(O)—, —(CH$_2$)$_{1-4}$—, —C(O)—N(R)—, —(C(R)$_2$)$_{1-3}$—N(R)—, or —(C(R)$_2$)$_{1-3}$—. In some embodiments, only one of $R_2$-$R_6$ is -$L_1$-R or -$L_1$-X. In some embodiments, $R_1$ is hydrogen or methyl. In some embodiments, $R_2$ is -$L_1$-R or -$L_1$-X. In some embodiments, $R_3$ or $R_4$ is -$L_1$-R or -$L_1$-X. In some embodiments, —X is NH$_2$ or —N(R)$_2$. In some embodiments, $R_3$-$R_6$ are independently selected at each occurrence from hydrogen, —CN, and —F. Non-limiting examples of compounds contemplated within the invention are illustrated below in Table 2. In some embodiments, the compound is selected from the group consisting of compound number 1-24.

TABLE 2

| Compound Number | Compound Name | Compound Structure |
| --- | --- | --- |
| 1 | (1R,5S,9r)-9-(4'-(aminomethyl)-2',3'-difluoro-[1,1'-biphenyl]-4-yl)-N-(3,5 difluorophenyl)-9-hydroxy-3,7-diazabicyclo[3.3.1]nonane-3-carboxamide | 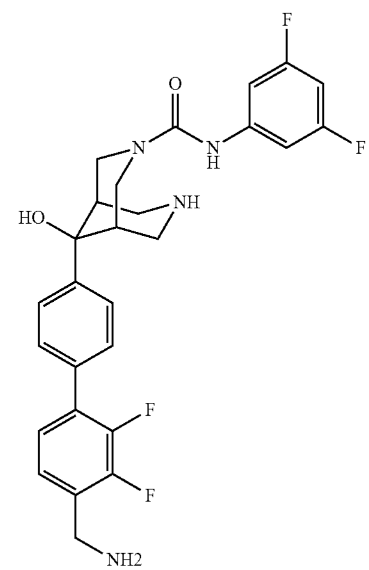 [SMILES: NCc1ccc(-c2ccc(C3(O)C4CNCC3CN(C(=O)Nc3cc(F)cc(F)c3)C4)cc2)c(F)c1F] |
| 2 | (1R,5S,9r)-9-(4'-(aminomethyl)-2',3'-difluoro-[1,1'-biphenyl]-4-yl)-N-(3,5-difluorophenyl)-9-hydroxy-7-methyl-3,7-diazabicyclo[3.3.1]nonane-3-carboxamide | 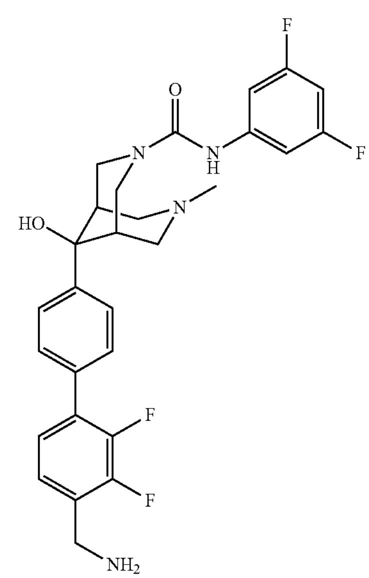 [SMILES: CN1CC2CN(C(=O)Nc3cc(F)cc(F)c3)CC(C1)C2(O)c1ccc(-c2ccc(CN)c(F)c2F)cc1] |

TABLE 2-continued
| Compound Number | Compound Name | Compound Structure |
|---|---|---|
| 3 | (1R,5S,9r)-9-(3'-(aminomethyl)-2'-fluoro-[1,1'-biphenyl]-4-yl)-N-(3,5-difluorophenyl)-9-hydroxy-7-methyl-3,7-diazabicyclo[3.3.1]nonane-3-carboxamide | 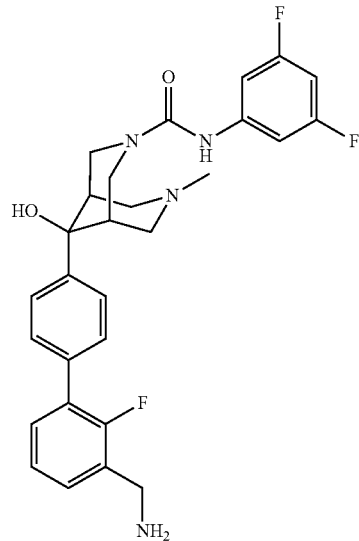 [SMILES: CN1CC2CN(C(=O)Nc3cc(F)cc(F)c3)CC(C1)C2(O)c1ccc(-c2cccc(CN)c2F)cc1] |
| 4 | (1R,5S,9r)-9-(5-(3-(aminomethyl)-2-fluorophenyl)pyridin-2-yl)-N-(3,5-difluorophenyl)-9-hydroxy-7-methyl-3,7-diazabicyclo[3.3.1]nonane-3-carboxamide | 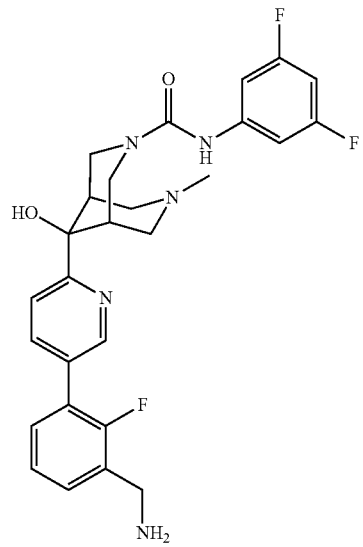 [SMILES: CN1CC2CN(C(=O)Nc3cc(F)cc(F)c3)CC(C1)C2(O)c1ccc(-c2cccc(CN)c2F)cn1] |

TABLE 2-continued
| Compound Number | Compound Name | Compound Structure |
|---|---|---|
| 5 | (1R,5S,9r)-9-(4'-(2-aminoethyl)-2',5'-difluoro-[1,1'-biphenyl]-4-yl)-N-(3,5-difluorophenyl)-9-hydroxy-7-methyl-3,7-diazabicyclo[3.3.1]nonane-3-carboxamide | 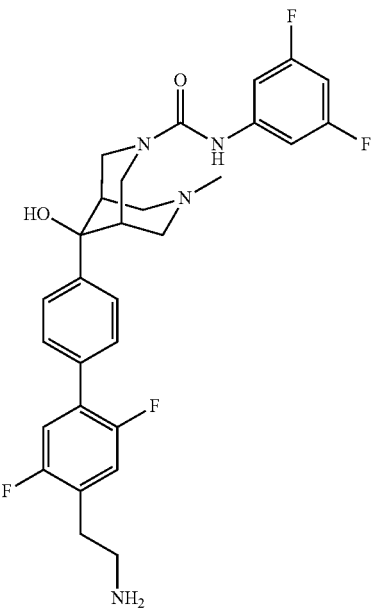 [SMILES: CN1CC2CN(C(=O)Nc3cc(F)cc(F)c3)CC(C1)C2(O)c1ccc(-c2cc(F)c(CCN)cc2F)cc1] |
| 6 | (1R,5S,9r)-9-(4'-(aminomethyl)-2,2'-difluoro-[1,1'-biphenyl]-4-yl)-N-(3,5-difluorophenyl)-9-hydroxy-3,7-diazabicyclo[3.3.1]nonane-3-carboxamide | 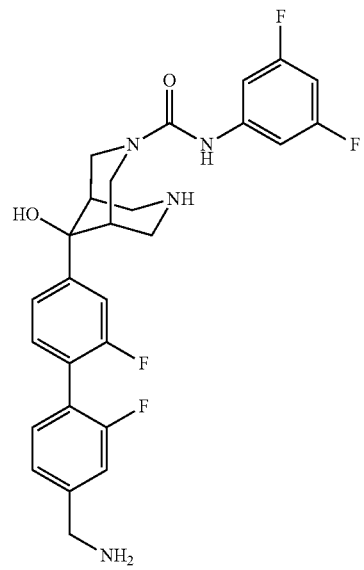 [SMILES: NCc1ccc(-c2ccc(C3(O)C4CNCC3CN(C(=O)Nc3cc(F)cc(F)c3)C4)cc2F)c(F)c1] |

TABLE 2-continued

| Compound Number | Compound Name | Compound Structure |
| --- | --- | --- |
| 7 | (1R,5S,9r)-9-(4'-(aminomethyl)-2'-cyano-2-fluoro-[1,1'-biphenyl]-4-yl)-N-(3,5-difluorophenyl)-9-hydroxy-3,7-diazabicyclo[3.3.1]nonane-3-carboxamide | 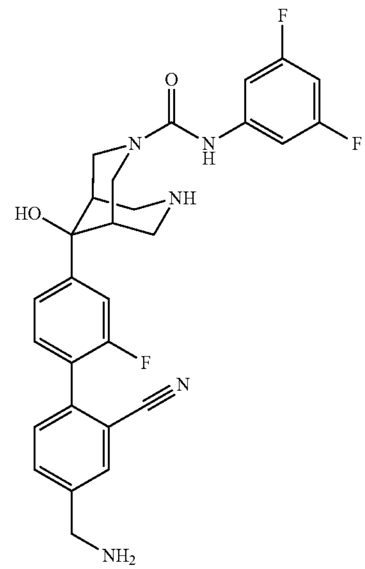 [SMILES: N#Cc1cc(CN)ccc1-c1ccc(C2(O)C3CNCC2CN(C(=O)Nc2cc(F)cc(F)c2)C3)cc1F] |
| 8 | (1R,5S,9s)-9-(4'-(aminomethyl)-2'-cyano-3-fluoro-[1,1'-biphenyl]-4-yl)-N-(3,5-difluorophenyl)-9-hydroxy-3,7-diazabicyclo[3.3.1]nonane-3-carboxamide | 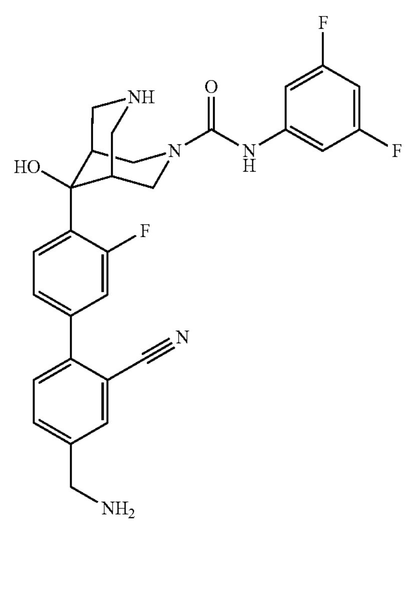 [SMILES: N#Cc1cc(CN)ccc1-c1ccc(C2(O)C3CNCC2CN(C(=O)Nc2cc(F)cc(F)c2)C3)c(F)c1] |

TABLE 2-continued

| Compound Number | Compound Name | Compound Structure |
|---|---|---|
| 9 | (1R,5S,9r)-9-(5-(4-((2-aminoethyl)carbamoyl)-2,5-difluorophenyl)pyridin-2-yl)-N-(3,5-difluorophenyl)-9-hydroxy-7-methyl-3,7-diazabicyclo[3.3.1]nonane-3-carboxamide | 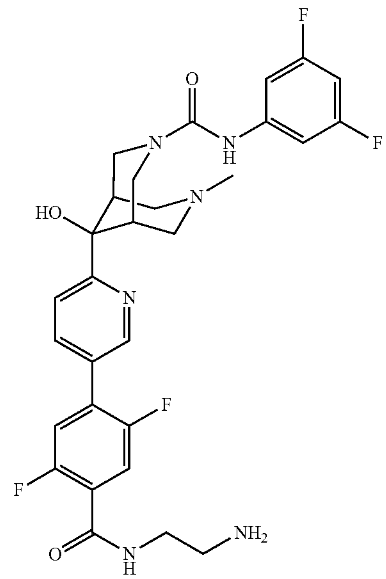 [SMILES: CN1CC2CN(C(=O)Nc3cc(F)cc(F)c3)CC(C1)C2(O)c1ccc(-c2cc(F)c(C(=O)NCCN)cc2F)cn1] |
| 10 | (1R,5S,9r)-9-(4'-((2-aminoethyl)carbamoyl)-2',5'-difluoro-[1,1'-biphenyl]-4-yl)-N-(3,5-difluorophenyl)-9-hydroxy-7-methyl-3,7-diazabicyclo[3.3.1]nonane-3-carboxamide | 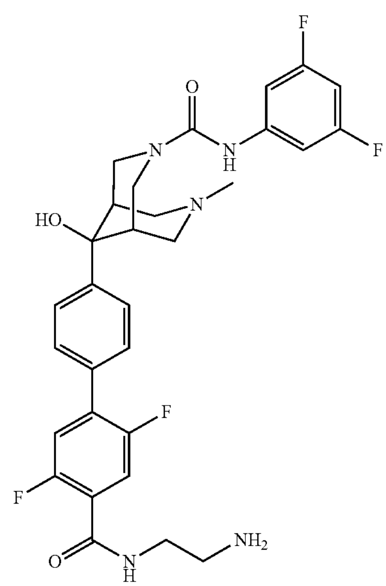 [SMILES: CN1CC2CN(C(=O)Nc3cc(F)cc(F)c3)CC(C1)C2(O)c1ccc(-c2cc(F)c(C(=O)NCCN)cc2F)cc1] |

TABLE 2-continued
| Compound Number | Compound Name | Compound Structure |
|---|---|---|
| 11 | (1R,5S,9r)-9-(4'-(aminomethyl)-2',6'-difluoro-[1,1'-biphenyl]-4-yl)-N-(3,5-difluorophenyl)-9-hydroxy-3,7-diazabicyclo[3.3.1]nonane-3-carboxamide | 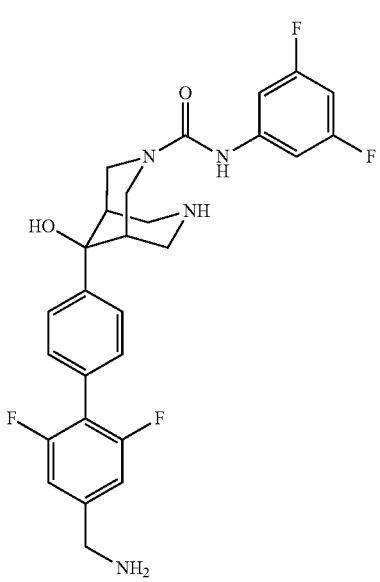 [SMILES: NCc1cc(F)c(-c2ccc(C3(O)C4CNCC3CN(C(=O)Nc3cc(F)cc(F)c3)C4)cc2)c(F)c1] |
| 12 | (1R,5S,9r)-9-(4'-(aminomethyl)-2'-fluoro-[1,1'-biphenyl]-4-yl)-N-(3,5-difluorophenyl)-9-hydroxy-7-methyl-3,7-diazabicyclo[3.3.1]nonane-3-carboxamide | 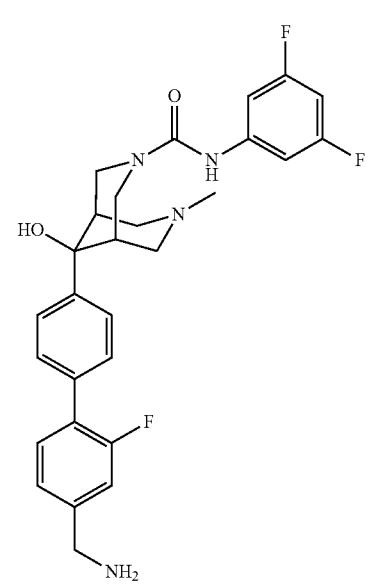 [SMILES: CN1CC2CN(C(=O)Nc3cc(F)cc(F)c3)CC(C1)C2(O)c1ccc(-c2ccc(CN)cc2F)cc1] |

TABLE 2-continued

| Compound Number | Compound Name | Compound Structure |
|---|---|---|
| 13 | (1R,5S,9r)-9-(5-(4-(aminomethyl)-2-fluorophenyl)-pyridin-2-yl)-N-(3,5-difluorophenyl)-9-hydroxy-7-methyl-3,7-diazabicyclo[3.3.1]nonane-3-carboxamide | 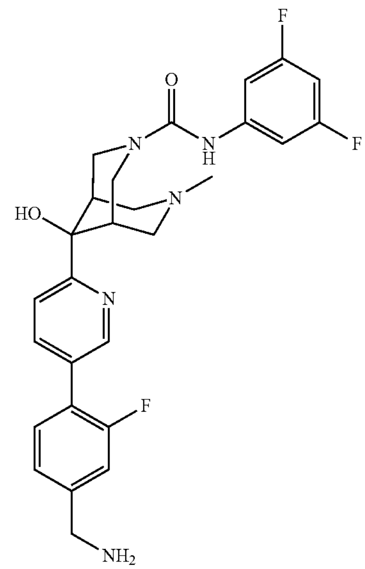 [SMILES: CN1CC2CN(C(=O)Nc3cc(F)cc(F)c3)CC(C1)C2(O)c1ccc(-c2ccc(CN)cc2F)cn1] |
| 14 | (1R,5S,9r)-N-(3,5-difluorophenyl)-9-(5-(2-fluoro-4-((methylamino)methyl)phenyl)pyridin-2-yl)-9-hydroxy-7-methyl-3,7-diazabicyclo[3.3.1]nonane-3-carboxamide | 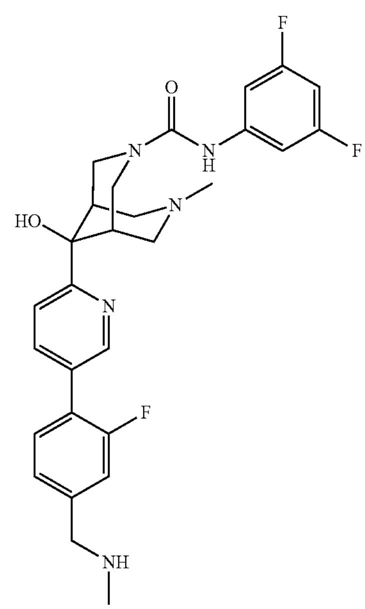 [SMILES: CNCc1ccc(-c2ccc(C3(O)C4CN(C)CC3CN(C(=O)Nc3cc(F)cc(F)c3)C4)nc2)c(F)c1] |

TABLE 2-continued
| Compound Number | Compound Name | Compound Structure |
|---|---|---|
| 15 | (1R,5S,9r)-N-(3,5-difluorophenyl)-9-(2'-fluoro-4'-((methylamino)methyl)-[1,1'-biphenyl]-4-yl)-9-hydroxy-7-methyl-3,7-diazabicyclo[3.3.1]nonane-3-carboxamide | 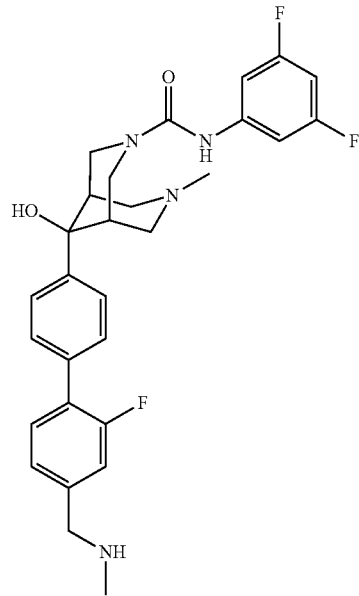 [SMILES: CNCc1ccc(-c2ccc(C3(O)C4CN(C)CC3CN(C(=O)Nc3cc(F)cc(F)c3)C4)cc2)c(F)c1] |
| 16 | (1R,5S,9r)-N-(3,5-difluorophenyl)-9-(5-(3-fluoro-4-((methylamino)methyl)phenyl)pyridin-2-yl)-9-hydroxy-7-methyl-3,7-diazabicyclo[3.3.1]nonane-3-carboxamide | 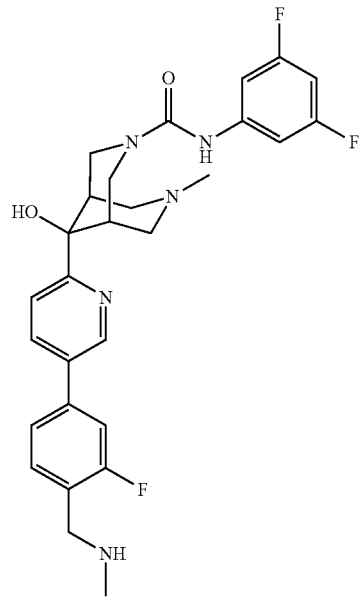 [SMILES: CNCc1ccc(-c2ccc(C3(O)C4CN(C)CC3CN(C(=O)Nc3cc(F)cc(F)c3)C4)nc2)cc1F] |

TABLE 2-continued

| Compound Number | Compound Name | Compound Structure |
|---|---|---|
| 17 | (1R,5S,9r)-9-(5-(2-cyano-4-((methylamino)methyl)phenyl)pyridin-2-yl)-N-(3,5-difluorophenyl)-9-hydroxy-7-methyl-3,7-diazabicyclo[3.3.1]nonane-3-carboxamide | 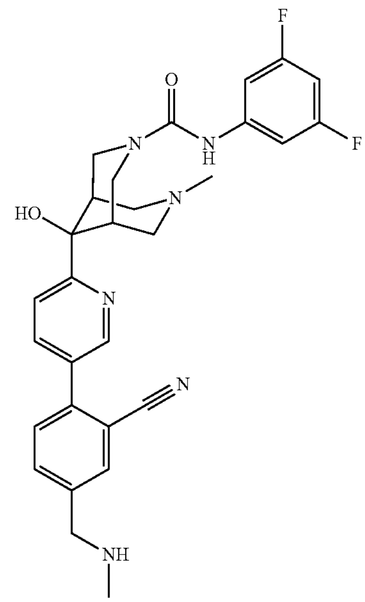 [SMILES: CNCc1ccc(-c2ccc(C3(O)C4CN(C)CC3CN(C(=O)Nc3cc(F)cc(F)c3)C4)nc2)c(C#N)c1] |
| 18 | (1R,5S,9r)-9-(2'-cyano-4'-((dimethylamino)methyl)-[1,1'-biphenyl]-4-yl)-N-(3,5-difluorophenyl)-9-hydroxy-7-methyl-3,7-diazabicyclo[3.3.1]nonane-3-carboxamide | 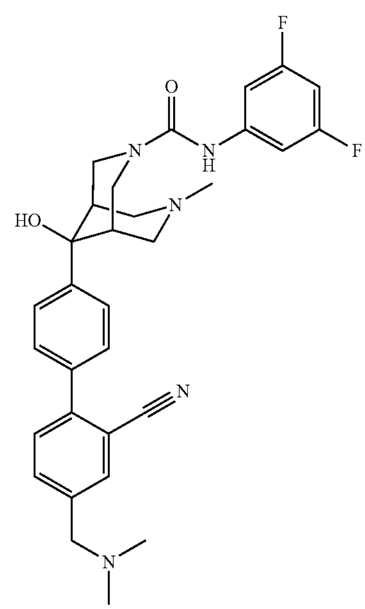 [SMILES: CN(C)Cc1ccc(-c2ccc(C3(O)C4CN(C)CC3CN(C(=O)Nc3cc(F)cc(F)c3)C4)cc2)c(C#N)c1] |

TABLE 2-continued

| Compound Number | Compound Name | Compound Structure |
|---|---|---|
| 19 | (1R,5S,9r)-9-(5-(4-(aminomethyl)-3-fluorophenyl)pyridin-2-yl)-N-(3,5-difluorophenyl)-9-hydroxy-7-methyl-3,7-diazabicyclo[3.3.1]nonane-3-carboxamide | 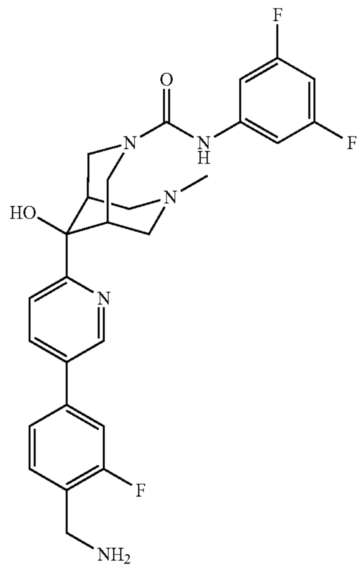 [SMILES: CN1CC2CN(C(=O)Nc3cc(F)cc(F)c3)CC(C1)C2(O)c1ccc(-c2ccc(CN)c(F)c2)cn1] |
| 20 | (1R,5S,9r)-9-(4'-(aminomethyl)-3'-fluoro-[1,1'-biphenyl]-4-yl)-N-(3,5-difluorophenyl)-9-hydroxy-7-methyl-3,7-diazabicyclo[3.3.1]nonane-3-carboxamide | 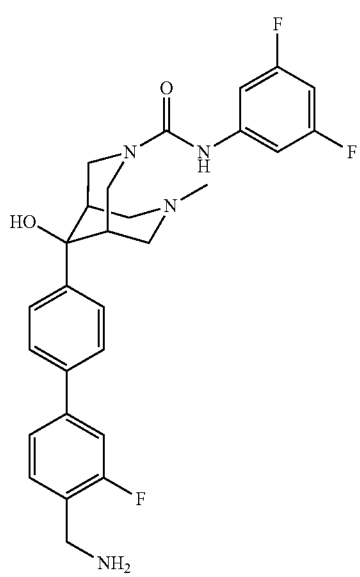 [SMILES: CN1CC2CN(C(=O)Nc3cc(F)cc(F)c3)CC(C1)C2(O)c1ccc(-c2ccc(CN)c(F)c2)cc1] |

TABLE 2-continued

| Compound Number | Compound Name | Compound Structure |
|---|---|---|
| 21 | (1R,5S,9r)-9-(5-(4-(aminomethyl)-2-cyano-6-fluorophenyl)pyridin-2-yl)-N-(3,5-difluorophenyl)-9-hydroxy-3,7-diazabicyclo[3.3.1]nonane-3-carboxamide | 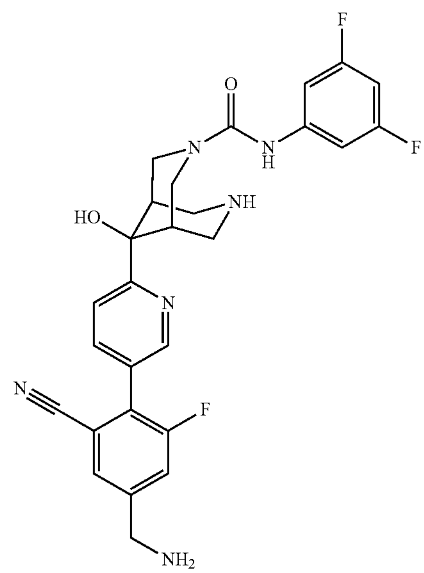 [SMILES: N#Cc1cc(CN)cc(F)c1-c1ccc(C2(O)C3CNCC2CN(C(=O)Nc2cc(F)cc(F)c2)C3)nc1] |
| 22 | (1R,5S,9r)-9-(4'-(aminomethyl)-2'-cyano-6'-fluoro-[1,1'-biphenyl]-4-yl)-N-(3,5-difluorophenyl)-9-hydroxy-3,7-diazabicyclo[3.3.1]nonane-3-carboxamide | 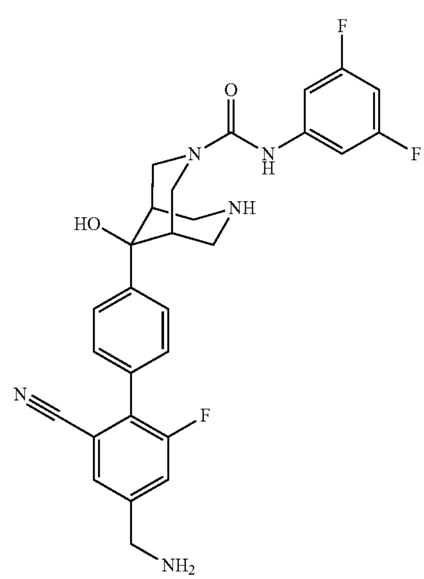 [SMILES: N#Cc1cc(CN)cc(F)c1-c1ccc(C2(O)C3CNCC2CN(C(=O)Nc2cc(F)cc(F)c2)C3)cc1] |

TABLE 2-continued

| Compound Number | Compound Name | Compound Structure |
|---|---|---|
| 23 | (1R,5S,9r)-9-(4'-(aminomethyl)-2'-cyano-[1,1'-biphenyl]-4-yl)-N-(3,5-difluorophenyl)-9-hydroxy-7-methyl-3,7-diazabicyclo[3.3.1]nonane-3-carboxamide | 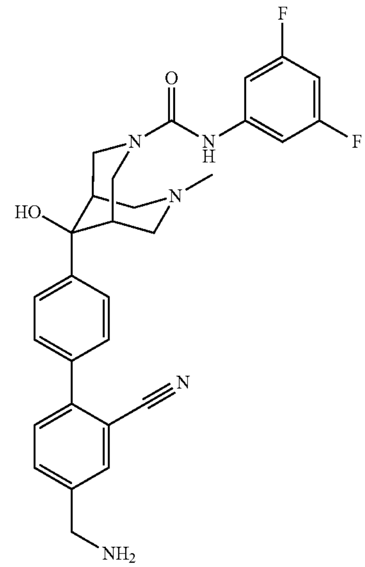 [SMILES: CN1CC2CN(C(=O)Nc3cc(F)cc(F)c3)CC(C1)C2(O)c1ccc(-c2ccc(CN)cc2C#N)cc1] |
| 24 | (1R,5S,9r)-9-(5-(4-(aminomethyl)-2-cyanophenyl)pyridin-2-yl)-N-(3,5-difluorophenyl)-9-hydroxy-7-methyl-3,7-diazabicyclo[3.3.1]nonane-3-carboxamide | 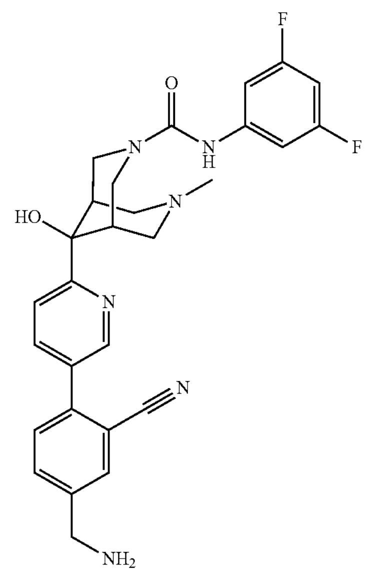 [SMILES: CN1CC2CN(C(=O)Nc3cc(F)cc(F)c3)CC(C1)C2(O)c1ccc(-c2ccc(CN)cc2C#N)cn1] |

It will be understood that in the event of any inconsistency between the compound name and the chemical structure in Table 2, all such compounds will be considered as embraced by the invention. For example, in the event of a discrepancy in the compound name and the structure provided, both the compound corresponding to the compound name and the compound corresponding to the structure will be considered within the scope of the invention.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds recited herein.

In one embodiment, compounds described herein are prepared as prodrugs. A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The invention further includes a pharmaceutical composition comprising the compound of the invention and a pharmaceutically acceptable carrier.

In certain embodiments, the pharmaceutical composition further comprises at least one additional agent that is useful to treat the diseases or disorders contemplated herein. In certain embodiments, the compound of the invention and the additional agent are co-formulated in the composition.

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

In certain embodiments, the compounds of the invention are useful in the methods of the invention in combination with at least one additional compound useful for treating or preventing a disease or disorder contemplated within the invention. In one particular embodiment, compounds of the invention are useful for treating or preventing a bacterial infection (e.g., Gram negative or Gram positive infection). This additional compound may comprise compounds identified herein or compounds, e.g., commercially available compounds, known to treat, prevent or reduce the symptoms of a bacterial infection.

In certain embodiments, at least one additional compound is an antibacterial agent. Non-limiting examples of antibacterial agents include, but are not limited to, amoxicillin, azithromycin, biaxin, biocef, cefaclor, cinoxacin, ciprofloxacin, clindamycin, doryx, emgel, enoxacin, fortaz, gatifloxacin, levofloxacin, linezolid, maxaquin, moxifloxacin, neomycin, ofloxacin, penicillin, rifampin, sparfloxacin, streptomycin, sulfatrim, tetracycline, trovafloxacin, vancomycin and zotrim.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In one aspect, the invention includes a method of treating or preventing bacterial infection in a subject in need thereof. In certain embodiments, the method comprises administering to the subject a therapeutically effective amount of a pharmaceutically acceptable composition comprising at least one compound of the invention. In other embodiments, the bacterial infection is caused by at least one strain of Gram-negative bacteria. In yet other embodiments, the bacterial infection is caused by at least one strain of Gram-positive bacteria. In yet other embodiments, the bacterial infection is caused by at least one strain of Gram-positive bacteria and at least one strain of Gram-positive bacteria.

In certain embodiments, the composition is administered to the subject by at least one route selected from oral, rectal, mucosal (e.g., by oral or nasal inhalation), transmucosal, topical (transdermal), or by intravenous, intradermal, intramuscular, subcutaneous, intracutaneous, intrauterine, epidural or intracerebroventricular injection. In other embodiments, the subject is further administered at least one additional compound useful for treating or preventing a bacterial infection. In yet other embodiments, the subject is a mammal. In yet other embodiments, the mammal is human. In yet other embodiments, the subject is not responsive to one or more commercially available and/useful antibiotics, such as but not limited to amoxicillin, azithromycin, biaxin, biocef, cefaclor, cinoxacin, ciprofloxacin, clindamycin, doryx, emgel, enoxacin, fortaz, gatifloxacin, levofloxacin, linezolid, maxaquin, moxifloxacin, neomycin, ofloxacin, penicillin, rifampin, sparfloxacin, streptomycin, sulfatrim, tetracycline, trovafloxacin, vancomycin and/or zotrim. The compositions of the present invention may be administered to a subject by various routes. All modes of administration are contemplated, for example, orally, rectally, mucosally (e.g., by oral or nasal inhalation), transmucosally, topically (i.e. transdermal), or by intravenous (i.e. intravenously), intradermal, intramuscular, subcutaneous, intracutaneous, intrauterine, epidural or intracerebroventricular injection.

The compositions of the present invention may contain a pharmaceutical acceptable carrier, excipient and/or diluent, and may be administered by a suitable method to a subject. The compositions of the present invention may be formulated in various forms, including oral dosage forms or sterile injectable solutions, according to any conventional method known in the art. In other embodiments, the compositions may also be used as an inhalation-type drug delivery system. In yet other embodiments, the compositions of the invention may be formulated for injectable solutions.

The compositions may be formulated as powders, granules, tablets, capsules, suspensions, emulsions, syrup, aerosol, preparations for external application, suppositories and sterile injectable solutions. Suitable formulations known in the art are disclosed in, for example, Remington's Pharmaceutical Science (Mack Publishing Company, Easton Pa.). Carriers, excipients and diluents that may be contained in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propyl hydroxylbenzoate, talc, magnesium stearate or mineral oil.

Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here. Capsule formulations may be of the hard gelatin or soft gelatin variety and can contain the active component in solid, semi-solid, or liquid form. Gelatin capsules can be formed from animal gelatin or synthetic or plant derived equivalents thereof. The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes. Instead of, or in addition to, a coating, the antibiotic can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g., a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art. The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. Each tablet, capsule, caplet, pill, etc. can be a single dose, with a dose, for example, as herein discussed, or a dose can be two or more tablets, capsules, caplets, pills, etc; for example if a tablet, capsule etc is 125 mg and the dose is 250 mg, the patient may take two tablets, capsules and the like, at each interval there is to administration.

The compositions of the present invention may be formulated with commonly used diluents or excipients, such as fillers, extenders, binders, wetting agents, disintegrants, or surfactants. Solid formulations for oral administration include tablets, pills, powders, granules, or capsules, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, or injectable esters such as ethyl oleate may be used. As the base of the suppositories, witepsol, Macrogol, Tween 61, cacao butter, laurin fat, or glycerogelatin may be used.

The preferred dose of the pharmaceutical compositions of the present invention varies depending on the patient's condition and weight, the severity of the disease, the type of drug, and the route and period of administration and may be suitably selected by those skilled in the art. For preferred effects, the pharmaceutical composition of the present invention may be administered at a dose of 0.01-100 mg/kg/day. The administration may be anywhere from 1 to 4 times daily, e.g., once, twice, three times or four times daily. The maximum amount administered in a 24-hour period may be up to 1500 mg. The administration may be over a course of 2 to 30 days, e.g., 3 to 21 days, such as 7, 10 or 14 days. The skilled person can adjust dosing depending on the subject's body weight and overall health condition and the purpose for administering the antibiotic. Repeated courses of treatment may be pursued depending on the response obtained.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The compounds can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, Comprehensive Organic Transformations, 2d.ed., Wiley-VCH Publishers (1999); P. G. M. Wuts and T. W. Greene, Protective Groups in Organic Synthesis, 4th Ed., John Wiley and Sons (2007); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., 1H or 13C), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or 19F NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

EXAMPLES

The invention is now described with reference to the following Examples. These Examples are provided for the purpose of illustration only, and the invention is not limited to these Examples, but rather encompasses all variations that are evident as a result of the teachings provided herein.

Unless noted otherwise, the starting materials for the synthesis described herein were obtained from commercial sources or known synthetic procedures and were used without further purification.

All oxygen and/or moisture sensitive reactions were carried out under $N_2$ atmosphere in glassware that had flame-dried under vacuum (0.5 mmHg) and purged with $N_2$ prior to use. All reagents and solvents were purchased from commercial vendors and used as received, or synthesized using literature proceduresNMR spectra were recorded on a Bruker 400 (400 MHz $^1$H, 75 MHz $^{13}$C) or Varian (400 MHz $^1$H, 75 MHz $^{13}$C) spectrometer. Proton and carbon chemical shifts are reported in ppm (δ) referenced to the NMR solvent. Data are reported as follows: chemical shifts, multiplicity (br=broad, s=singlet, t=triplet, q=quartet, m=multiplet; coupling constant (s) in Hz). Unless otherwise indicated NMR data were collected at 25° C. Flash chromatography was performed using 100-200 mesh Silica Gel. Liquid Chromatography/Mass Spectrometry (LCMS) was performed on Agilent1200HPLC and 6110MS. Analytical thin layer chromatography (TLC) was performed on 0.2 mm silica gel plates. Visualization was accomplished with UV light and aqueous potassium permanganate ($KMnO_4$) stain followed by heating.

Example 1

The examples illustrate a non-limiting synthetic scheme that may be used to prepare selected, non-limiting examples of compounds of the invention.

Six intermediate diazabicyclo nonane carboxamide derivatives were synthesized for reaction with various substituted benzene derivatives in order to produce compounds of the current invention. Detailed below are synthetic schemes which may be used to produce six diazabicyclo intermediates (I1-I6), phenyl moieties (SB1-SB13), and inventive Compounds 10 and 24 disclosed above in Table 1.

Synthesis of Diaxabicyclo Nonane Carboxamide Derivatives (I1-I6)
Synthesis of Intermediate 1 (I1)
Synthesis of Intermediate 1 was performed via the sequential synthesis of compounds I1-1, I1-3, I1-4, I1-6, I1-7, I1-8, and I1-9 starting from compound A.
Compound I1-1

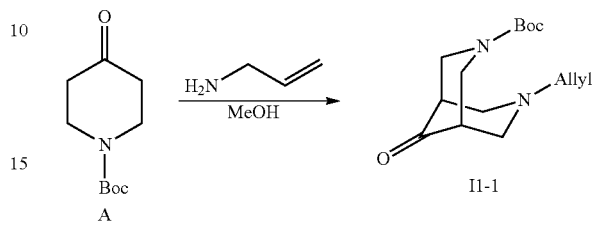

A mixture of prop-2-en-1-amine (30.08 g, 526.97 mmol, 39.58 mL) in dry MeOH (1200 mL) was added to AcOH (30.14 g, 501.88 mmol, 28.70 mL), paraformaldehyde (45.21 g, 501.88 mmol) and HCl (12 M, 20.91 mL) in one portion. The mixture was refluxed at 80° C. and Compound I1-A (100.00 g, 501.88 mmol) in MeOH (500 mL) was added to above solution over 30 min. The mixture was stirred at 80° C. for 16 hours. LCMS of the mixture indicated that Compound I1-A was no longer present in the mixture and one main peak with the MS spectra of compound I1-1 was detected. The mixture was cooled to 25° C. and concentrated at reduced pressure at 40° C. The residue was poured into 800 mL $NH_3/H_2O$ (5M) mixture and the aqueous phase was extracted with Ethyl acetate (300 mL×3). The combined organic phase was washed with saturated brine (200 mL×2), dried over anhydrous $Na_2SO_4$, filtered and concentrated in vacuum. The residue was purified by silica gel chromatography (column height: 250 mm, diameter: 100 mm, 100-200 mesh silica gel, petroleum ether:ethyl acetate mixture with a ratio of 10:1 or 3:1) to afford tert-butyl 7-allyl-9-oxo-3,7-diazabicyclo[3.3.1]nonane-3-carboxylate (106.00 g, crude) as light yellow oil.
Compound I1-3 n-BuLi (2.5 M, 42.80 mL) was added dropwise at −78° C. under $N_2$ to a solution of 1,4-dibromobenzene (25.24 g, 107.01 mmol) in THF (300 mL). The mixture was stirred at −78° C. for one hour and then a solution of Compound I1-1 (30.00 g, 107.01 mmol) in THF (50 mL) was added at −78° C. and the mixture was stirred at −78° C. for another hour. LCMS showed most desired product I1-3 was formed as a mixture. The reaction was quenched with saturated $NH_4Cl$ (300 mL) and extracted with EtOAc (200 mL*3). The combined organic phase was washed with brine (200 mL*3), dried over anhydrous $Na_2SO_4$, filtered and concentrated. The residue was purified by column chromatography ($SiO_2$, petroleum ether:ethyl acetate mixture in a ratio of 30:1 to 1:1) to afford Compound I1-3 (19.00 g, crude, mixture) as a light yellow solid. Unless otherwise indicated, a range of ratios or two specified ratios of eluents for a column chromatographic separation indicate that the initial ratio of components was used and gradually altered during chromatographic separation until the final ratio was achieved. In this case, the eluent initially had a ratio petroleum ether:ethyl acetate of 30:1 (vol:vol) and ethyl acetate was slowly added to the eluent mixture until the mixture had final ratio of 1:1. Unless otherwise indicated, all ratios of eluent components are vol:vol.

Compound I1-4

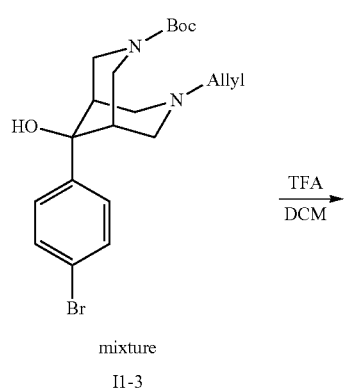

mixture
I1-3

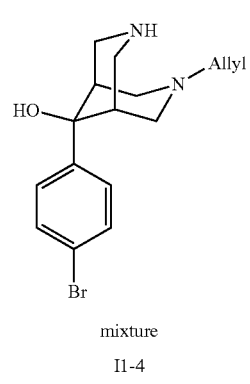

mixture
I1-4

10.00 mL TFA was added to a solution of Compound I1-3 (3.50 g, 8.00 mmol) in DCM (20.00 mL). The mixture was stirred at 15° C. for one hour. LCMS showed the mixture comprised mostly desired product (compound I1-4). The reaction was concentrated to afford 5.00 Compound I1-4 (5.00 g, crude, TFA) as yellow oil and it was used into the next step without further purification.

Compound I1-6

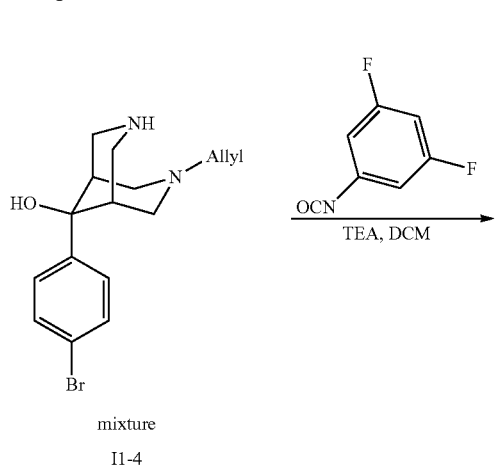

mixture
I1-4 single isomer
I1-6

TEA (1.56 g, 15.40 mmol) and 3,5 difluorophenyl isocyanate (716.56 mg, 4.62 mmol) were added to a solution of Compound I1-4 (1.30 g, 3.85 mmol) in DCM (30.00 mL). The mixture was stirred at 15° C. for 1 hour. LCMS of the mixture indicated the presence of compound I1-6. The reaction was concentrated to give a residue. The residue was purified by prepatory high pressure liquid chromatography with TFA condition to yield 280.00 mg compound I1-6 as a light yellow solid as a single isomer. NMR spectra of were measured using $CDCl_3$ and a frequency of 400 mHz resulting in chemical shifts of δ(ppm)=7.55 (d, J=8.6 Hz, 2H), 7.35 (d, J=8.6 Hz, 2H), 6.90 (br dd, J=1.9, 9.1 Hz, 2H), 6.43 (tt, J=2.3, 8.9 Hz, 1H), 5.76 (tdd, J=6.4, 10.4, 17.0 Hz, 1H), 5.22-5.07 (m, 2H), 3.92 (br d, J=12.9 Hz, 2H), 3.28 (br dd, J=2.6, 12.8 Hz, 2H), 3.11-2.93 (m, 4H), 2.82 (br d, J=10.8 Hz, 2H), 2.63 (br s, 2H).

Compound I1-8                                    Compound I1-9

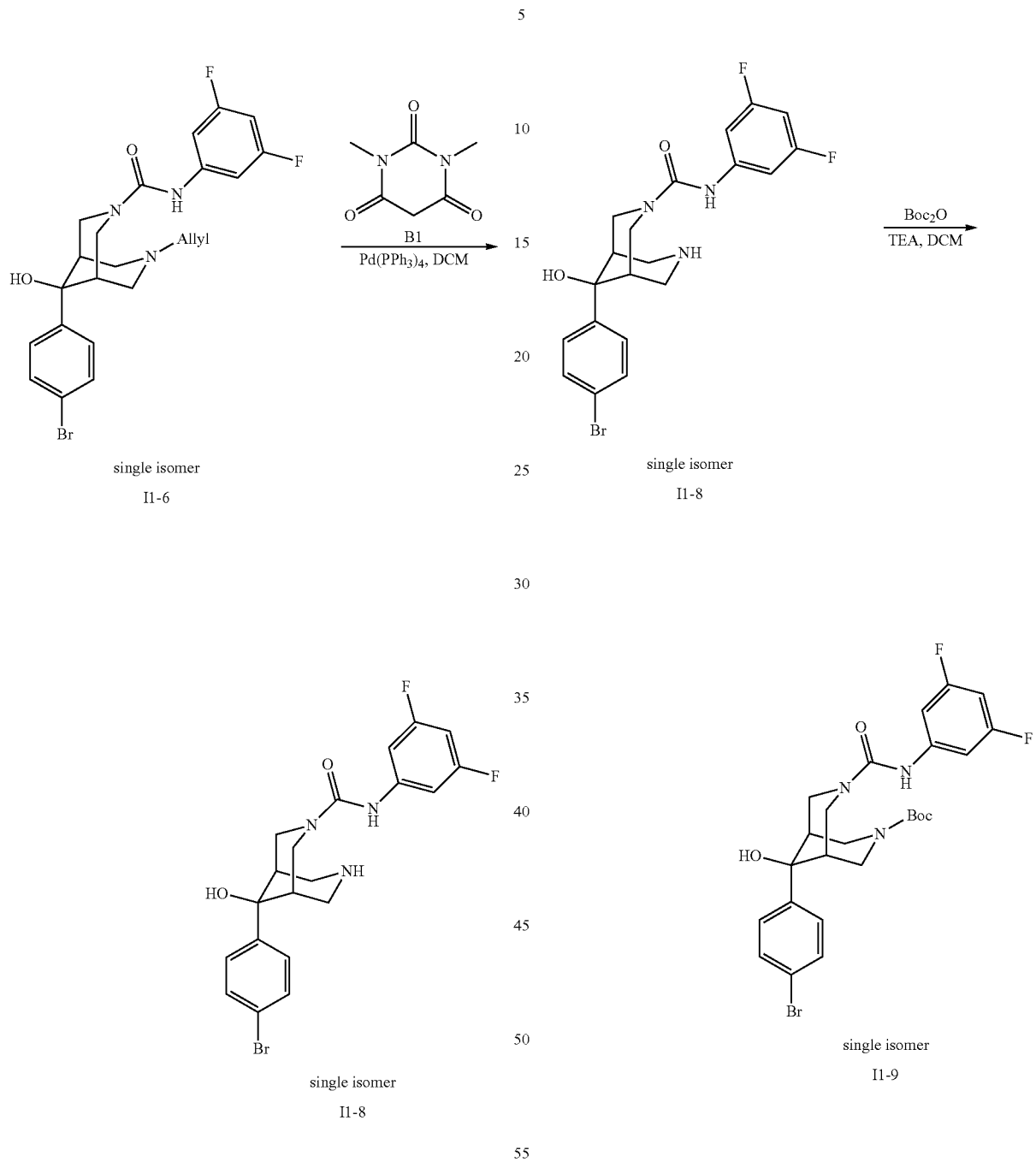

Pd(PPh$_3$)$_4$ (32.86 mg, 28.43 µmol) was added to a mixture of Compound I1-6 (280.00 mg, 568.69 µmol) and Compound B1 (133.19 mg, 853.03 µmol) in DCM (20.00 mL). The mixture was degassed and purged with N$_2$ three times and then stirred at 50° C. for 12 hours under N$_2$ atmosphere. CMS indicated the production of Compound I1-8. The reaction mixture was filtered and concentrated to yield Compound I1-8 (300.00 mg, crude) as a yellow solid, which was used into the next step without further purification.

TEA (201.35 mg, 1.99 mmol) and Boc$_2$O (144.76 mg, 663.29 µmol) were added to a solution of Compound I1-8 (300.00 mg, 663.29 µmol) in DCM (10.00 mL). The mixture was stirred at 15° C. for 1 hour. LCMS showed the reaction was complete. The reaction was concentrated to give a residue which was purified by prepatory thin layer chromatography (SiO$_2$, petroleum ether/ethyl acetate mixture in a ratio of 1:1) to afford Compound I1-9 (220.00 mg, crude) as a yellow solid.

Intermediate 1

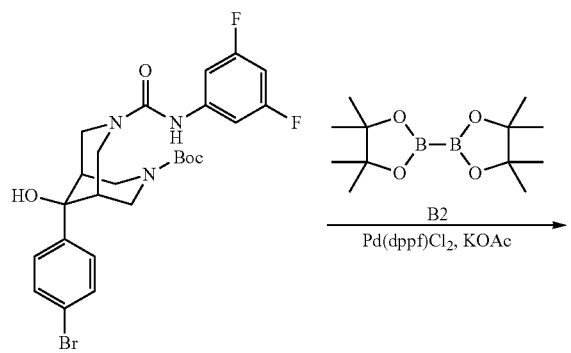

single isomer
I1-9

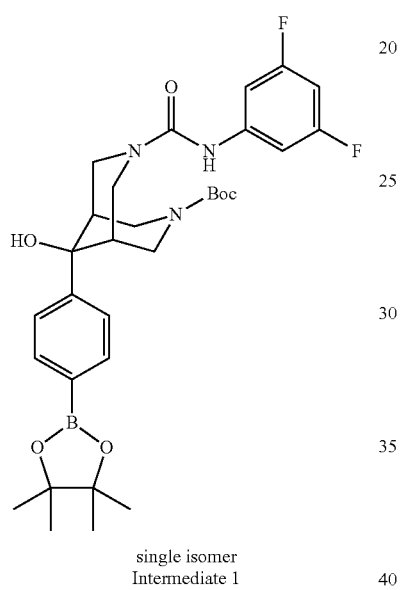

single isomer
Intermediate 1

A mixture of Compound I1-9 (90.00 mg, 162.92 µmol), Compound B2 (45.51 mg, 179.21 µmol), KOAc (23.98 mg, 244.38 µmol) and Pd(dppf)Cl$_2$ (11.92 mg, 16.29 µmol) in dioxane (4.00 mL) was degassed and purged with N$_2$ three times. The mixture was stirred at 90° C. for 12 hours under N$_2$ atmosphere. LCMS showed the resultant mixture to comprise only Intermediate 1, and none of Compound I1-9. The reaction was concentrated to give a residue. The residue was purified by prepatory ("prep")-TLC (SiO$_2$, petroleum ether/ethyl acetate mixture in a ratio of 1:2) to afford Intermediate 1 (90.00 mg, crude) as a white solid.

The following reactions describe the full synthesis pathway to Intermediate 1.

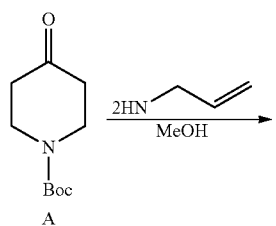

A

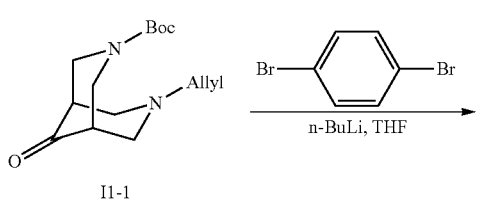

I1-1

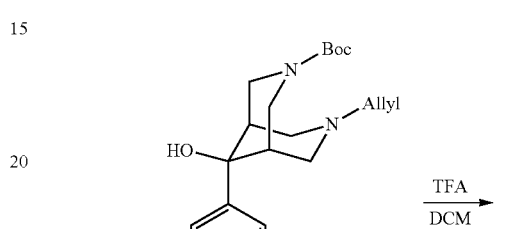

I1-3

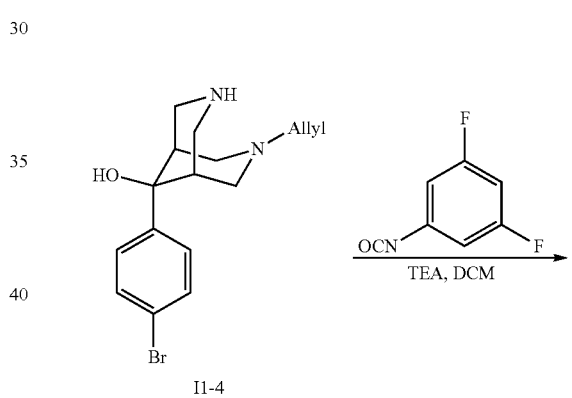

I1-4

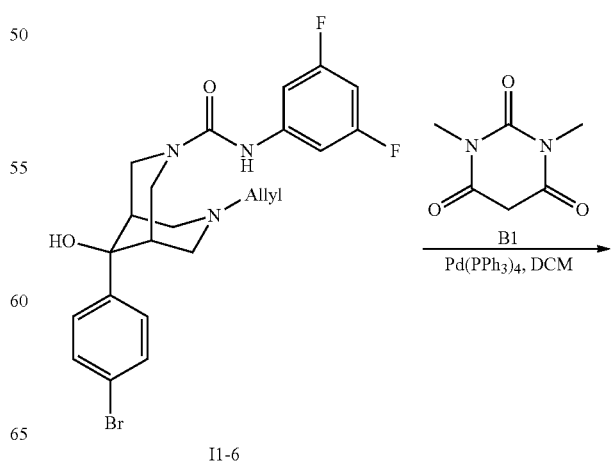

I1-6

Synthesis of Intermediate 2 (I2)

Synthesis of Intermediate 2 was performed via the sequential synthesis of compounds I2-1, I2-2, I2-3 starting from compound A.

Compound I2-1

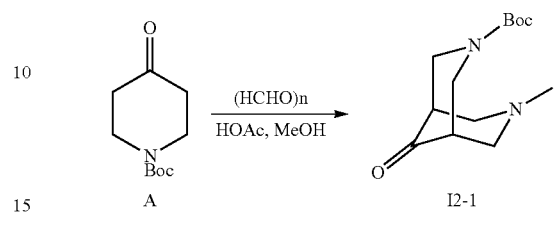

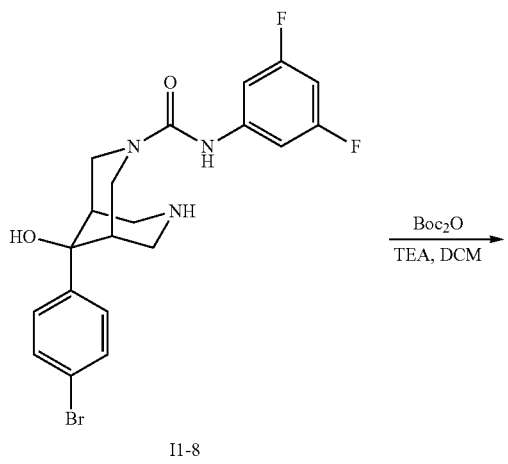

HCl (12 M, 10.76 mL), paraformaldehyde (18.17 g, 201.76 mmol) and AcOH (9.04 g, 150.57 mmol) was added to a mixture of methanamine (32.74 g, 316.19 mmol, 30%) in dry MeOH (800 mL) in one portion. The mixture was refluxed at 80° C. and Compound A (60.00 g, 301.13 mmol) in MeOH (200 mL) was added to above solution over 30 min. The mixture was stirred at 80° C. for 16 hours. LCMS showed the reaction had completed following stirring. The mixture was concentrated to get crude residue and diluted with NH$_4$OH (5 M, 500 mL) and extracted with EtOAc (300 mL*3). The combined organic layers were washed with brine (100 mL*3), dried over Na$_2$SO$_4$, filtered and concentrated under reduced pressure to give a residue. The residue was purified by column chromatography (SiO$_2$, petroleum ether:ethyl acetate mixture in a ratio of 10:1 to 3:1) to afford Compound I1 (33.50 g, crude) as a colorless oil.

Compound I2-2

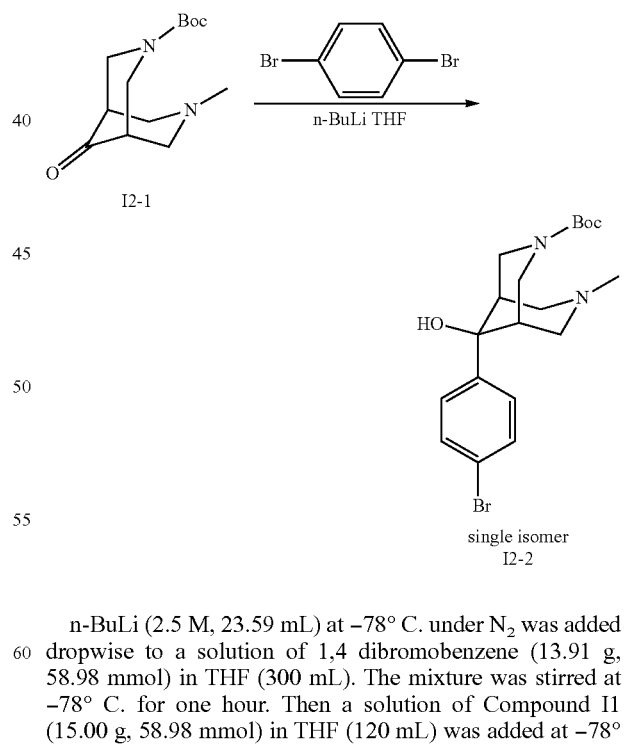

n-BuLi (2.5 M, 23.59 mL) at −78° C. under N$_2$ was added dropwise to a solution of 1,4 dibromobenzene (13.91 g, 58.98 mmol) in THF (300 mL). The mixture was stirred at −78° C. for one hour. Then a solution of Compound I1 (15.00 g, 58.98 mmol) in THF (120 mL) was added at −78° C., the mixture was stirred at −78° C. for another 1 hour. LCMS showed most desired product had formed. The reaction was quenched with saturated NH$_4$Cl (300 mL) and extracted with EtOAc (200 mL*3). The combined organic phase was washed with brine (200 mL*3), dried over anhydrous $Na_2SO_4$, filtered and concentrated. The residue was purified by column chromatography ($SiO_2$, Petroleum ether/Ethyl acetate mixture in a ratio of 10:1 to 4:1) to afford Compound I2-2 (3.10 g, crude) as light yellow oil.

Compound I2-3

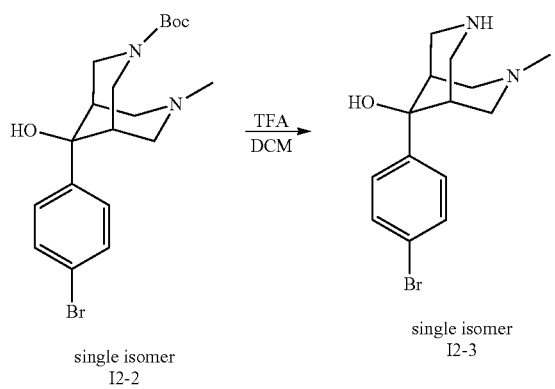 [SMILES: CN1CC2CN(C(=O)OC(C)(C)C)CC(C1)C2(O)c1ccc(Br)cc1 ; CN1CC2CNCC(C1)C2(O)c1ccc(Br)cc1 ; "TFA"]

5.00 mL TFA was added to a solution of Compound I2-2 (3.00 g, 7.29 mmol) in DCM (30.00 mL). The mixture was stirred at 20° C. for 15 min. LCMS showed the reaction was complete. The reaction was concentrated to afford Compound I2-3 (2.27 g, crude) as yellow oil, which was used into the next step without further purification.

Intermediate 2

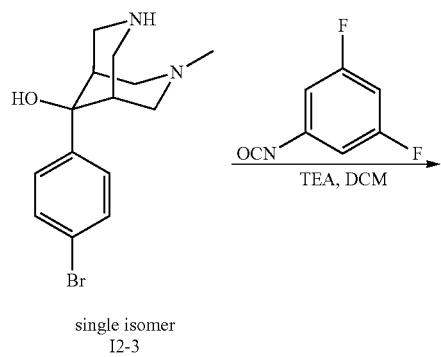

TEA (1.46 g, 14.46 mmol) and 3,5 difluorophenyl isocyanate (747.54 mg, 4.82 mmol) was added to a solution of Compound I2-3 (1.50 g, 4.82 mmol) in DCM (30.00 mL). The mixture was stirred at 25° C. for 1 hour. LCMS showed the reaction was complete. The reaction was filtered and the cake was washed with DCM (30 mL*3). The filtrate was concentrated to give a residue. The residue was purified by column chromatography ($SiO_2$, petroleum ether:ethyl acetate mixture with a ratio of 3:1 to 0:1) to afford Intermediate 2 (1.20 g, crude) as a white solid. NMR spectra of were measured using MeOD and a frequency of 400 mHz resulting in chemical shifts of δ(ppm)=7.58 (br d, J=8.2 Hz, 2H), 7.46 (br d, J=8.4 Hz, 2H), 7.11 (br d, J=8.6 Hz, 2H), 6.52 (br t, J=8.7 Hz, 1H), 4.10 (d, J=12.6 Hz, 2H), 3.85 (br d, J=11.2 Hz, 2H), 3.30 (td, J=1.6, 3.3 Hz, 2H), 2.90 (br s, 2H), 2.75-2.52 (m, 2H), 2.50-1.62 (m, 5H).

The following reaction schemiatic describes the full synthesis pathway to Intermediate 2.

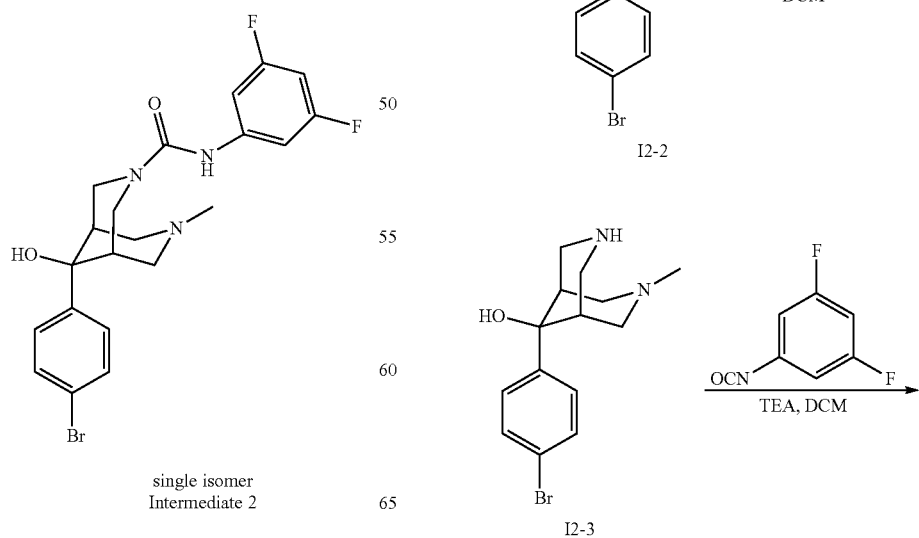

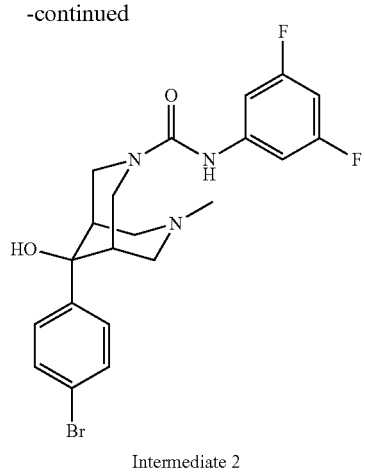

Intermediate 2

Synthesis of Intermediate 3 (I3)
Synthesis of Intermediate 3 was performed via the sequential synthesis of compounds I3-1, I3-2, I3-4 starting from compound I1-1.
Compound I3-1

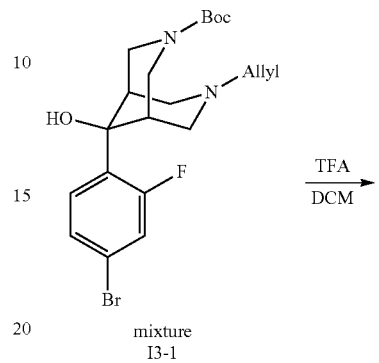

n-BuLi (2.5 M, 1.50 mL) was added dropwise over 30 min at −78° C. to a solution of 1-bromo-3-fluoro-4-iodo-benzene (1.13 g, 3.75 mmol) in THF (20 mL). A solution of Compound I1-1 (1.00 g, 3.57 mmol) in THF (10 mL) was then added dropwise to the mixture over 15 min. The resulting mixture was stirred at 15° C. for 45 min. LCMS showed some desired product was formed. The resulting mixture was poured into 50 mL saturated NH₄Cl aqueous solution. The aqueous solution was extracted by EtOAc (20 mL*2). The combined organic layer was washed by brine (15 mL). The organic layer was dried over Na₂SO₄ and concentrated to give a residue which was purified by column chromatography eluted with petroleum ether:EtOAc mixture with a ratio of 10:1. Compound I3-1 (660.00 mg, crude) was obtained as an brown solid as a mixture used for next step directly.

Compound I3-2

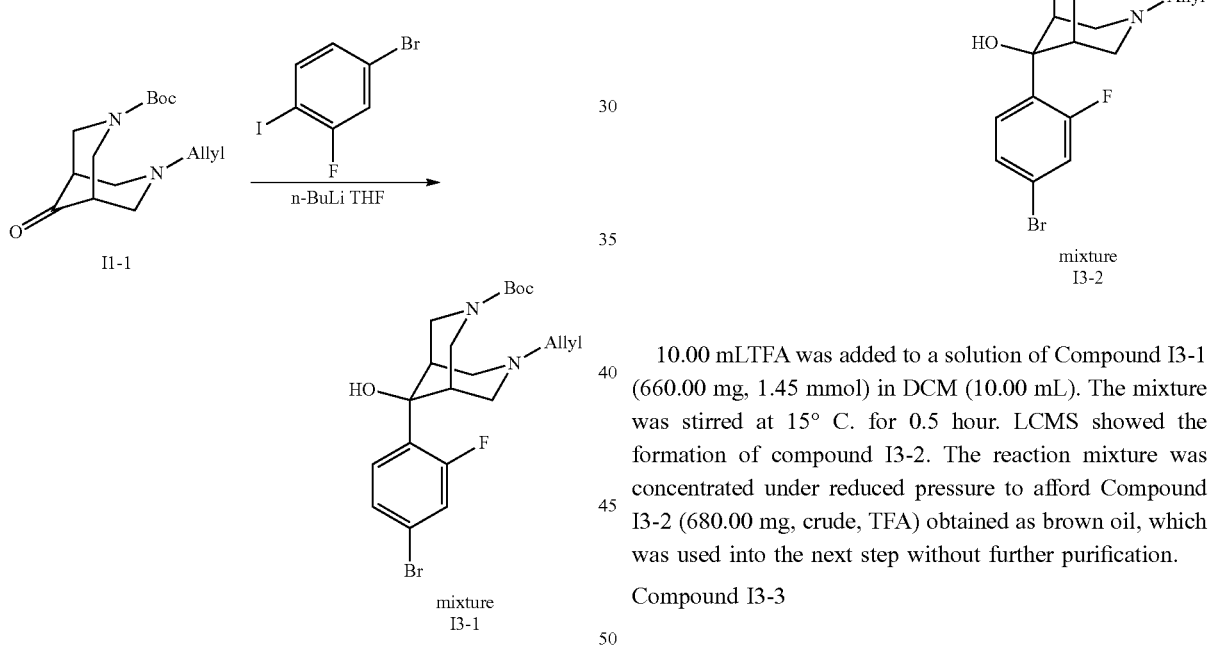

10.00 mLTFA was added to a solution of Compound I3-1 (660.00 mg, 1.45 mmol) in DCM (10.00 mL). The mixture was stirred at 15° C. for 0.5 hour. LCMS showed the formation of compound I3-2. The reaction mixture was concentrated under reduced pressure to afford Compound I3-2 (680.00 mg, crude, TFA) obtained as brown oil, which was used into the next step without further purification.

Compound I3-3

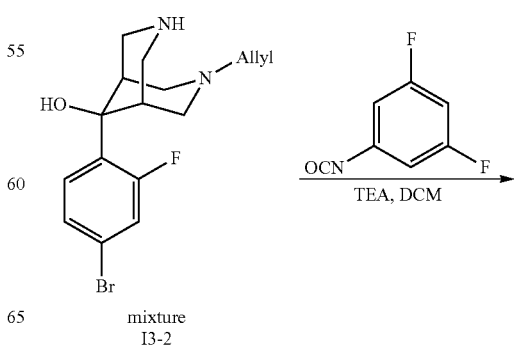

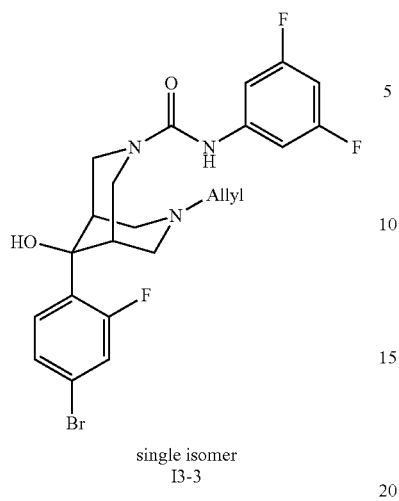

single isomer
I3-3

A mixture of TEA (30.00 mL) and Compound I3-3 (680.00 mg, 1.45 mmol) was added to a solution of 3,5 difluorophenyl isocyanate (224.90 mg, 1.45 mmol) in DCM (30.00 mL). The mixture was stirred at 15° C. for 30 minutes. LCMS showed Compound I3-2 was consumed completely in the reaction and one main peak with desired MS of Compound I3-3 was detected. The reaction mixture was diluted with water 30 mL and extracted with DCM (30 mL*3). The combined organic layer was washed with brine 50 mL, dried over $Na_2SO_4$ and concentrated under reduced pressure to give a residue. The residue was purified by prepatory-HPLC (TFA condition) to afford Compound I3-3 (100.00 mg, crude) as a white solid. NMR spectra of were measured using $CDCl_3$ and a frequency of 400 mHz resulting in chemical shifts of δ(ppm)=7.12-7.28 (m, 3H) 6.86-6.99 (m, 2H) 6.36 (tt, J=8.97, 2.18 Hz, 1H) 5.47-5.63 (m, 1H) 4.88-5.04 (m, 2H) 3.82-3.94 (m, 2H) 3.70-3.82 (m, 2H) 2.90 (br d, J=10.17 Hz, 2H) 2.58-2.72 (m, 4H) 2.11-2.27 (m, 2H).

Compound I3-4

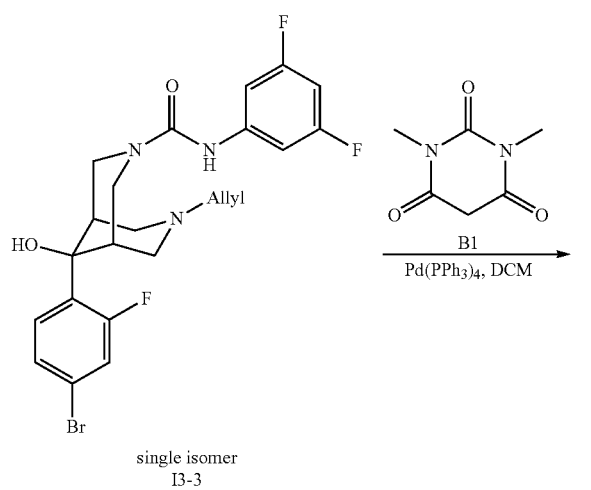

single isomer
I3-3

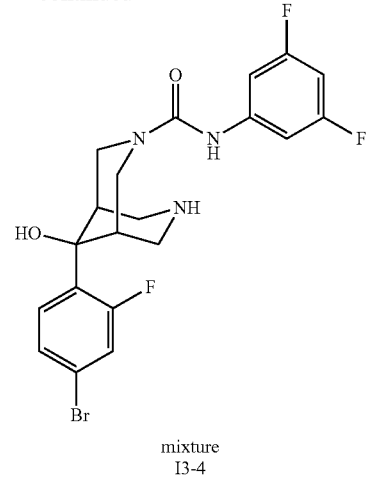

mixture
I3-4

A mixture of Compound I3-4 (100.00 mg, 195.94 μmol) and compound B1 (45.89 mg, 293.92 μmol) in DCM (20.00 mL) was added to $Pd(PPh_3)_4$ (11.32 mg, 9.80 μmol). The mixture was degassed and purged with $N_2$ three times and then stirred at 50° C. for twelve hours under $N_2$ atmosphere. LCMS showed the formation of Compound I3-4. The reaction was filtered and concentrated to give Compound I3-4 (150.00 mg, crude) as a yellow solid mixture, which was used in the next step without further purification.

Intermediate 3

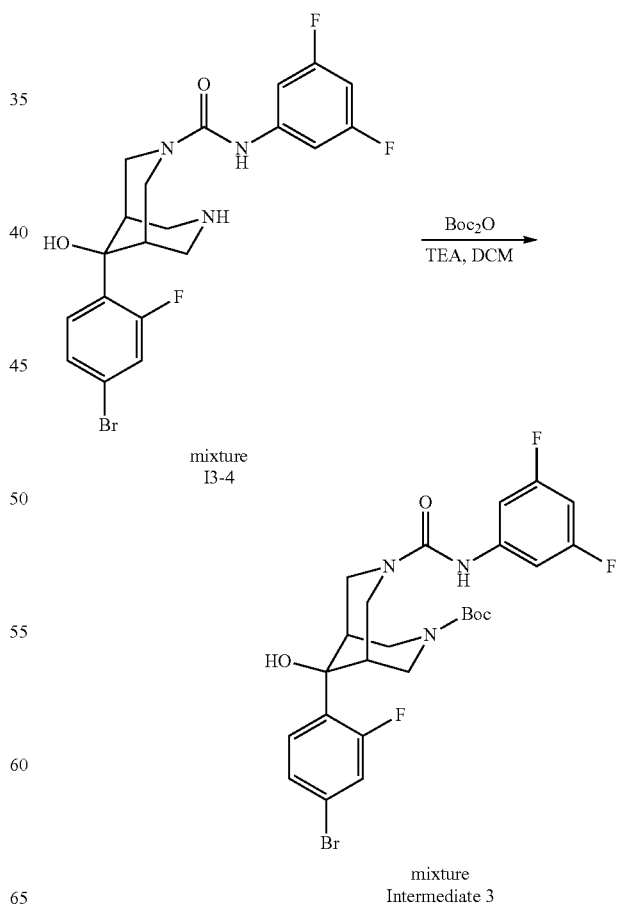

A mixture of TEA (64.55 mg, 637.92 μmol) and Boc₂O (46.41 mg, 212.64 μmol) was added to a solution comprising Compound I3-4 (100.00 mg, 212.64 μmol) in DCM (5.00 mL). The mixture was stirred at 15° C. for one hour. LCMS showed the reaction was complete. The reaction was concentrated to give a residue. The residue was purified by prepatory-TLC (SiO₂, petroleum ether:ethyl acetate mixture with a ratio of 1:1). Intermediate 3 (80.00 mg, crude) was obtained from the prepatory-TLC as a yellow solid.

The following reaction schematic describes the full synthesis pathway to Intermediate 3.

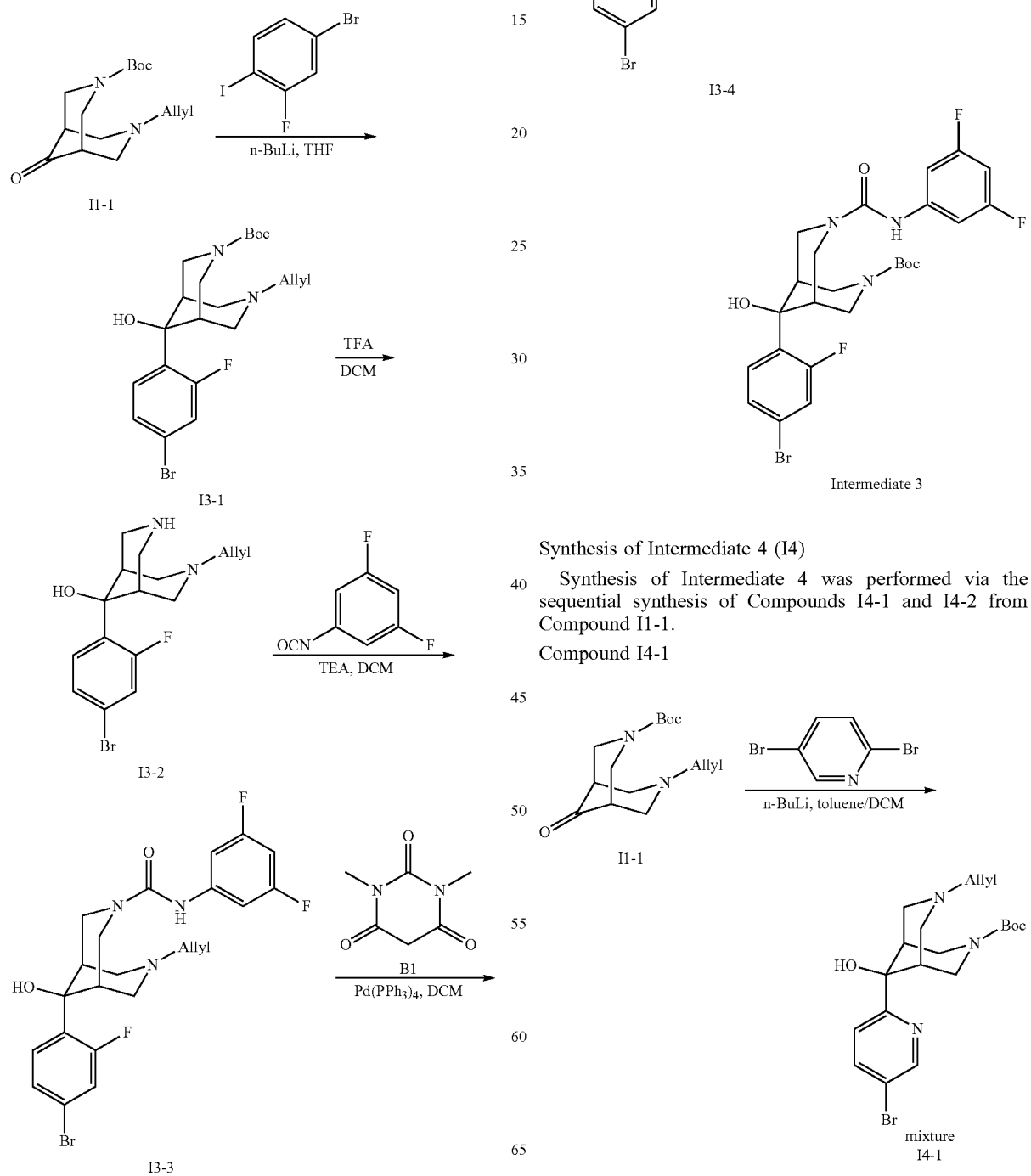

Synthesis of Intermediate 4 (I4)

Synthesis of Intermediate 4 was performed via the sequential synthesis of Compounds I4-1 and I4-2 from Compound I1-1.

Compound I4-1

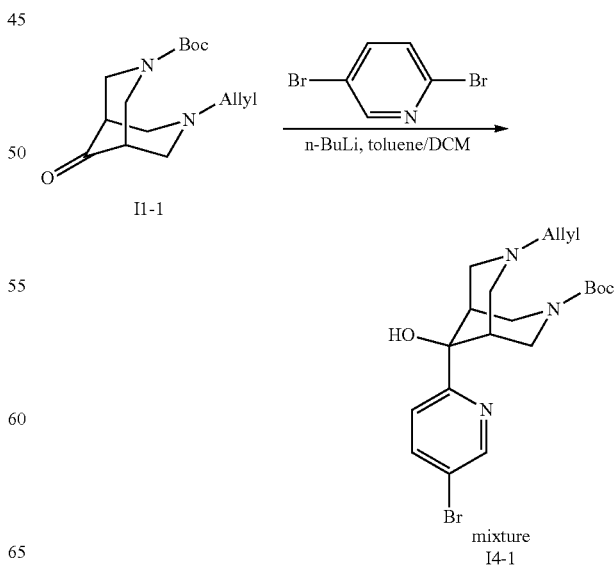

n-BuLi (2.5M, 25.68 mL) was added to a solution of 2-5-dibromopyridine (0.085 M, 629.41 mL) in toluene (630.00 mL) dropwise over 30 min at −78° C. under $N_2$ atmosphere. The reaction mixture was stirred at −78° C. for 40 min. A solution of Compound I1-1 (15.00 g, 53.50 mmol) in DCM (126.00 mL) was added, and then the mixture was stirred at −78° C. for one hour under $N_2$ atmosphere. LCMS showed the reaction was completed. The reaction was diluted with saturated aqueous $NH_4Cl$ (100 mL) and then extracted with EtOAc (80 mL*3). The combined organic was dried over anhydrous $Na_2SO_4$, filtered and concentrated to give a residue. The residue was purified by column chromatography ($SiO_2$, petroleum ether/ethyl acetate eluent with a ratio of 20:1 to 3:1) resulting in Compound I4-1 (23.00 g, crude) as a yellow oil.

Compound I4-2

Pd(PPh₃)₄ (395.20 mg, 342.00 µmol) was added to a solution of Compound I4-1 (3.00 g, 6.84 mmol) and Compound B1 (1.60 g, 10.26 mmol) in EtOH (20.00 mL) and DCM (10.00 mL). The mixture was stirred at 50° C. for twelve hours under $N_2$. LCMS showed the reaction was completed. The mixture was concentrated to afford Compound I4-2 (5.00 g, crude) as a yellow solid was used into the next step without further purification.

Intermediate 4

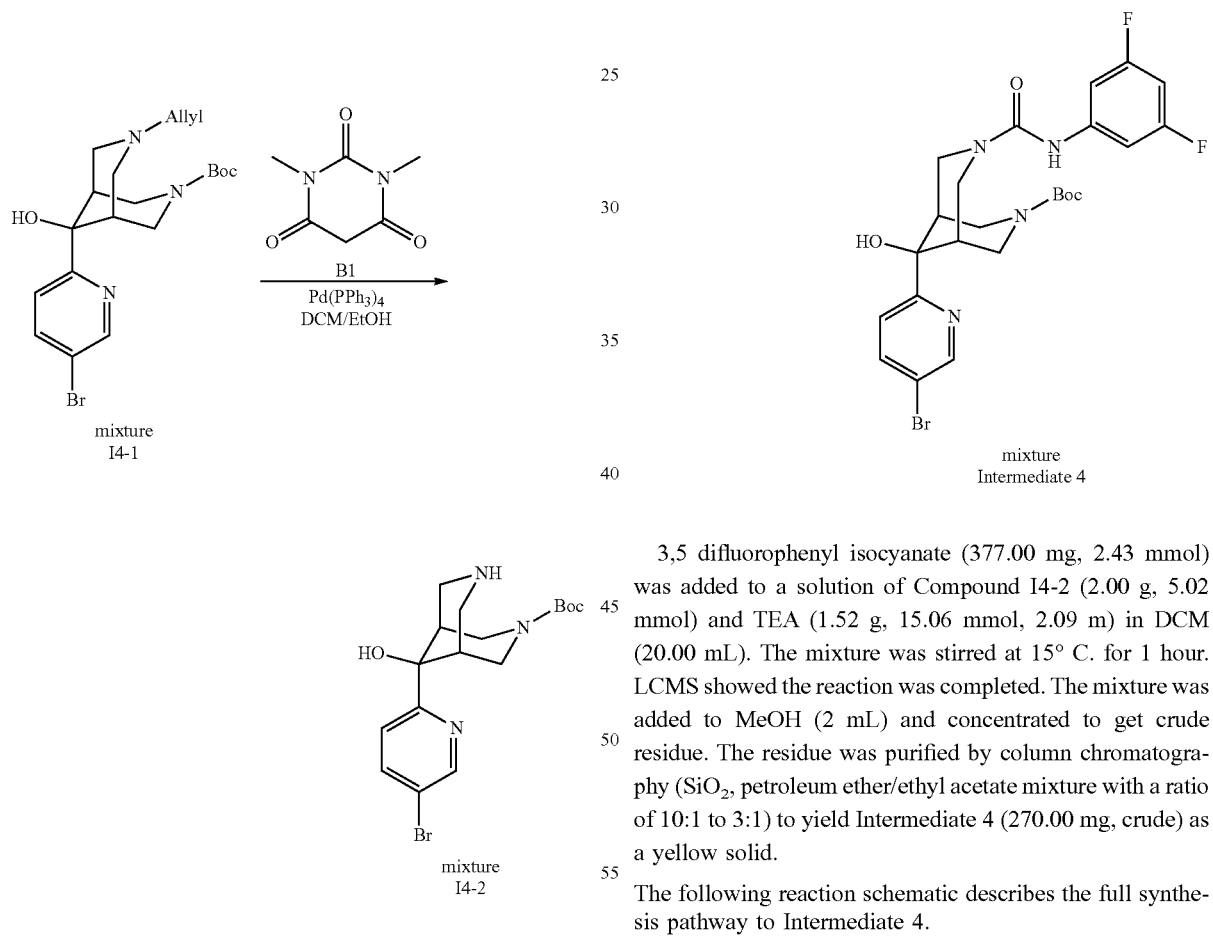

3,5 difluorophenyl isocyanate (377.00 mg, 2.43 mmol) was added to a solution of Compound I4-2 (2.00 g, 5.02 mmol) and TEA (1.52 g, 15.06 mmol, 2.09 m) in DCM (20.00 mL). The mixture was stirred at 15° C. for 1 hour. LCMS showed the reaction was completed. The mixture was added to MeOH (2 mL) and concentrated to get crude residue. The residue was purified by column chromatography ($SiO_2$, petroleum ether/ethyl acetate mixture with a ratio of 10:1 to 3:1) to yield Intermediate 4 (270.00 mg, crude) as a yellow solid.

The following reaction schematic describes the full synthesis pathway to Intermediate 4.

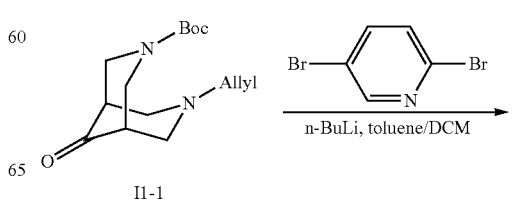

-continued

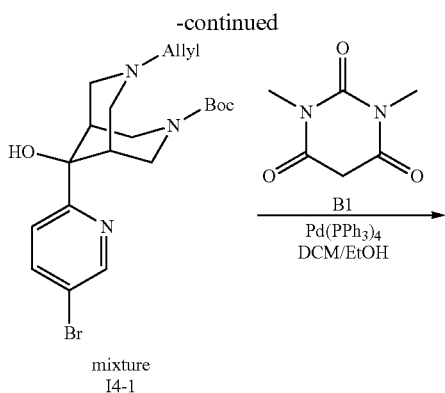

mixture
I4-1

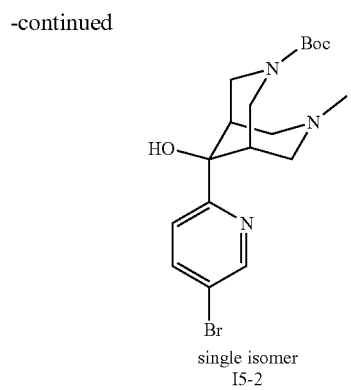

single isomer
I5-2 n-BuLi (2.5 M, 25.50 mL) was added dropwise to a solution of Compound I2-1 in toluene (750.00 mL) at −78° C. under $N_2$. The mixture was stirred at −78° C. for one hour. After stirring, a solution of 2,5 dibromopyridene (16.21 g, 63.74 mmol) in DCM (75.00 mL) was added at −78° C. and the mixture was stirred at −78° C. for another 1 hour. LCMS showed the BuLi reaction was completed. The mixture was poured into 300 mL $NH_4Cl$ and extracted with EtOAc (200 mL*3). The combined organic layers were washed with brine (200 mL*3), dried over $Na_2SO_4$, filtered and concentrated under reduced pressure to give a residue which was purified by column chromatography ($SiO_2$, petroleum ether/ethyl acetate mixture in a 15:1 to 5:1 ratio) to afford Compound 23 (4.30 g, 9.91 mmol, 15.54% yield, 95% purity) as a yellow oil. NMR spectra of were measured using Methanol-d4 and a frequency of 400 mHz resulting in chemical shifts of δ(ppm)=8.65 (d, J=2.0 Hz, 1H), 7.98 (dd, J=2.4, 8.6 Hz, 1H), 7.48 (d, J=8.6 Hz, 1H), 4.09 (br d, J=13.0 Hz, 2H), 3.78-3.56 (m, 2H), 2.84 (br s, 2H), 2.61 (br d, J=6.8 Hz, 2H), 2.21 (br d, J=10.8 Hz, 2H), 1.95 (s, 3H), 1.48 (s, 9H).

Compound I5-3

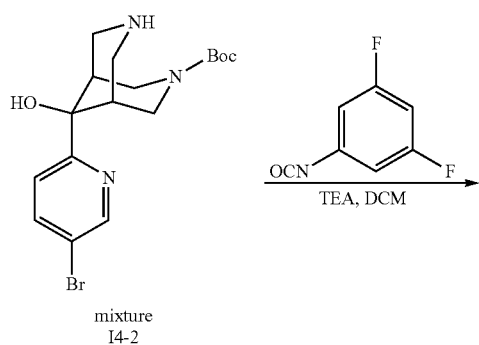

mixture
I4-2

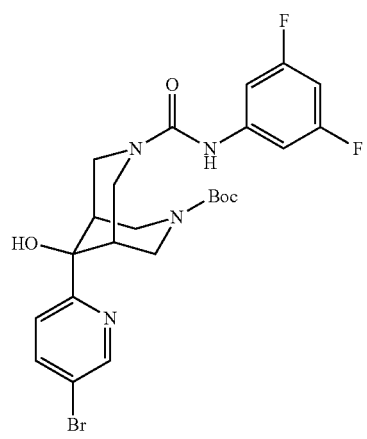

mixture
Intermediate 4

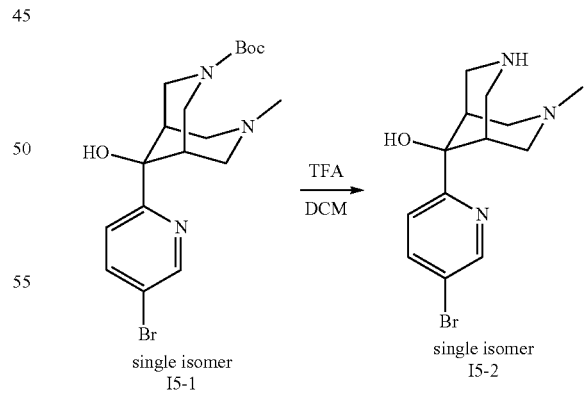

single isomer
I5-1 single isomer
I5-2

Synthesis of Intermediate 5 (I5)

Synthesis of Intermediate 5 was performed via the sequential synthesis of Compounds I5-1 and I5-2 starting from compound I1-1.

Compound I5-1

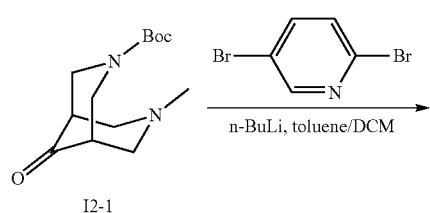

A solution of Compound I5-1 (600.00 mg, 1.46 mmol) in TFA (4.00 mL) and DCM (12.00 mL) was stirred at 15° C. for 30 min. LCMS showed the reaction was completed. The mixture was concentrated to afford Compound I5-2 (620.00 mg, crude, TFA) as a red oil which was used into the next step without further purification.

Intermediate 5

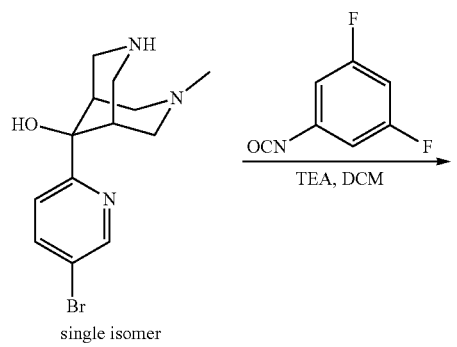

I5-2
single isomer

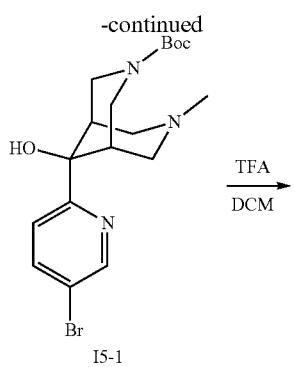

I5-1

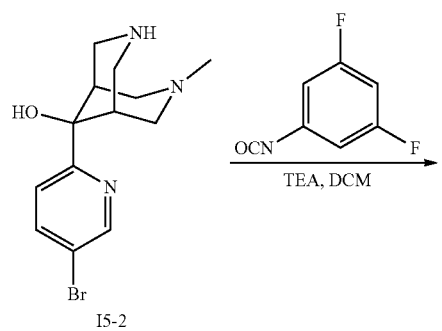

I5-2

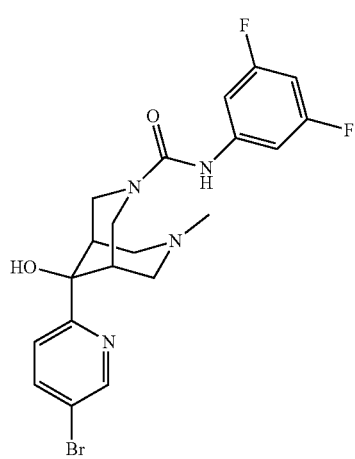

single isomer
Intermediate 5

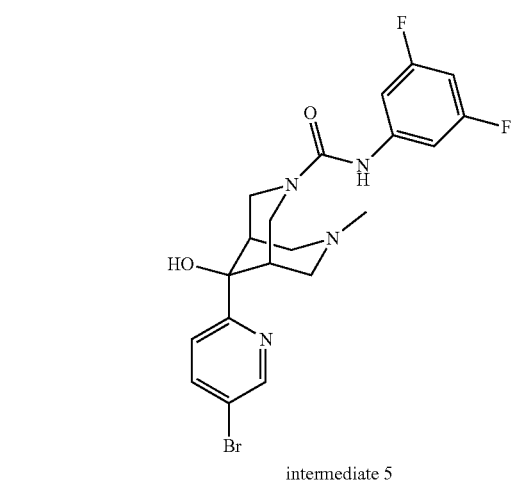

intermediate 5

TEA (441.58 mg, 4.36 mmol) and 3,5 difluorophenyl isocyanate was added to a solution of Compound I5-2 (620.00 mg, 1.45 mmol) in DCM (20.00 mL) and stirred at 15° C. for one hour. LCMS showed the reaction was completed. The mixture was added to MeOH (2 mL) and concentrated to get a crude residue. The residue was purified by column chromatography (SiO$_2$, petroleum ether:ethyl acetate mixture with a 3:1 to 1:1 ratio) to afford Intermediate 5 (500.00 mg, crude) as a yellow solid. NMR spectra of were measured using MeOD and a frequency of 400 mHz resulting in chemical shifts of δ(ppm)=8.69-8.64 (m, 1H), 8.03-7.96 (m, 1H), 7.55-7.48 (m, 1H), 7.14-7.04 (m, 2H), 6.55-6.46 (m, 1H), 4.13-4.05 (m, 2H), 3.83 (br dd, J=1.5, 12.6 Hz, 2H), 2.89 (br d, J=11.0 Hz, 2H), 2.76 (br s, 2H), 2.24 (br d, J=12.1 Hz, 2H), 1.98 (s, 3H).

The following reaction schematic describes the full synthesis pathway to Intermediate 5.

Synthesis of Intermediate 6 (I6)

Synthesis of Intermediate 6 was performed via the sequential synthesis of Compounds I6-1 and I6-2 from compound I1-1.

Compound I6-1

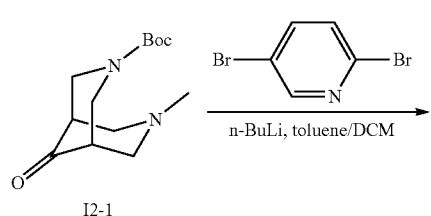

I2-1

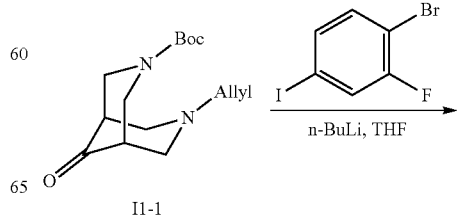

I1-1

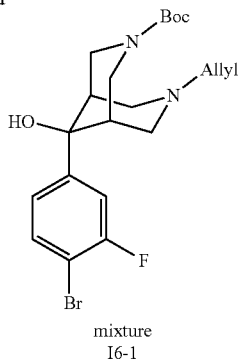

mixture
I6-1

A solution of 1-bromo-2-fluoro-4-iodobenzene (1.00 g, 3.32 mmol) in THF (10 mL) was cooled to −78° C. n-BuLi (2.5 M, 1.33 mL) was then added dropwise under N₂. The mixture was stirred at −78° C. for 1 hour. A solution of Compound I1-1 (930.80 mg, 3.32 mmol) in THF (5 mL) was added dropwise. The mixture was warmed to 15° C. for 1 hour. LCMS showed the reaction was completed. The reaction mixture was diluted by addition NH₄Cl (10 mL) and extracted with EtOAc (10 mL*3). The combined organic layers were washed with brine (10 mL*3), dried over Na₂SO₄, filtered and concentrated under reduced pressure to give a residue. The residue was purified by column chromatography (SiO₂, petroleum ether:ethyl acetate mixture with a 10:1 to 5:1 ratio) to yield Compound I6-1 (1.00 g, crude) as a yellow oil.

Compound I6-2

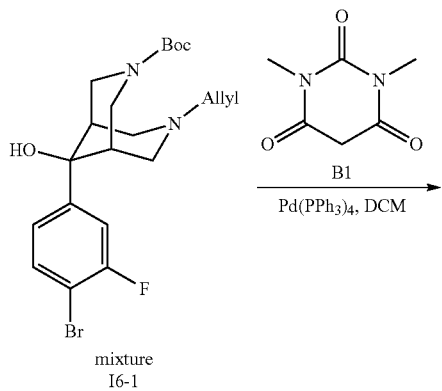

mixture
I6-1

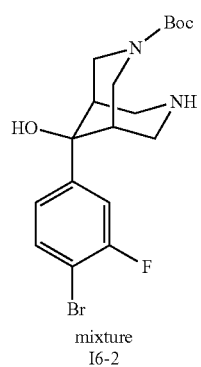

mixture
I6-2

Pd(PPh₃)₄ (126.88 mg, 109.80 μmol) was added to a mixture of Compound I6-1 (1.00 g, 2.20 mmol) and Compound B1 (514.34 mg, 3.29 mmol) in DCM (20.00 mL). The mixture was degassed and purged with N₂ three times, and then stirred at 50° C. for 12 hours under N₂ atmosphere. LCMS showed production of Compound I6-2. The reaction was filtered and concentrated to afford Compound I6-2 (900.00 mg, crude) as a yellow solid which was used in the next step without further purification.

Intermediate 6

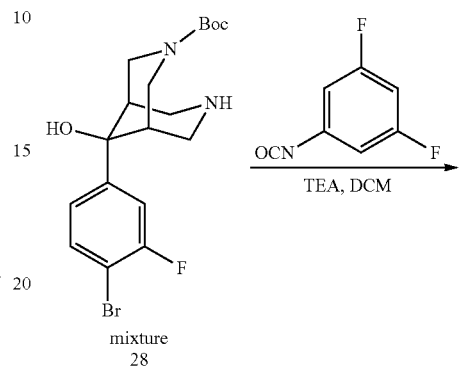

mixture
28

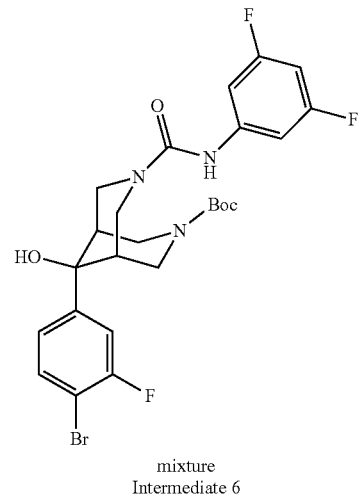

mixture
Intermediate 6

A mixture of TEA (329.37 mg, 3.26 mmol, 451.19 μL) and 3,5 difluorophenyl isocyanate (900.00 mg, 2.17 mmol) was added to a solution of Compound I6-2 (900.00 mg, 2.17 mmol) in DCM (30.00 mL). The mixture was stirred at 15° C. for 1 hour. LCMS showed some desired product was formed. The reaction was concentrated to give a residue. The residue was purified by column chromatography (SiO₂, petroleum ether:ethyl acetate mixture with a 20:1 to 1:1 ratio) to afford Intermediate 6 (380.00 mg, crude) as a yellow solid.

The following reaction schematic describes the full synthesis pathway to Intermediate 6.

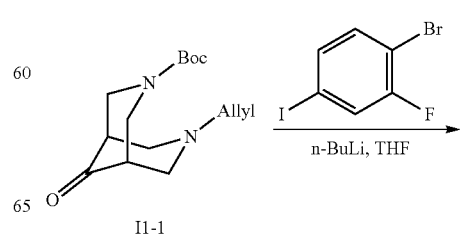

I1-1

-continued
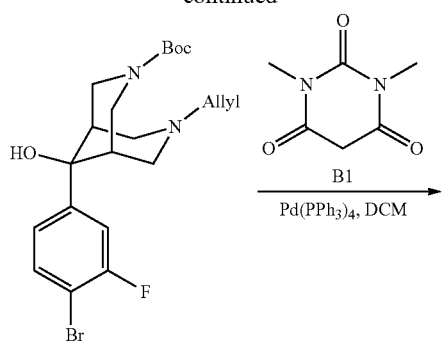
I6-1
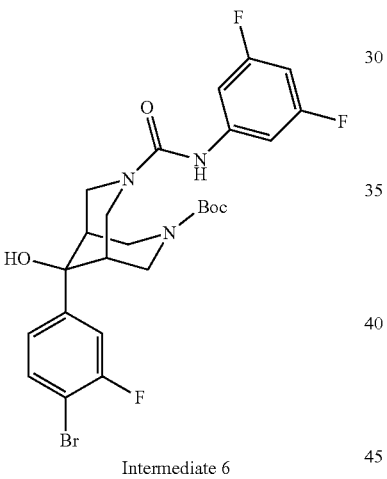
Intermediate 6
Synthesis of Substituted Benzene Derivatives
Table 3 shows the structure of various synthesized benzene derivatives (BD1-BD13) which may be reacted in some synthetic schemes comprising Compounds 11-16 to yield the inventive compounds.
TABLE 3
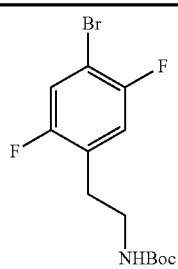
BD1
TABLE 3-continued
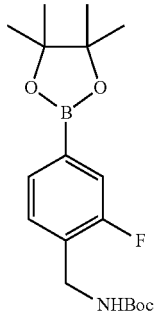 [SMILES: CC(C)(C)OC(=O)NCc1ccc(B2OC(C)(C)C(C)(C)O2)cc1F]
BD2
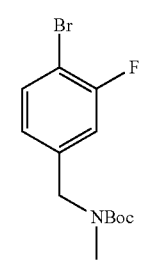 [SMILES: CN(Cc1ccc(Br)c(F)c1)C(=O)OC(C)(C)C]
BD3
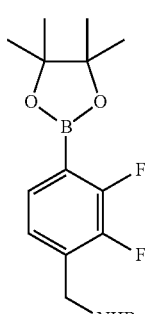
BD4
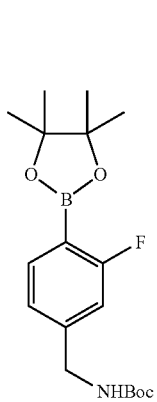 [SMILES: CC(C)(C)OC(=O)NCc1ccc(B2OC(C)(C)C(C)(C)O2)c(F)c1]
BD5
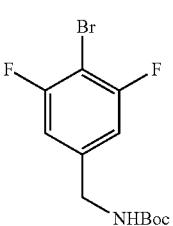 [SMILES: CC(C)(C)OC(=O)NCc1cc(F)c(Br)c(F)c1]
BD6

TABLE 3-continued
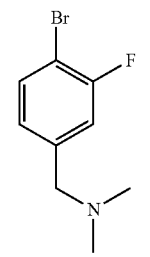
BD7
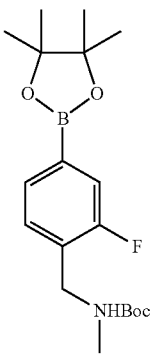
BD8
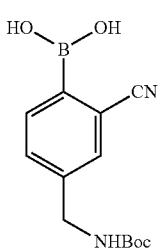 [SMILES: CC(C)(C)OC(=O)NCc1ccc(B(O)O)c(C#N)c1]
BD9
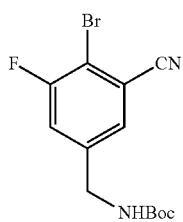 [SMILES: CC(C)(C)OC(=O)NCc1cc(F)c(Br)c(C#N)c1]
BD10
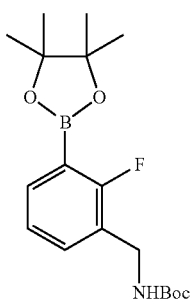 [SMILES: CC(C)(C)OC(=O)NCc1cccc(B2OC(C)(C)C(C)(C)O2)c1F]
BD11
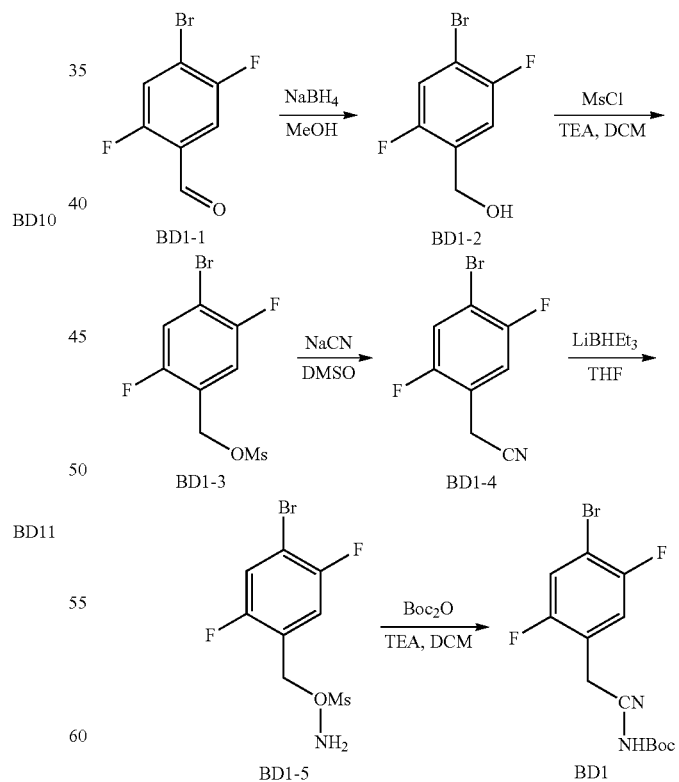
BD12
BD13
Synthesis of BD1
The following reaction schematic describes a synthesis pathway for compound BD1.
NaBH₄ (128.38 mg, 3.39 mmol) was added to a solution of 150.00 g Compound BD1-1 (i.e., 4-bromo-2,5-difluorobenzaldehyde) in MeOH (4.00 mL). The mixture was stirred at 80° C. for 30 minutes. TLC indicated Compound BD1-1 was consumed completely in this reaction time. An additional compound with a larger polarity than Compound BD1-1 was measured. The reaction mixture was concentrated to remove MeOH, then diluted with saturated NaHCO$_3$ (4 ml), extracted with DCM (5 mL*3), the combined organic layer was washed with saturated brine (5 mL*2), dried over Na$_2$SO$_4$, filtered and concentrated to give a residue. The residue was purified by prep-TLC (SiO$_2$, Petroleum ether:Ethyl acetate mixture with a ratio of 3:1) to afford Compound BD1-2 (143.00 mg, 641.23 µmol, 94.47% yield) as a white solid.

TEA (190.56 mg, 1.88 mmol) and methanesulfonyl chloride (86.29 mg, 753.30 µmol) were added to a solution of Compound BD1-2 (140.00 mg, 627.75 µmol) in DCM (2.00 mL). The mixture was stirred at 25° C. for 1 hour. TLC showed Compound BD1-2 was consumed completely and a compound with a polarity lower than Compound BD1-2 was detected. The reaction mixture was diluted with saturated NH$_4$Cl (3 mL) and extracted with DCM (3 mL*3), the combined organic layer was dried over Na$_2$SO$_4$ and concentrated with reduced pressure at 40° C. yielding a residue. The residue was purified by prep-TLC (SiO$_2$, petroleum ether:ethyl acetate mixture in a ratio of 3:1) to afford to Compound BD1-3 (70.00 mg, 232.48 µmol) as a yellow oil.

NaCN (17.09 mg, 348.71 µmol) was added to a solution of Compound BD1-3 (70.00 mg, 232.47 µmol) in DMSO (2.00 mL). The mixture was stirred at 25° C. for 1 hour. TLC showed the reaction was completed and a compound with a polarity greater than Compound BD1-3 was detected. The mixture was diluted with water (5 mL). The aqueous layer of the diluted mixture was then extracted with ethyl acetate (5 mL*3). The organic layer was dried over anhydrous Na$_2$SO$_4$, filtrated and concentrated under vacuum. The residue was purified by prep-TLC (petroleum ether:ethyl acetate mixture in a ratio of 3:1) to afford Compound BD1-4 (25.00 mg, 107.75 µmol, 46.35% yield) as a yellow oil.

LiBHEt$_3$ (1 M, 646.50 µL) was added dropwise to a solution of Compound BD1-4 (25.00 mg, 107.75 µmol) in THF (2.00 mL) at 0° C. The mixture was warmed to 25° C. and stirred for 2 hours. LCMS showed Compound BD1-4 was consumed completely and one main peak with the MS of Compound BD1-5 was detected. The reaction mixture was diluted with saturated NH$_4$Cl (2 mL), then extracted with ethyl acetate (3 mL*3), the combined organic layer was dried over Na$_2$SO$_4$, filtered and concentrated in the reduced pressure at 40° C. to afford Compound BD1-5 (20.00 mg, crude) as a yellow oil.

TEA (25.72 mg, 254.16 µmol) and DMAP (1.04 mg, 8.47 µmol) were added to a solution of Compound BD1-5 (20.00 mg, 84.72 µmol) and Boc$_2$O (18.49 mg, 84.72 µmol) in DCM (2.00 mL). The mixture was stirred at 25° C. for 1 hour. LCMS showed Compound BD1-5 was consumed completely and one main peak with desired MS of Compound BD1 was detected. The reaction mixture was concentrated in the reduced pressure at 40° C. to give a residue. The residue was purified by prepatory-TLC (SiO$_2$, Petroleum ether:Ethyl acetate mixture with a ratio of 1:1) to afford Compound BD1 (10.00 mg, yield 35.12%) as a yellow oil.

Synthesis of BD2
The following reaction schematic describes a synthesis pathway for Compound BD2.

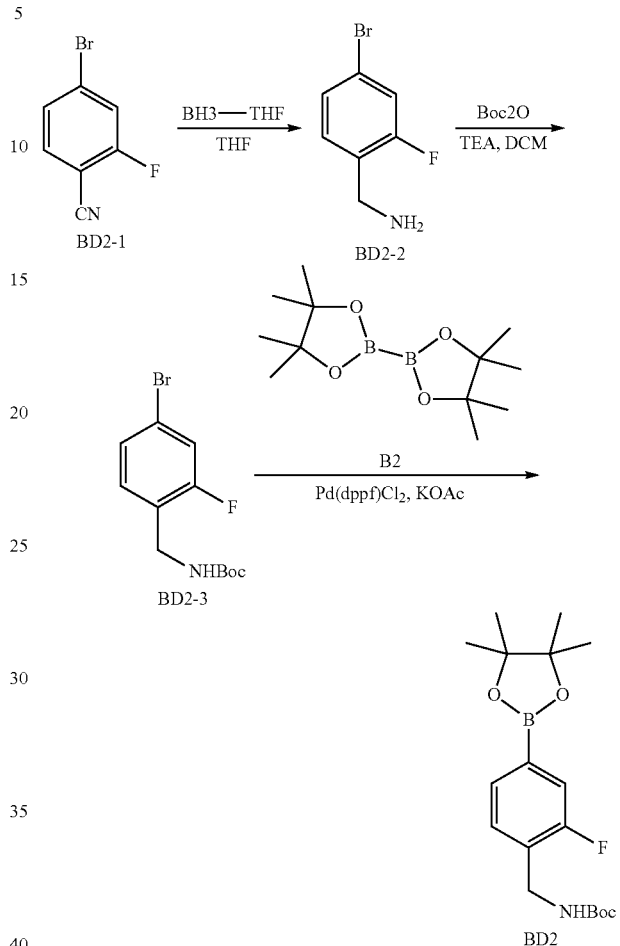

A solution of 100.00 mg Compound BD2-1 (i.e., 4-bromo-2-fluorobenzonitrile) in THF (2.00 mL) was cooled to 0° C. Then BH3-THF (1 M, 1.50 mL) was added and stirred at 60° C. for 0.5 hour. LCMS showed the reaction was completed. The reaction mixture was diluted by addition of MeOH (3 mL) and then concentrated under reduced pressure to afford Compound BD2-2 (100.00 mg, crude) as a red oil.

Boc$_2$O (106.96 mg, 490.10 µmol) and DMAP (5.99 mg, 49.01 µmol) were added to a solution of Compound BD2-2 (100.00 mg, 490.10 µmol) and TEA (148.78 mg, 1.47 mmol) in DCM (4.00 mL). The mixture was stirred at 15° C. for 12 hours. LCMS showed the reaction was completed. The mixture was concentrated to get crude residue. The residue was purified by prepatory-TLC (SiO$_2$, Petroleum ether:Ethyl acetate mixture with a ratio of 5:1) to afford Compound BD2-3 (90.00 mg, crude) as a yellow oil.

Compound B2 (75.14 mg, 295.91 µmol and Pd(dppf)Cl$_2$ (21.65 mg, 29.59 µmol) were added to a solution of Compound BD2-2 (90.00 mg, 295.91 µmol) and KOAc (87.12 mg, 887.72 µmol) in dioxane (2.00 mL). The mixture was stirred at 90° C. for 12 hours under N$_2$. LCMS showed the reaction was completed. The mixture was concentrated to get the crude residue. The residue was purified by prep-TLC (SiO$_2$, 5:1 mixture of Petroleum ether:Ethyl acetate mixture) to afford Compound BD2 (90.00 mg, crude) as a yellow oil.

Synthesis of BD3
The following reaction schematic describes a synthesis pathway for Compound BD3.

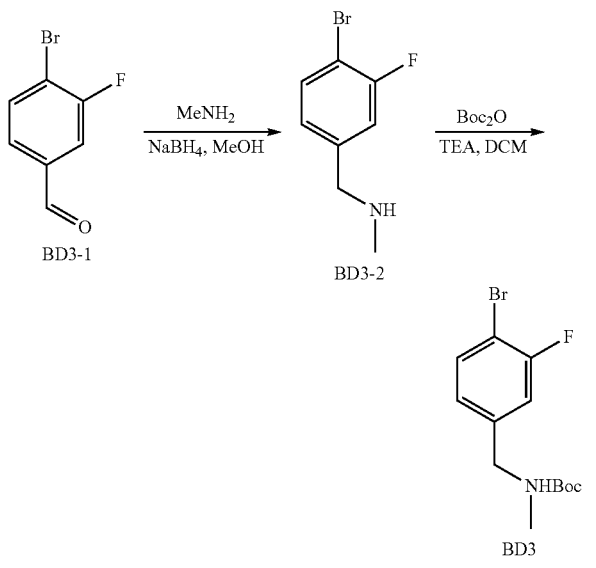

A 30% wt solution of MeNH₂ (1.53 g, 14.79 mmol) in ethanol was added to a solution of 1.00 g Compound BD3-1 (i.e., 4-bromo-3-fluoro-benzaldehyde) in MeOH (30.00 mL). The resulting mixture was stirred at 60° C. for 2 hours then the solution was cooled to 15° C. and NaBH₄ (373.00 mg, 9.86 mmol) was added. The resulting mixture was stirred at 15° C. for 10 hours. LCMS showed some desired product was formed. The solvent was removed under reduced pressure to afford Compound BD3-2 (1.50 g, crude) as a white solid.

TEA (1.50 g, 14.79 mmol, 2.05 mL) and Boc₂O (1.61 g, 7.39 mmol, 1.70 mL) were added to a solution of Compound BD3-2 (1.08 g, 4.93 mmol) in DCM (20.00 mL). The resulting mixture was stirred at 15° C. for 12 hours. LCMS and TLC showed the reaction produced BD3 nearly completely. The solvent was removed under reduced atmospheric pressure. The resultant residue was purified by flash column chromatography eluted with a 5:1 petroleum ether:EtOAc mixture to produce Compound BD3 (1.50 g, crude) as a colorless oil.

Synthesis of BD4
The following reaction schematic describes a synthesis pathway for Compound BD4.

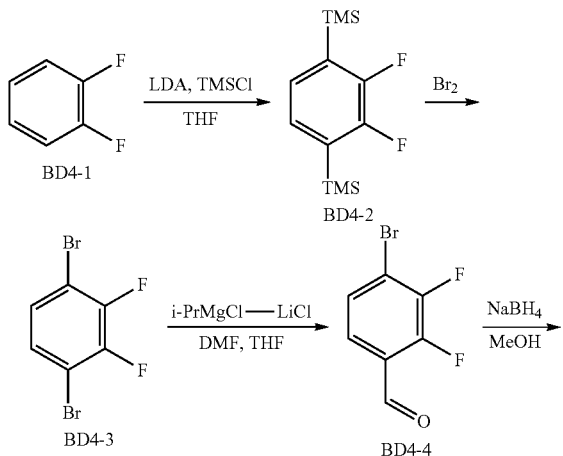

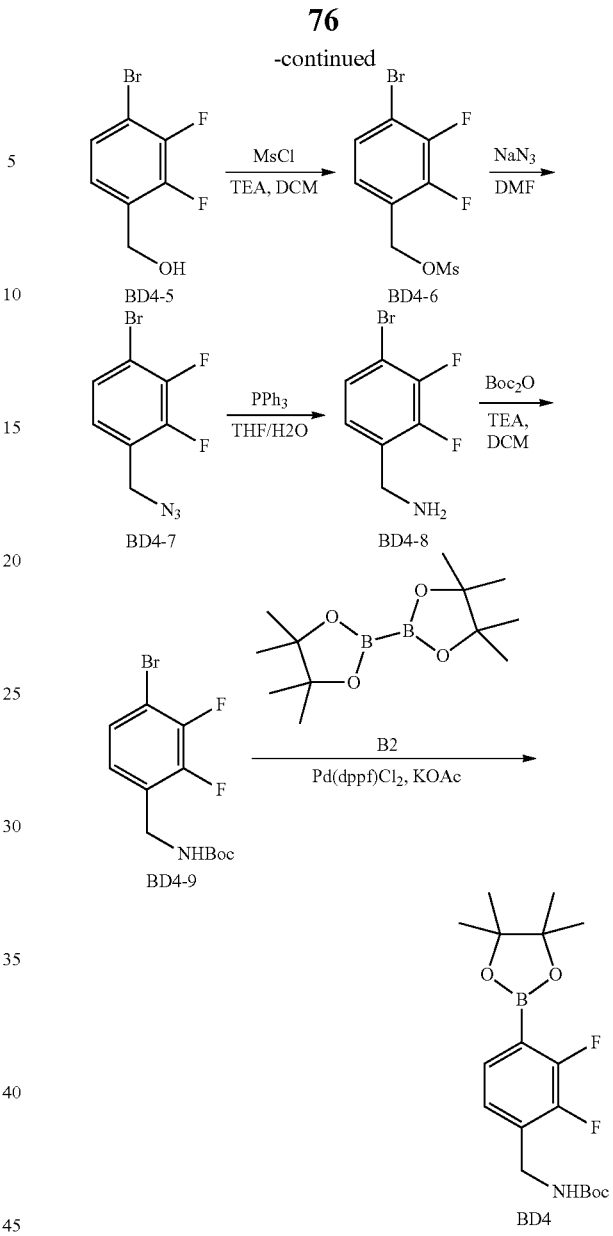

A mixture of 5.00 g Compound BD4-1 (i.e., 1,2 difluorobenzene) and TMSCl (10.48 g, 96.43 mmol) at −78° C. was added to a solution of LDA (2 M, 50.40 mL) in THF (50.00 mL). The mixture was stirred at −78° C. for 1 hour. LCMS and TLC showed 10% of the starting material remained and a new compound had formed in the reaction. The reaction mixture was quenched by addition 1 M sulfuric acid and extracted with EtOAc (50 mL*3). The combined organic layers were washed with brine (30 mL*3), dried over Na₂SO₄, filtered and concentrated under reduced pressure to give a residue. The residue was washed with MeOH (100 mL) to afford Compound BD4-2 (9.00 g, crude) as white needle-like solid.

A solution of Br₂ (18.36 g, 114.92 mmol) was cooled to 0° C. Then Compound BD4-2 (9.00 g, 34.82 mmol) was added portionwise over 30 minutes while maintaining the internal temperature of the solution at 20 to 40° C. The reaction mixture was stirred at 60° C. for 1 hour and then additional 1 mL of bromine was added and stirred for another 1 hour. TLC showed the reaction was completed.

The reaction mixture was diluted by addition of sat. $Na_2SO_3$ (50 mL) and sat. $NaHCO_3$ (50 mL), and then extracted with EtOAc (20 mL*3). The combined organic layers were washed with brine (10 mL*3), dried over $Na_2SO_4$, filtered and concentrated under reduced pressure to afford Compound BD4-3 (7.00 g, crude) as a yellow oil.

i-PrMgCl-LiCl (2 M, 2.03 mL) at −40° C. was added to a solution of Compound BD4-3 (1.00 g, 3.68 mmol) in THF (20.00 mL) at −40° C. The mixture was stirred at −40° C. for 1 hour and again stirred at −7° C. for another 1 hour. The mixture was then cooled to −30° C. DMF (349.66 mg, 4.78 mmol) at −23° C. was added in one portion. The mixture was stirred while keeping a temperature range of −25° C. to 15° C. for 3.5 hour. TLC indicated when the reaction was completed. The reaction mixture was poured into $H_2SO_4$ (100 mL, 1M) cooled to 0° C. by ice bath, and then the resulting mixture was extracted with EtOAc (20 mL*3). The combined organic layers of the reaction mixture were washed with brine (30 mL*3), dried over $Na_2SO_4$, filtered and concentrated under reduced pressure to afford Compound BD4-4 (800.00 mg, crude) as a yellow solid.

$NaBH_4$ (256.49 mg, 6.78 mmol) was added to a solution of Compound BD4-4 (500.00 mg, 2.26 mmol) in MeOH (4.00 mL). The mixture was stirred at 15° C. for 1 hour. TLC showed the reaction had completed. The mixture was concentrated to get crude residue and diluted with $NaHCO_3$ 5 mL and extracted with EtOAc (5 mL*3). The combined organic layers were washed with brine (5 mL*3), dried over $Na_2SO_4$, filtered and concentrated under reduced pressure to yield a residue. The residue was purified by prep-TLC ($SiO_2$, petroleum ether:ethyl acetate mixture with a ratio of 5:1) to afford Compound BD4-5 (300.00 mg, crude) as a yellow oil.

MsCl (231.14 mg, 2.02 mmol) at 0° C. was added to a solution of Compound BD4-5 (300.00 mg, 1.35 mmol) and TEA (408.37 mg, 4.04 mmol) in DCM (4.00 mL). The mixture was stirred at 15° C. for 15 min. LCMS showed the reaction had completed. The mixture was diluted by addition $NaHCO_3$ (3 mL) and extracted with DCM (10 mL*3). The combined organic layers were washed with brine (10 mL*3), dried over $Na_2SO_4$, filtered and concentrated under reduced pressure to afford Compound BD4-6 (400.00 mg, crude) as a yellow oil.

Sodium azide (172.93 mg, 2.66 mmol) was added to a solution of Compound BD4-6 (400.00 mg, 1.33 mmol) in DMF (3.00 mL). The mixture was stirred at 25° C. for 12 hours. TLC indicated Compound BD4-6 was consumed completely and a new compound had been formed. The reaction mixture was diluted by addition water 50 mL at 15° C., and then extracted with EtOAc (50 mL*3). The combined organic layers were washed with 100 mL brine, dried over $Na_2SO_4$, filtered, and concentrated under reduced pressure to afford Compound BD4-7 (350.00 mg, crude) as a yellow oil.

PPh3 (416.23 mg, 1.59 mmol) was added to a solution of Compound BD4-7 (328.00 mg, 1.32 mmol) in THF (6.00 mL) and $H_2O$ (3.00 mL). The mixture was stirred at 50° C. for 12 hours under $N_2$ pressure. LCMS showed the reaction had completed. The reaction mixture was extracted with EtOAc (5 mL*3). The combined organic layers were washed with brine (5 mL*3), dried over $Na_2SO_4$, filtered, and concentrated under reduced pressure to afford Compound BD4-8 (600.00 mg, crude) as a yellow oil and it was used into the next step without further purification.

$Boc_2O$ (589.28 mg, 2.70 mmol) was added to a solution of Compound BD4-8 (600.00 mg, 1.35 mmol) and TEA (409.82 mg, 4.05 mmol) in DCM (5.00 mL). The mixture was stirred at 15° C. for 12 hours. LCMS showed the reaction had completed. The mixture was concentrated to get the crude residue. The residue was purified by column chromatography ($SiO_2$, petroleum ether:ethyl acetate mixture with a ratio of 1:0 to 5:1) to afford Compound BD4-9 (230.00 mg, crude) as a yellow solid.

Compound B1 (47.30 mg, 186.25 μmol) and Pd(dppf)$Cl_2$ (11.36 mg, 15.52 μmol) to a solution of Compound BD4-9 (50.00 mg, 155.21 μmol) and KOAc (30.46 mg, 310.42 μmol) in dioxane (2.00 mL). The mixture was stirred at 90° C. for 12 hours under $N_2$. LCMS showed the reaction had completed. The mixture was concentrated to yield a crude residue. The residue was purified by prep-TLC ($SiO_2$, petroleum ether:ethyl acetate mixture with a ratio of 5:1) to afford Compound BD4 (30.00 mg, crude) as a yellow oil.

Synthesis of BD5

The following reaction schematic describes a synthesis pathway for Compound BD5.

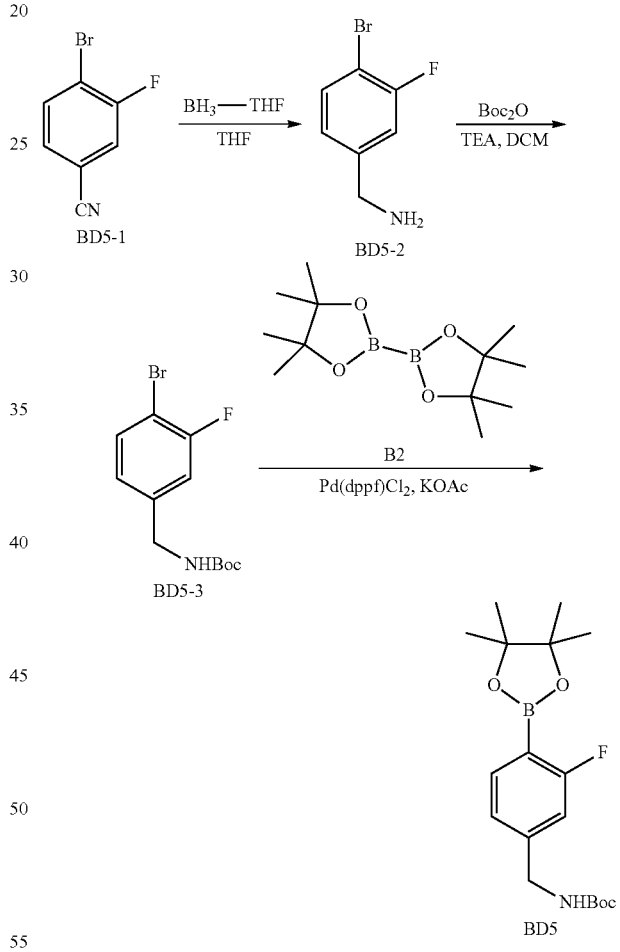

$BH_3$-THF (1 M, 75.00 mL) was added to a solution of 5.00 g Compound 51 (i.e. 1-bromo-3-fluorobenezonitrile) in THF (20.00 mL). The mixture was stirred at 80° C. for 1 hour. LCMS showed the reaction had completed. The reaction mixture was diluted by addition of MeOH (10 mL). The mixture was concentrated under reduced pressure to afford Compound BD5-2 (6.00 g, crude) as yellow oil which was used into the next step without further purification.

TEA (8.93 g, 88.23 mmol, 12.23 mL) and $Boc_2O$ (6.74 g, 30.88 mmol, 7.09 mL) was added to a solution of Compound BD5-2 (6.00 g, 29.41 mmol) in DCM (5.00 mL). The mixture was stirred at 15° C. for 1 hour. LCMS showed Compound BD5-2 had been consumed completely and one main peak in the MS with the desired m/z of Compound BD5-3 was detected. The reaction mixture was concentrated under reduced pressure to remove solvent. The residue was purified by column chromatography (SiO$_2$, petroleum ether: ethyl acetate mixture with a ratio of 50/1 to 30/1) to afford Compound BD5-3 (4.00 g, 8.62 mmol, 29.31% yield, 65.57% purity) as a white solid.

A mixture of KOAc (1.94 g, 19.74 mmol) and Pd(dppf)Cl$_2$ (481.47 mg, 658.00 µmol) and Compound B1 (1.67 g, 6.58 mmol) in dioxane (20.00 mL) was added to a solution of Compound BD5-3 (2.00 g, 6.58 mmol). The resulting mixture was degassed and purged with N$_2$ three times, and stirred at 90° C. for 12 hours under N$_2$ atmosphere. LCMS showed Compound BD5-3 had been consumed completely and one main peak in the MS with the desired m/z of Compound BD5 was detected. The reaction mixture was filtered and concentrated under reduced pressure to remove solvent. The residue was purified by column chromatography (SiO$_2$, petroleum ether:ethyl acetate mixture in a ratio of 50:1 to 20:1) to afford Compound BD5 (1.40 g, crude) as a light yellow oil.

Synthesis of BD6

The following reaction schematic describes a synthesis pathway for Compound BD6.

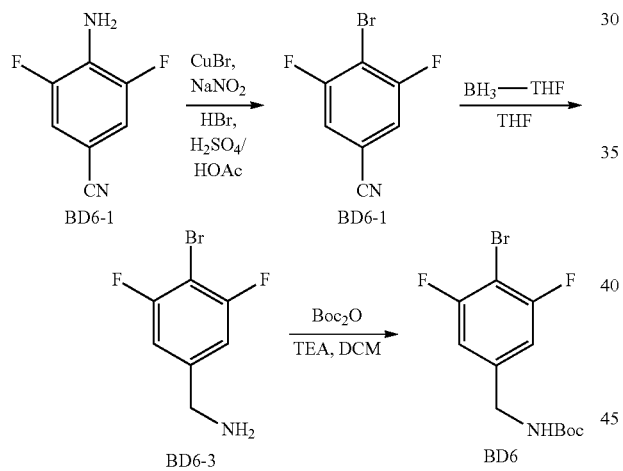

NaNO$_2$ (1.60 g, 23.20 mmol) was added portion wise at 5° C. to a solution of H$_2$SO$_4$ (12.50 mL, 98%), and the mixture was stirred at 15° C. for 0.5 hour. The mixture was cooled to 5° C. and AcOH (20.00 mL) was added dropwise. The mixture was stirred at 5° C. for 5 min. 3.25 g Compound BD6-1 (i.e., 4-amino-3,5-difluorobenzonitrile) was added portionwise and the mixture was stirred at 15° C. for 1 hour. The mixture was transferred into a dropping funnel and then added dropwise to a solution of CuBr (4.54 g, 31.64 mmol) in HBr (12.50 mL, 47%) over 0.5 hour. The mixture was then stirred at 15° C. for 12 hour. TLC showed the reaction had completed. The reaction mixture was diluted by addition H$_2$O (150 mL) and extracted with EtOAc (20 mL*3). The combined extracted organic layers were washed with brine (20 mL*3), dried over Na$_2$SO$_4$, filtered and concentrated under reduced pressure to yield a residue. The residue was purified by column chromatography (SiO$_2$, petroleum ether: ethyl acetate mixture in a ratio of 1:0 to 10:1) to afford Compound BD6-2 (2.30 g, crude) as a white solid.

BH$_3$-THF (1 M, 4.13 mL) was added to a solution of Compound BD6-2 (300.00 mg, 1.38 mmol) in THF (10.00 mL). The mixture was stirred at 15° C. for 0.5 hour. TLC showed the reaction had completed. The reaction mixture was diluted by addition MeOH (10 mL) and concentrated under reduced pressure to afford Compound BD6-3 (300.00 mg, crude) as colorless oil was used into the next step without further purification.

TEA (409.82 mg, 4.05 mmol) and Boc$_2$O (589.28 mg, 2.70 mmol) were added to a solution of Compound BD6-3 (300.00 mg, 1.35 mmol) in DCM (5.00 mL). The mixture was stirred at 15° C. for 12 hours. LCMS showed the reaction had completed. The mixture was concentrated to get crude residue. The residue was purified by prep-TLC (SiO$_2$, petroleum ether:ethyl acetate mixture with a ratio of 5:1) to yield Compound BD6 (100.00 mg, crude) as a yellow solid.

Synthesis of BD7

The following reaction schematic describes a synthesis pathway for compound BD7.

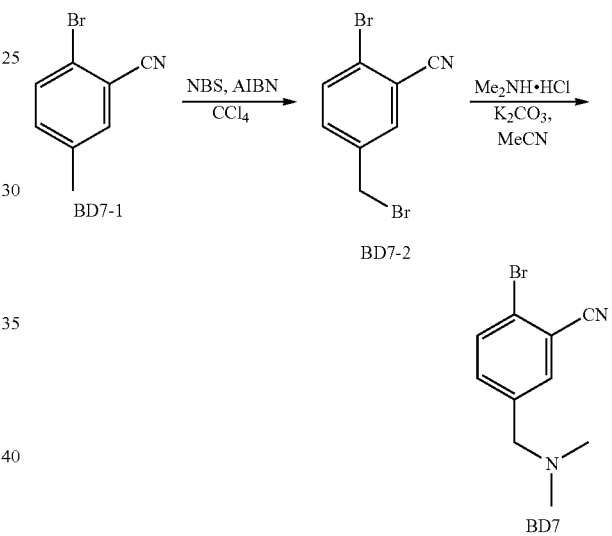

To a solution of 2.00 g Compound BD7-1 (i.e. 2-bromo-5-methylbenzonitrile) in CCl$_4$ (40.00 mL) was added AIBN (83.75 mg, 510.00 µmol) and NBS (2.00 g, 11.22 mmol). The mixture was stirred at 70° C. for 12 hours. TLC showed the reaction was complete. The reaction was filtered and concentrated to give a residue. The residue was purified by column chromatography (SiO$_2$, petroleum ether:ethyl acetate mixture in a ratio of 30:1 to 10:1) to afford Compound BD7-2 (1.50 g, crude) as a light yellow solid.

Dimethylamine hydrochloride (59.31 mg, 727.44 µmol) was added to a solution of Compound BD7-2 (100.00 mg, 363.72 µmol) and K$_2$CO$_3$ (150.81 mg, 1.09 mmol) in MeCN (2.00 mL). The mixture was stirred at 15° C. for 1 hour. TLC showed the reaction had completed. The reaction mixture was diluted by addition of H$_2$O (10 mL) and extracted with EtOAc (10 mL*3). The combined organic layers were washed with brine (10 mL*2), dried over Na$_2$SO$_4$, filtered, and concentrated under reduced pressure to yield a residue. The residue was purified by prep-TLC (SiO$_2$, petroleum ether:ethyl acetate mixture with a ratio of 1:1) to afford Compound BD7 (40.00 mg, 68.59 µmol, 18.86% yield, 41% purity) as a white solid.

Synthesis of BD8

The following reaction schematic describes a synthesis pathway for compound BD8.

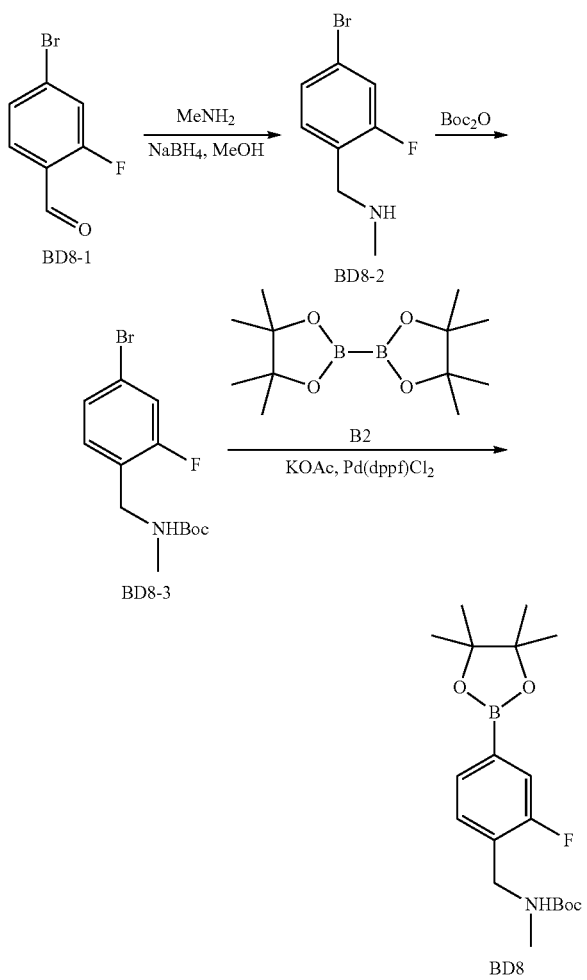

To a solution of 1.00 g Compound BD8-1 (i.e., 4-bromo-2-fluorobenzaldehyde) in MeOH (20.00 mL) was added to a solution 30% wt EtOH comprising MeNH₂ (1.53 g, 14.78 mmol). The mixture was stirred at 60° C. for 2 hours. NaBH₄ (372.69 mg, 9.85 mmol) was then added and the mixture was stirred at 15° C. for 1 hour. LCMS showed Compound MeNH₂ was consumed completely and one main peak in the MS with desired the m/z of Compound BD8-2 was measured. The reaction mixture was concentrated under reduced pressure to remove solvent. The residue was diluted with saturated NaHCO₃ (10 mL) and extracted with ethyl acetate (30 mL*3). The combined organic layers were washed with brine 50 mL dried over Na₂SO₄, filtered and concentrated under reduced pressure to give a residue to afford Compound BD8-2 (1.00 g, 4.39 mmol, 89.05% yield, 95.8% purity) as a yellow oil.

Boc₂O (2.00 g, 9.18 mmol, 2.11 mL) and DMAP (56.08 mg, 459.00 μmol) were added to a solution of Compound BD8-2 (1.00 g, 4.59 mmol) and TEA (1.39 g, 13.77 mmol, 1.91 mL) in DCM (10.00 mL). The mixture was stirred at 25° C. for 3 hours. LCMS showed Compound BD8-2 was consumed completely and one main peak with an m/z of Compound BD8-3 was detected. The reaction mixture was concentrated under reduced pressure to remove solvent. The residue was purified by column chromatography (SiO₂, petroleum ether:ethyl acetate mixture with a ratio of 100:1 to 4:1) to afford Compound BD8-3 (1.38 g, 3.14 mmol, 68.41% yield, 72.4% purity) as a yellow oil.

Compound B1 (87.79 mg, 345.72 μmol) and Pd(dppf)Cl₂ (23.00 mg, 31.43 μmol) was added to a solution of Compound BD8-3 (100.00 mg, 314.29 μmol) and KOAc (92.53 mg, 942.86 μmol) in dioxane (2.00 mL). The mixture was stirred at 90° C. for 12 hours under N₂. LCMS showed Compound BD8-3 was consumed completely and one main peak with a m/z corresponding to Compound BD8 was detected. The reaction mixture was concentrated under reduced pressure to remove solvent. The residue was purified by prep-TLC (SiO₂, petroleum ether:ethyl acetate mixture with a ratio of 4:1) to afford compound BD8 (100.00 mg, crude) as a yellow oil.

Synthesis of BD9

The following reaction schematic describes a synthesis pathway for compound BD9.

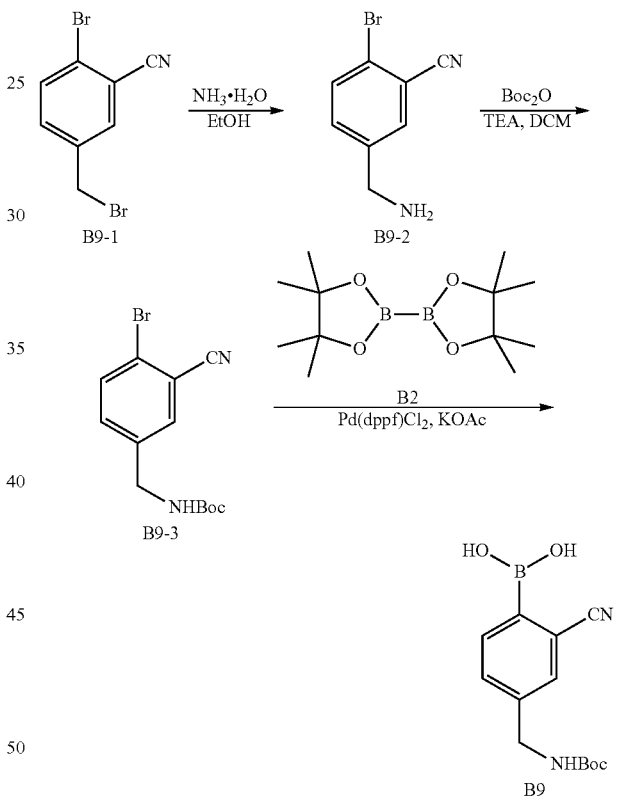

NH₃.H2O (18.20 g, 129.81 mmo) was added to a solution of 1.80 g Compound B9-1 (i.e. 2-bromo-5-(bromomethyl)benzonitrile) in EtOH (20.00 mL). The mixture was stirred at 15° C. for 1 hour. LCMS showed Compound B9-1 was consumed completely and one main peak in the mass spectra with m/z of Compound B9-2 was detected. The reaction was filtered and then concentrated under reduced pressure to remove solvent. Compound BD9-2 (700.00 mg, crude) was produced as a white solid and used in the next step without further purification.

TEA (1.01 g, 9.95 mmol) and Boc₂O (796.23 mg, 3.65 mmol) was added to a solution of Compound BD9-2 (700.00 mg, 3.32 mmol) in DCM (20.00 mL). The mixture was stirred at 15° C. for 12 hours. LCMS showed the reaction was complete. The reaction was concentrated to give a residue. The residue was purified by column chromatography (SiO$_2$, petroleum ether:ethyl acetate mixture with a ratio of 20:1 to 3:1) to afford Compound BD9-3 (1.00 g, crude) as light yellow oil.

A mixture of Compound BD9-3 (1.00 g, 3.21 mmol), Compound B2 (978.18 mg, 3.85 mmol), KOAc (472.54 mg, 4.81 mmol) and Pd(dppf)Cl$_2$ (234.88 mg, 321.00 μmol) in dioxane (20.00 mL) was degassed and purged with three times with N$_2$. The mixture was stirred at 90° C. for 12 hours under N$_2$ atmosphere. LCMS showed the formation of Compound BD9. The reaction was concentrated to give a residue. The residue was purified by column chromatography (SiO$_2$, Petroleum ether:Ethyl acetate mixture with a ratio of 1:1) to afford Compound BD9 (600.00 mg, crude) as a light yellow oil.

Synthesis of BD10

The following reaction schematic describes a synthesis pathway for compound BD10.

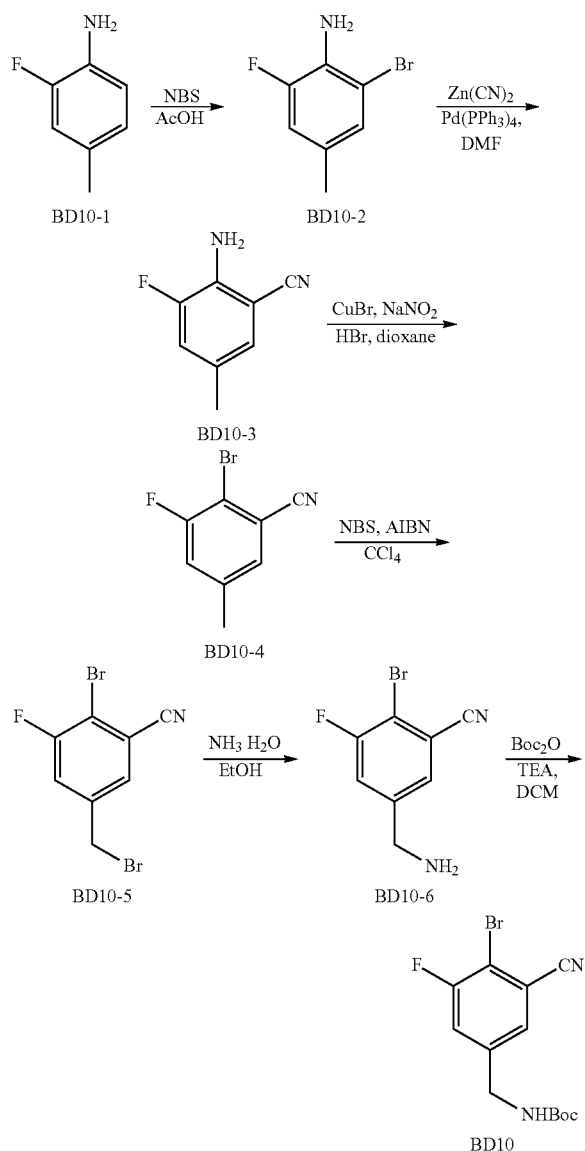

A stirred solution of 5.00 g Compound BD10-1 (i.e. 2-fluoro-4-methylaniline) in AcOH (20.00 mL) at 20° C. under argon was treated portion wise over 20 minutes with solid NBS (7.96 g, 44.75 mmol), then allowed to warm to 20° C. and stirred for 1 hour. LCMS showed the production of Compound BD10-2. The reaction mixture was treated with water (300 mL) and extracted with ethyl acetate (300 mL*3). The combined extracts were washed with water (300 mL*2) and then a 10% wt Na$_2$CO$_3$ solution (400 mL*2). The ethyl acetate extract was then dried over Na$_2$SO$_4$ and concentrated under vacuum to leave the Compound BD10-2 (8.00 g, crude) as a dark red oil which was used into the next step without further purification.

A mixture of Compound BD10-2 (2.30 g, 11.27 mmol), Zn(CN)$_2$ (2.05 g, 17.47 mmol) and Pd(PPh$_3$)$_4$ (1.43 g, 1.24 mmol) in DMF (30.00 mL) was degassed and purged with N$_2$ three times. The mixture was then stirred at 100° C. for 15 hours under N$_2$ atmosphere. TLC showed some desired product was formed. Water (50 mL) was added to the mixture and extracted with EtOAc (30 mL*3). The combined organic phase was washed with brine (50 mL*3), dried over Na$_2$SO$_4$, filtered and concentrated to give a residue. The residue was purified by column chromatography (SiO$_2$, petroleum ether:ethyl acetate mixture with a ratio of 20:1 to 5:1) to afford Compound BD10-3 (1.50 g, 9.99 mmol, 88.64% yield) as a white solid. NMR spectra of Compound BD10-3 were measured using CDCl$_3$ and a frequency of 400 mHz resulting in chemical shifts of δ(ppm)=7.06-6.91 (m, 2H), 4.32 (br s, 2H), 2.23 (br s, 3H).

Hydrobromic acid (12 mL, 48% wt, aqueous) was added to a solution of Compound BD10-3 (500.00 mg, 3.33 mmol) in dioxane (3.00 mL) and the solution was cooled to 0° C. before adding dropwise a solution of NaNO$_2$ (264.24 mg, 3.83 mmol) in water (2.00 mL) over 30 min. The temperature did not rise above 3° C. The resulting mixture was stirred at 2-3° C. for 2 h then poured onto a cooled (5° C.) solution of CuBr (716.53 mg, 5.00 mmol) in 48% wt hydrobromic acid (8 mL). The mixture was stirred for 10 min then heated to 50° C. over 1 h. LCMS showed the Compound BD10-3 was consumed completely. TLC showed a single compound eluting with a lower polarity than Compund BD10-3. The mixture was cooled to ambient temperature, basified (i.e., increased the pH) with saturated aqueous NaHCO$_3$ (50 mL) and extracted with diethyl ether (30 ml*3). The combined organic extracts were washed with brine (30 ml*3), dried over anhydrous Na$_2$SO$_4$, filtered and concentrated to give a residue. The residue was purified by prep-TLC (SiO$_2$, petroleum ether:ethyl acetate mixture with a ratio of 4:1) to afford Compound BD10-4 (200.00 mg, crude) as a white solid. NMR spectra of Compound BD10-4 were measured using CDCl$_3$ and a frequency of 400 mHz resulting in chemical shifts of δ(ppm)=ppm 7.25-7.21 (m, 1H), 7.14-7.07 (m, 1H), 2.31 (s, 3H).

AIBN (3.84 mg, 23.36 μmol) and NBS (91.47 mg, 513.94 μmol) were added to a solution of Compound BD10-4 (100.00 mg, 467.22 μmol) in CCl$_4$ (4.00 mL). The mixture was stirred at 70° C. for 12 hours. TLC showed the reaction was completed after 12 hours. The reaction was filtered and concentrated to give a residue. The residue was purified by prep-TLC (SiO$_2$, Petroleum ether:Ethyl acetate mixture in a ratio of 5:1) to afford Compound BD10-5 (50.00 mg, crude) as an off-white solid. NMR spectra of Compound BD10-3 were measured using CDCl$_3$ and a frequency of 400 mHz resulting in chemical shifts of δ(ppm)=7.44 (s, 1H), 7.33 (dd, J=2.0, 8.6 Hz, 1H), 4.33 (s, 2H).

A mixture of Compound BD10-5 (50.00 mg, 170.69 μmol) in EtOH (2.00 mL) and NH3.H2O (2.00 mL) (35%) was stirred at 15° C. for 0.5 hour. LCMS showed the production of BD10-5. The reaction mixture was filtered and concentrated to afford Compound BD10-6 (40.00 mg, crude) as a light yellow solid, which was used into the next step without further purification.

TEA (17.67 mg, 174.63 µmol) and Boc₂O (41.92 mg, 192.09 µmol) were added to a solution of Compound BD10-6 (40.00 mg, 174.63 µmol) in DCM (2.00 mL). The mixture was stirred at 15° C. for 1 hour. TLC indicated a clean reaction in that Compound BD10-6 was consumed completely and one new compound had been formed. The reaction mixture was concentrated to yield a residue. which was purified by prep-TLC (SiO₂, Petroleum ether:Ethyl acetate mixture with a ratio of 4:1) to afford Compound BD10 (20.00 mg, 48.61 µmol, 27.84% yield, 80% purity) as a white solid. NMR spectra of Compound BD10-4 were measured using CDCl₃ and a frequency of 400 mHz resulting in chemical shifts of δ(ppm)=7.34 (d, J=0.9 Hz, 1H), 7.23 (dd, J=1.8, 8.8 Hz, 1H), 4.95 (br s, 1H), 4.23 (br d, J=6.4 Hz, 2H), 1.43-1.32 (m, 9H).

Synthesis of BD11

The following reaction schematic describes a synthesis pathway for compound BD11.

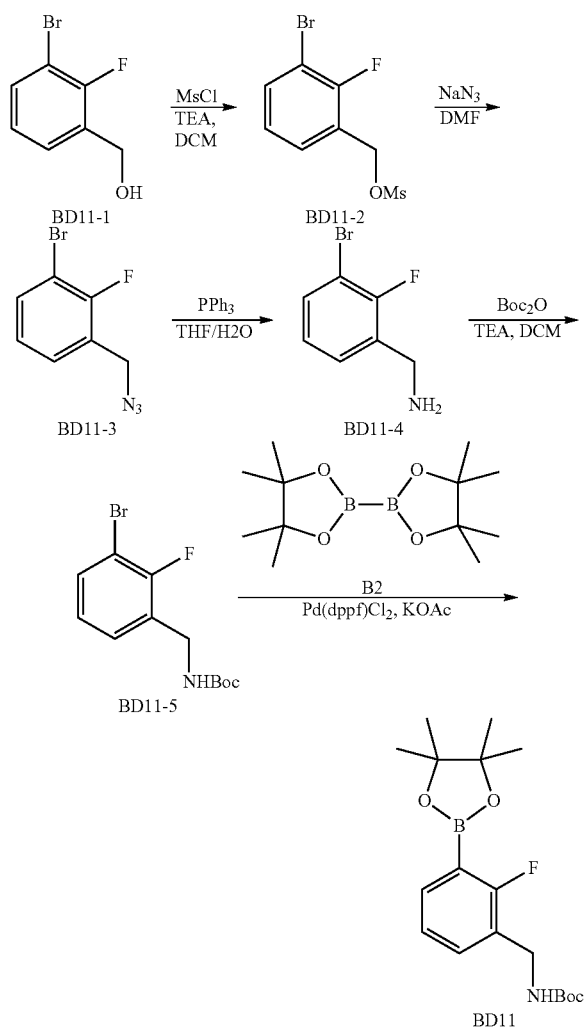

TEA (2.22 g, 21.95 mmol) and MsCl (1.26 g, 10.97 mmol) were added to a solution of 1.50 g Compound BD11-1 (i.e. 1-bromo-2-fluoro-3-(hydroxymethyl)benzene) in DCM (20.00 mL) at 0° C. The mixture was stirred at 15° C. for 1 hour. TLC produced one major new spot following stirring indicating the presence of a reaction product. The reaction was quenched with saturated NaHCO₃ (20 mL), extracted with DCM (20 mL*2), dried over anhydrous Na₂SO₄, filtered, and concentrated to afford Compound BD11-2 (2.00 g, crude) as a light yellow oil.

Sodium azide (550.76 mg, 8.47 mmol) was added to a solution of Compound BD11-2 (2.00 g, 7.06 mmol) in DMF (20.00 mL). The mixture was stirred at 15° C. for 12 hours. TLC showed the complete consumption of Compound BD11-2 and a new spot was formed on the TLC indicating the presence of a reaction product. Water (20 mL) was added and the reaction mixture was extracted with EtOAc (20 mL*3). The combined extracted organic layers were washed with brine (30 mL*3), dried over anhydrous Na₂SO₄, filtered, and concentrated to afford Compound BD11-3 (1.62 g, crude) as a yellow oil, which was used into the next step without further purification.

PPh₃ (2.22 g, 8.45 mmol) was added to a solution of Compound BD11-3 (1.62 g, 7.04 mmol) in a THF/H₂O mixture (3:1) (40.00 mL). The mixture was stirred at 50° C. for 12 hours under N₂. LCMS showed some the production of Compound BD11-4. The reaction was concentrated to afford Compound Compound BD11-4 (1.44 g, crude) as a light yellow oil, which was used into the next step without further purification TEA (2.11 g, 20.88 mmol) and Boc₂O (1.67 g, 7.66 mmol) were added to a solution of Compound BD11-4 (1.42 g, 6.96 mmol) in DCM (30.00 mL). The mixture was stirred at 15° C. for 12 hours. LCMS showed the production of BD11-5. The reaction was concentrated to give a residue. The residue was purified by column chromatography (SiO₂, petroleum ether:ethyl acetate mixture with a ratio of 30:1 to 10:1) to afford Compound BD11-5 (2.00 g, crude) as a white solid.

A mixture of Compound BD11-5 (240.00 mg, 789.08 µmol), Compound B2 (240.46 mg, 946.90 µmol), KOAc (116.16 mg, 1.18 mmol) and Pd(dppf)Cl₂ (57.74 mg, 78.91 µmol) in dioxane (5.00 mL) was degassed and purged three times with N₂. The mixture was stirred at 90° C. for 12 hours under N₂ atmosphere. LCMS indicated the presence of reaction products. The reaction was concentrated to give a residue. The residue was purified by prep-TLC (SiO₂, petroleum ether:ethyl acetate mixture with a ratio of 5:1) to afford Compound BD11 (160.00 mg, crude) as a light yellow solid.

Synthesis of BD12

The following reaction schematic describes a synthesis pathway for compound BD12.

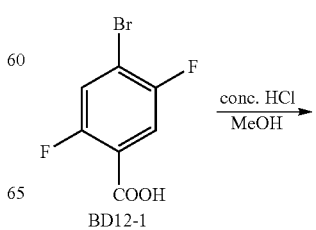

-continued

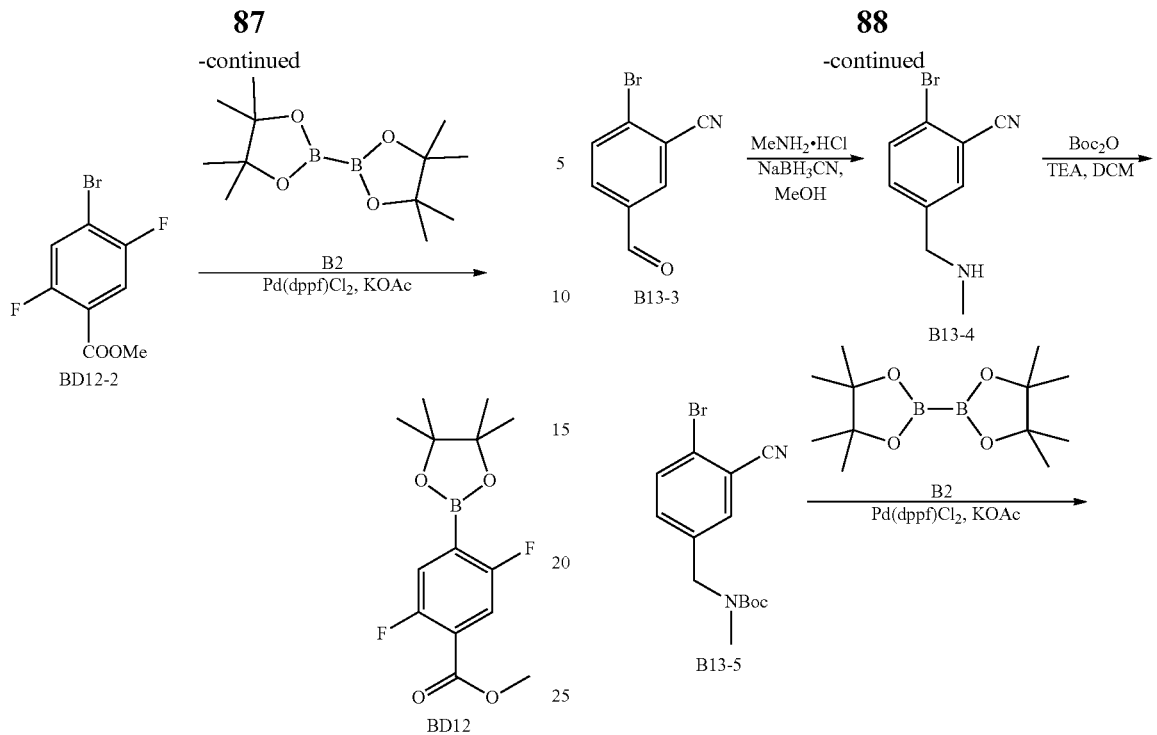

Concentrated HCl (8 mL) was added to a solution of 20.00 g Compound BD12-1 (i.e. 4-bromo-2,5-difluorobenzoic acid) in MeOH (800.00 mL). The mixture was stirred at 80° C. for 16 hours. TLC indicated Compound BD12-1 was consumed completely in the reaction resulting in the production of a new chromatogram spot with polarity lower than Compound BD12-1. The reaction mixture was concentrated in reduced pressure to afford Compound BD12-2 (19.35 g, crude) as a yellow solid.

A mixture of Compound BD12-2 (10.00 g, 39.84 mmol), Compound B2 (12.14 g, 47.80 mmol), KOAc (9.77 g, 99.59 mmol), and Pd(dppf)Cl$_2$ (1.46 g, 1.99 mmol) in dioxane (200.00 mL) was degassed and purged three times with N$_2$. The mixture was then stirred at 100° C. for 16 hours under N$_2$ atmosphere. TLC indicated Compound BD12-2 was consumed completely in the reaction and an additional new chromatogram spot was measured. The reaction mixture was concentrated at reduced pressure at 40° C. The residue was purified by column chromatography (SiO$_2$, petroleum ether: ethyl acetate mixture with a ratio of 1:0 to 20:1) to afford Compound BD12 (10.76 g, 32.49 mmol, 81.54% yield, 90% purity) as a white solid.

Synthesis of BD13

The following reaction schematic describes a synthesis pathway for compound BD13.

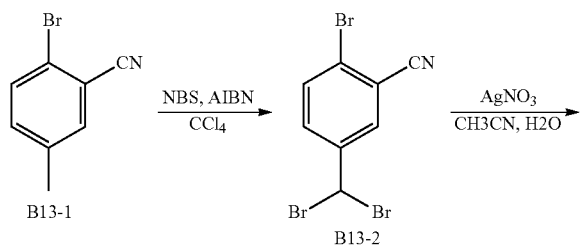

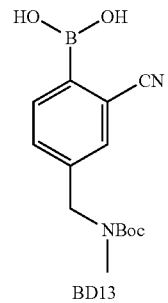

NBS (5.45 g, 30.60 mmol) and AIBN (334.99 mg, 2.04 mmol) were added to a solution of 2.00 g Compound BD13-1 (i.e. 2-bromo-5-methylbenzonitrile) in CCl$_4$ (60.00 mL). The mixture was stirred at 70° C. for 12 hours. TLC showed that after stirring 30% Compound B13-1 remained in the reaction mixture and a reaction product had formed. The mixture was concentrated to get a crude residue. The residue was purified by column chromatography (SiO$_2$, petroleum ether:ethyl acetate mixture with a ratio of 40:1 to 10:1). HNMR showed the product was a mixture of 30% starting material and 60% Compound B13-2 (2.20 g, crude) obtained as a white solid.

AgNO$_3$ (864.14 mg, 5.09 mmol) was added to a solution of Compound B13-2 (600.00 mg, 1.70 mmol) in CH$_3$CN (25.00 mL)/H$_2$O (10.00 mL). The mixture was stirred at 80° C. for 5 hours. TLC showed mostly desired product was formed. The mixture was concentrated to give a residue which was purified by column chromatography (SiO$_2$, petroleum ether:ethyl acetate mixture with a ratio of 20:1 to 5:1) to afford Compound BD13-3 (900.00 mg, crude) as a white solid.

The pH of a solution of methanamine hydrochloride (713.68 mg, 10.56 mmol) in MeOH (15.00 mL) was adjusted to 10 with the addition of TEA (713.05 mg, 7.04 mmol). Compound BD13-3 (740.00 mg, 3.52 mmol) was added to the solution. AcOH (21.14 mg, 352.00 μmol) was then added to the reaction mixture to adjust the pH of the solution to 5. The mixture was stirred at 15° C. for 1 hour. NaBH₃CN (1.11 g, 17.60 mmol, 5.00 eq) was added and the mixture was stirred at 15° C. for 12 hours. LCMS showed the production of BD13-4. The reaction was concentrated to give a residue which was dissolved in EtOAc (30 mL), washed with saturated aqueous NaHCO₃ (20 mL*3), dried over anhydrous Na₂SO₄, filtered, and concentrated to afford Compound BD13-4 (750.00 mg, crude) as yellow oil, which was used directly for the next step without further purification.

TEA (1.01 g, 10.00 mmol) and Boc₂O (799.97 mg, 3.67 mmol) were added to a solution of Compound BD13-4 (750.00 mg, 3.33 mmol) in DCM (20.00 mL). The mixture was stirred at 15° C. for 1 hour. TLC indicated the presence of reaction product. The reaction was concentrated to give a residue which was purified by column chromatography (SiO₂, petroleum ether:ethyl acetate mixture with a ratio of 20:1 to 10:1) to afford Compound BD13-5 (540.00 mg, crude) as light yellow oil.

A mixture of Compound BD13-5 (540.00 mg, 1.66 mmol), Compound B2 (632.31 mg, 2.49 mmol), KOAc (488.89 mg, 4.98 mmol) and Pd(dppf)Cl₂ (121.50 mg, 166.00 μmol) in dioxane (20.00 mL) was degassed and purged three times with N₂. The mixture was stirred at 90° C. for 8 hours under N₂ atmosphere. LCMS showed the reaction was completed and Compound BD13 has been produced. The reaction mixture was concentrated to give a residue which was purified by column chromatography (SiO₂, petroleum ether:ethyl acetate mixture with a ratio of 20:1 to 3:1) to afford Compound BD13 (320.00 mg, crude) as a light yellow oil.

Synthesis of Compound 10

The following reaction schematic describes a synthesis pathway for compound 10. The reaction of Intermediate 2 and substituted benzene derivative BD12 produces Compound 10-1, which is used to produce compound 10-2, which is used to produce Compound 10-3, which is used to produce the final product.

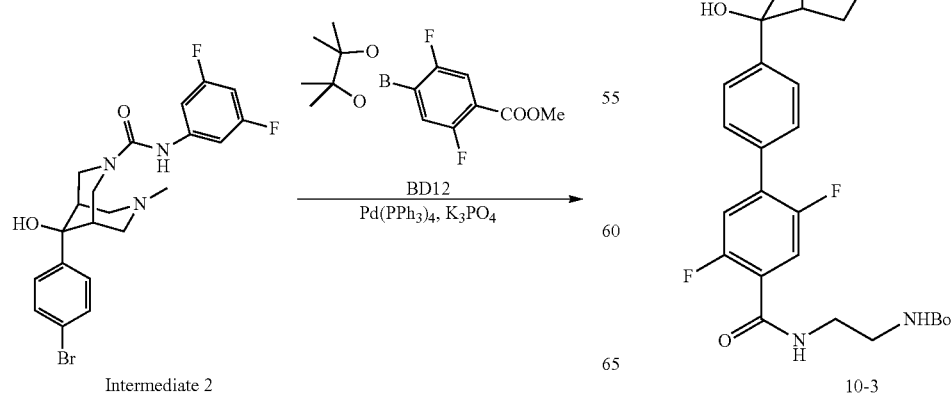

Intermediate 2

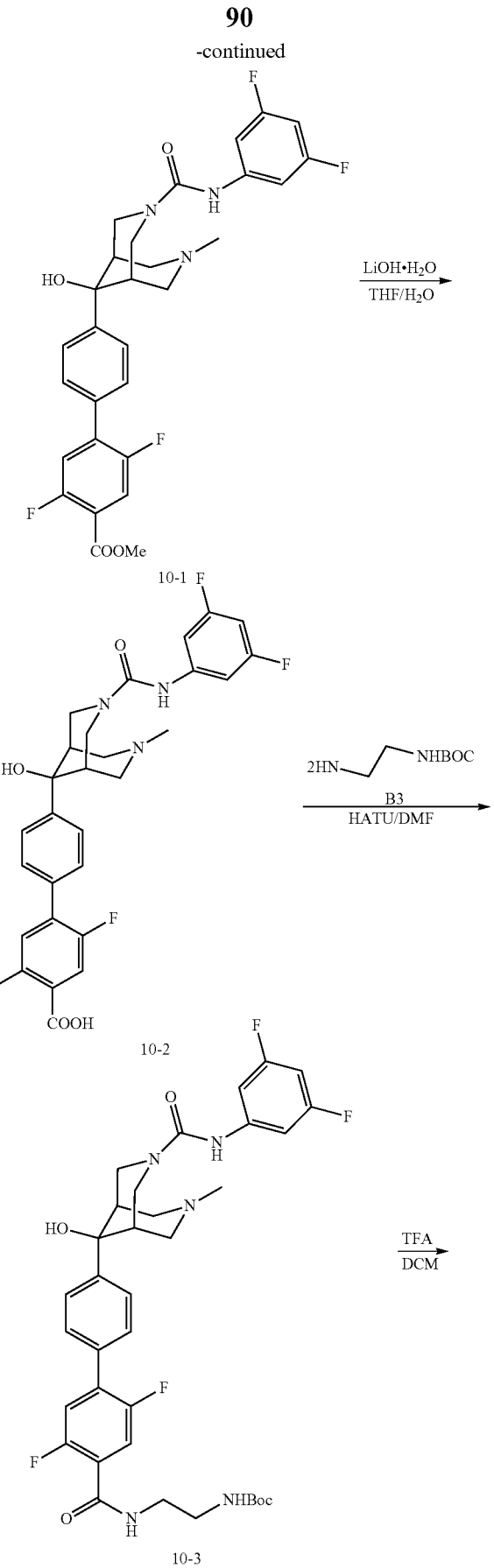

-continued

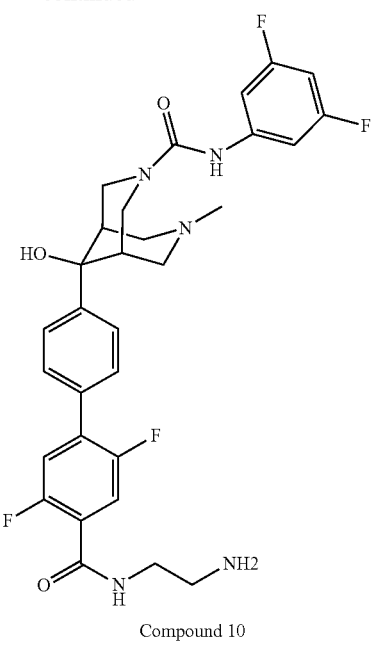
Compound 10

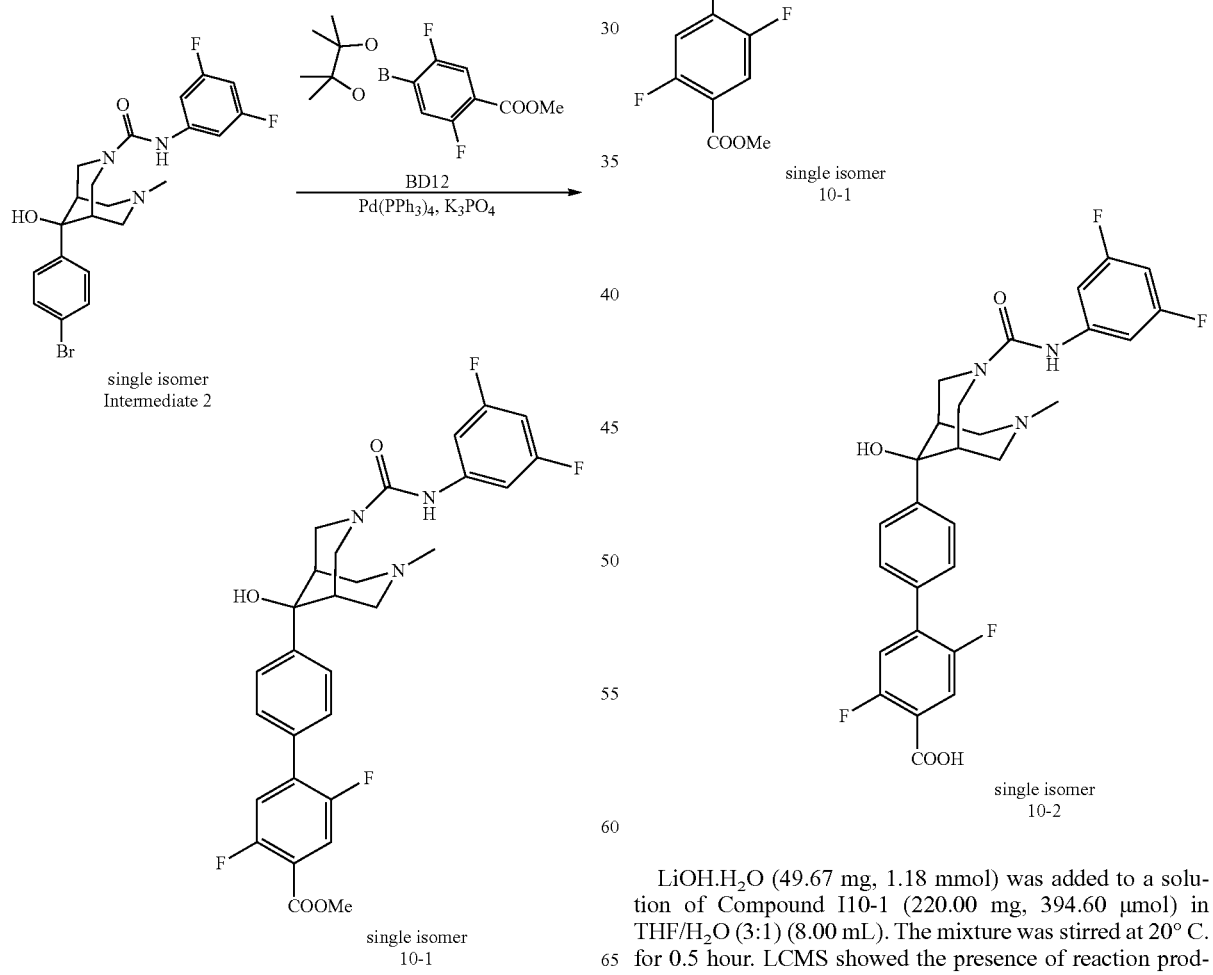

A mixture of Intermediate 2 (200.00 mg, 428.89 μmol), Compound BD12 (153.42 mg, 514.67 μmol), K₃PO₄ (136.56 mg, 643.34 μmol) and Pd(PPh₃)₄ (49.56 mg, 42.89 μmol) in dioxane (6.00 mL) was degassed and purged three times with N₂. The mixture was then stirred at 90° C. for 12 hours under N₂ atmosphere. LCMS indicated the presence of reaction product. The reaction was concentrated to give a residue which was purified by prep-TLC (SiO₂, ethyl acetate) to afford Compound I10-1 (220.00 mg, crude) as yellow oil.

Compound 10-2

LiOH.H₂O (49.67 mg, 1.18 mmol) was added to a solution of Compound I10-1 (220.00 mg, 394.60 μmol) in THF/H₂O (3:1) (8.00 mL). The mixture was stirred at 20° C. for 0.5 hour. LCMS showed the presence of reaction product. The reaction mixture was concentrated to give a residue which was dissolved in H₂O (3 mL) and adjusted to a pH of 5 with 1M HCl. The mixture was extracted with EtOAc (3 mL*3), the combined organic phase extract was dried over anhydrous Na$_2$SO$_4$, filtered and concentrated to afford Compound I10-2 (200.00 mg, crude) as a yellow solid. This was used in the next step without further purification.

Compound 10-3

Compound 10

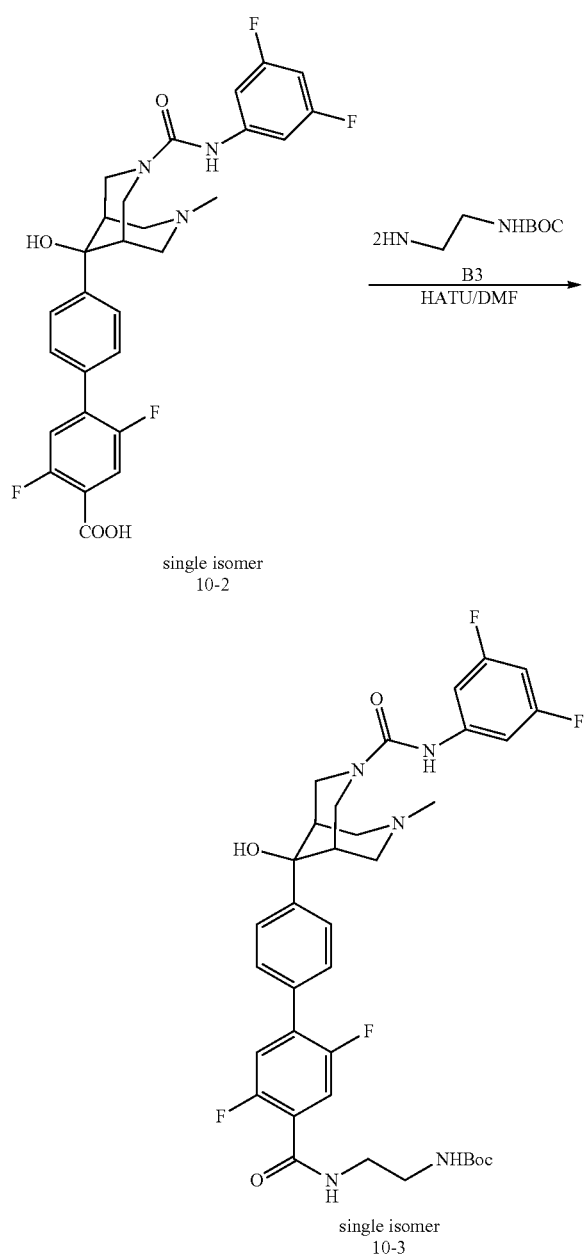

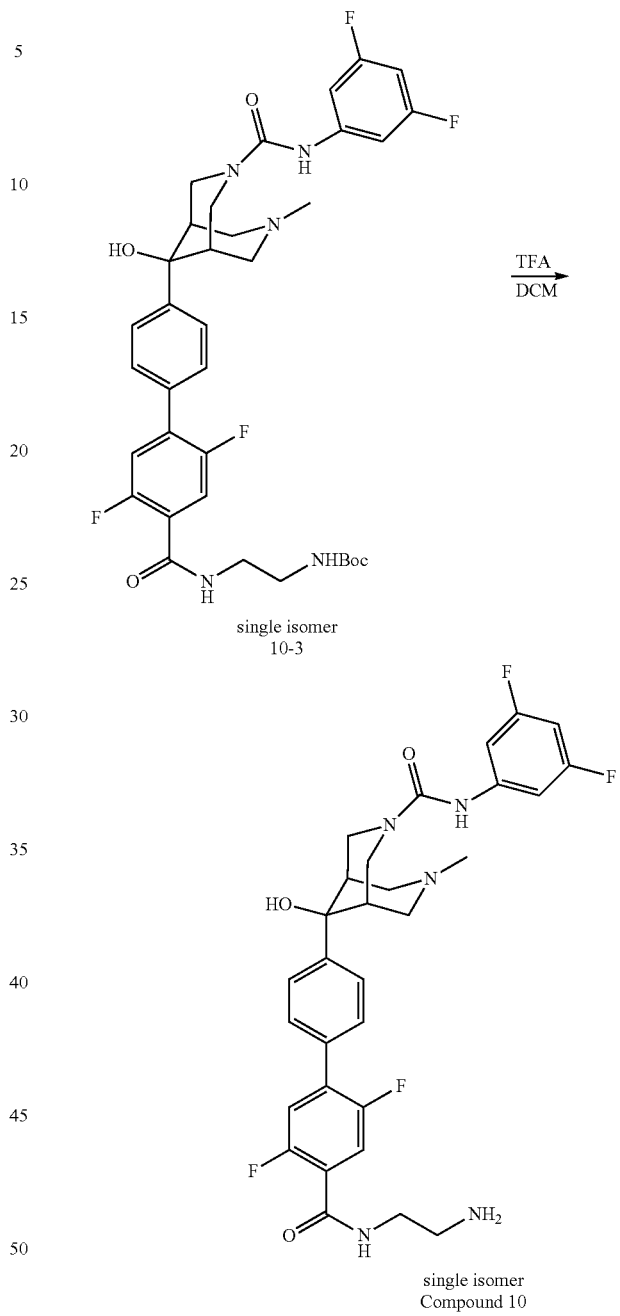

HATU (125.92 mg, 331.19 μmol), TEA (67.02 mg, 662.37 μmol) and Compound B3 (42.45 mg, 264.95 μmol) was added to a solution of Compound I10-2 (120.00 mg, 220.79 μmol) in DMF (6.00 mL). The mixture was stirred at 40° C. for 12 hours. LCMS showed that Compound I10-2 was consumed completely. The reaction was concentrated to give a residue which was purified by prep-TLC (SiO$_2$, ethyl acetate) to afford Compound I10-3 (70.00 mg, crude) as a light yellow oil.

TFA (500.00 μL) was added to a solution of Compound I10-3 (70.00 mg, 102.08 μmol) in DCM (2.00 mL). The mixture was stirred at 20° C. for 15 min. LCMS showed the reaction was complete. The mixture was concentrated to give a residue which was then purified by prep-HPLC (TFA condition) to afford Compound I10 (26.90 mg, 38.45 μmol, 37.67% yield, TFA) as a white solid. NMR spectra of were measured using MeOD and a frequency of 400 mHz resulting in chemical shifts of δ(ppm)=7.81-7.68 (m, 5H), 7.48 (dd, J=6.1, 11.2 Hz, 1H), 7.22 (br d, J=7.4 Hz, 2H), 6.61 (br t, J=9.2 Hz, 1H), 4.14 (br d, J=12.1 Hz, 2H), 3.91 (br d, J=12.1 Hz, 2H), 3.80 (br d, J=13.3 Hz, 2H), 3.71 (t, J=5.9 Hz, 2H), 3.24-3.15 (m, 4H), 3.06 (br s, 2H), 2.71 (s, 3H).

Synthesis of Compound 24
The following reaction schematic describes a synthesis pathway for compound 24. The reaction of Intermediate 4 and substituted benzene derivative BD9 produces Compound 24-1, which is used to produce the final product.
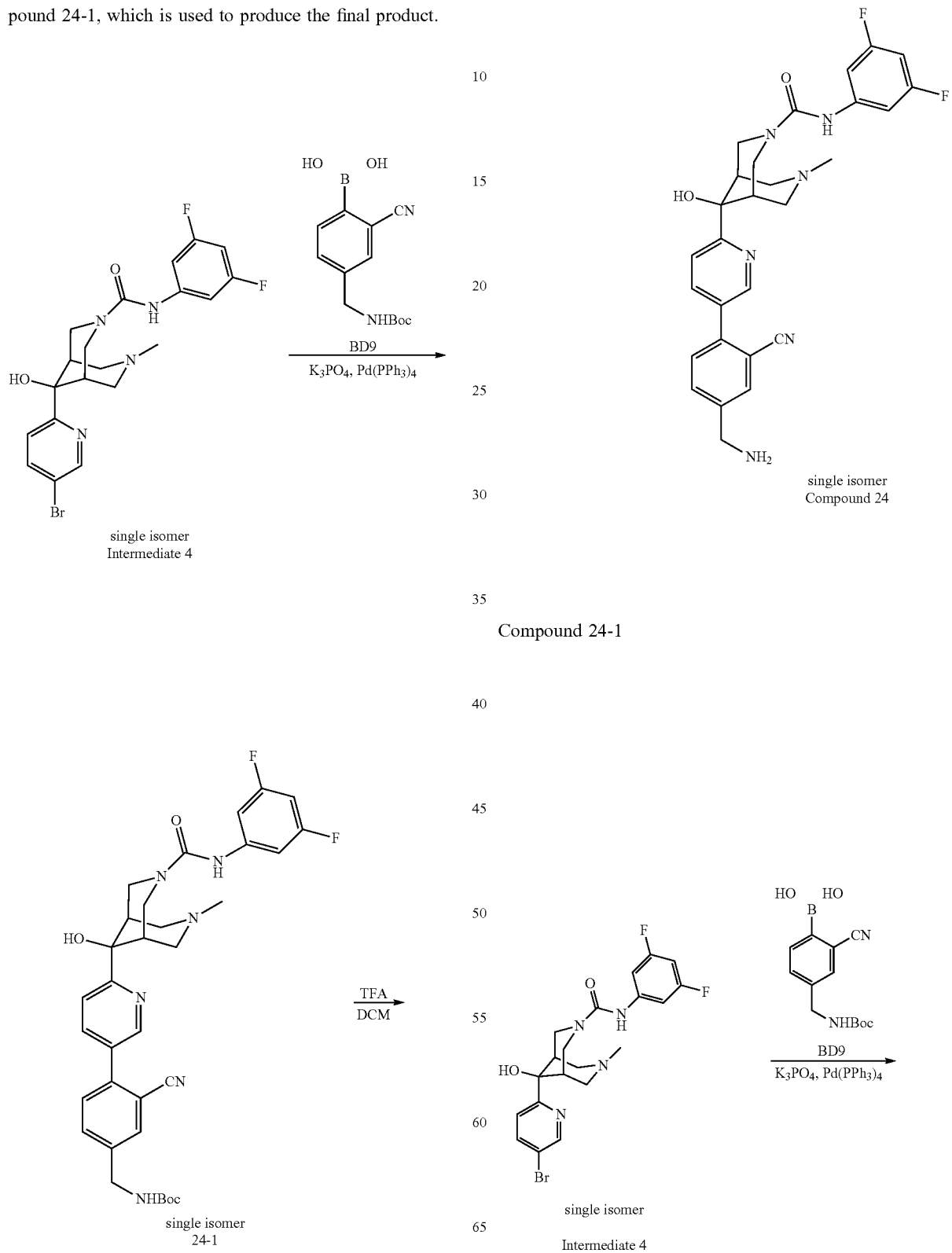

-continued

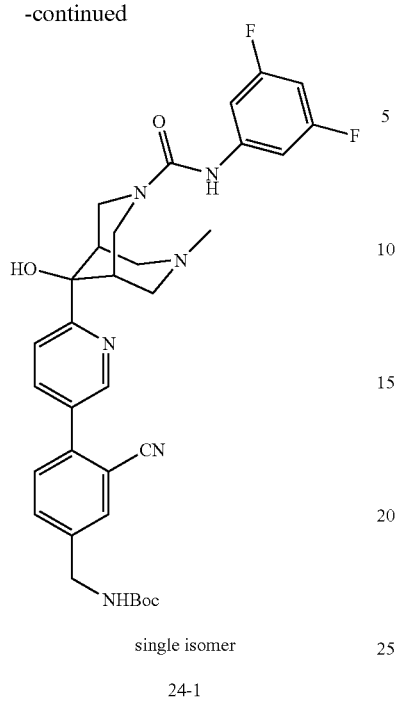

single isomer
24-1

Compound BD9 (519.93 mg, 1.88 mmol) and Pd(PPh$_3$)$_4$ (197.82 mg, 171.19 µmol) were added to a solution of Intermediate 4 (800.00 mg, 1.71 mmol) and K$_3$PO$_4$ (1.09 g, 5.14 mmol) in dioxane (4.00 mL). The mixture was stirred at 90° C. for 12 hours under N$_2$ atmosphere. LCMS showed the reaction was completed following stirring. The mixture was concentrated to get a crude residue which was purified by column chromatography (SiO$_2$, petroleum ether:ethyl acetate mixture with a ratio of 3:1 to 0:1) to afford Compound 24-1 (500.00 mg, crude) which was obtained as a yellow solid.
Compound 24

24-1

-continued

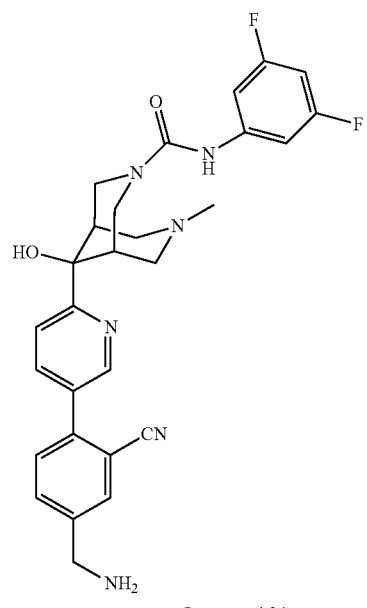

Compound 24

A solution of Compound 24-1 (500.00 mg, 808.19 µmol) in TFA (3.00 mL) and DCM (3.00 mL) was stirred at 15° C. for 5 min. LCMS showed the reaction was completed following stirring. The mixture was concentrated to obtain a crude residue which was purified by prep-HPLC (TFA condition) to afford Compound 24 (458.72 mg, 693.83 µmol, 85.85% yield, 95.68% purity, TFA) as a white solid. NMR spectra of were measured using methanol-d$_4$ and a frequency of 400 mHz resulting in chemical shifts of δ(ppm)=8.85 (dd, J=0.7, 2.4 Hz, 1H), 8.18 (dd, J=2.4, 8.4 Hz, 1H), 8.01 (d, J=1.5 Hz, 1H), 7.94-7.87 (m, 2H), 7.77 (d, J=8.2 Hz, 1H), 7.20 (d, J=9.2 Hz, 2H), 6.62-6.56 (m, 1H), 4.26 (s, 2H), 4.11 (d, J=11.2 Hz, 2H), 3.90 (br d, J=12.6 Hz, 2H), 3.78 (br d, J=13.2 Hz, 2H), 3.46 (br d, J=13.2 Hz, 2H), 3.02 (br s, 2H), 2.72 (s, 3H).

Example 2

1H NMR spectra and ESI measurements were performed on synthesized compounds 1-24. Table 4 lists the NMR chemical shifts for each measured compound. ESI was also measured for each compound in [M+H] modes. m/z of the ionized parent molecules of compounds 1-24 in the ESI measurements is also indicated in Table 4.

TABLE 4

| Compound | NMR Chemical Shifts (δ(ppm)) | ESI peak (m/z) |
|---|---|---|
| 1 | ¹H NMR (400 MHz, METHANOL-d₄) δ = 7.80-7.69 (m, 4H), 7.41 (s, 2H), 7.20 (br d, J = 7.5 Hz, 2H), 6.62 (br d, J = 8.8 Hz, 1H), 4.27 (s, 2H), 4.16 (br d, J = 11.4 Hz, 2H), 3.92 (br d, J = 12.3 Hz, 2H), 3.60 (br d, J = 14.0 Hz, 2H), 3.25-3.24 (m, 1H), 3.22 (br d, J = 14.0 Hz, 1H), 3.01 (br s, 2H) | 515.1 |
| 2 | ¹H NMR (400 MHz, METHANOL-d₄) δ = ppm 7.72-7.78 (m, 4 H) 7.39-7.45 (m, 2 H) 7.22 (br d, J = 7.50 Hz, 2 H) 6.58-6.64 (m, 1 H) 4.29 (s, 2 H) 4.12-4.16 (m, 2 H) 3.93 (br d, J = 13.45 Hz, 2 H) 3.79 (br d, J = 13.23 Hz, 2 H) 3.30 (d, J = 0.66 Hz, 2 H) 3.07 (br s, 2 H) 2.72 (s, 3 H) | 529.2 |
| 3 | ¹H NMR (400 MHz, METHANOL-d₄) δ = 7.74 (s, 4H), 7.62 (t, J = 6.8 Hz, 1H), 7.53 (t, J = 7.0 Hz, 1H), 7.42-7.35 (m, 1H), 7.22 (br d, J = 7.5 Hz, 2H), 6.60 (br t, J = 9.2 Hz, 1H), 4.27 (s, 2H), 4.14 (br d, J = 11.8 Hz, 2H), 3.91 (br d, J = 12.3 Hz, 2H), 3.80 (br d, J = 13.6 Hz, 2H), 3.22 (br d, J = 13.6 Hz, 2H), 3.06 (br s, 2H), 2.71 (s, 3H) | 511.2 |
| 4 |  | 512.2 |
| 5 | ¹H NMR (400 MHz, METHANOL-d₄) δ = 7.73 (s, 4H), 7.38-7.18 (m, 4H), 6.60 (br d, J = 9.0 Hz, 1H), 4.13 (br d, J = 12.6 Hz, 2H), 3.92 (br d, J = 12.3 Hz, 2H), 3.78 (br d, J = 13.2 Hz, 2H), 3.23 (br s, 4H), 3.06 (br s, 4H), 2.71 (s, 3H) | 543.2 |
| 6 | ¹H NMR (400 MHz, METHANOL-d₄) δ = ppm 7.70-7.79 (m, 1 H) 7.62-7.69 (m, 1 H) 7.55 (br d, J = 8.16 Hz, 1 H) 7.44-7.50 (m, 1 H) 7.34-7.42 (m, 2 H) 7.20 (br d, J = 9.48 Hz, 1 H) 7.11 (br d, J = 9.92 Hz, 1 H) 6.55-6.65 (m, 1 H) 4.09-4.26 (m, 4 H) 3.87-4.01 (m, 2 H) 3.68 (br d, J = 13.67 Hz, 1 H) 3.70 (br s, 1 H) 3.43-3.59 (m, 2 H) 3.15 (br s, 2 H) | 515.1 |
| 7 | ¹H NMR (400 MHz, METHANOL-d₄) ¹H NMR (400 MHz, METHANOL-d₄) δ = 8.00-7.96 (m, 1H), 7.89-7.70 (m, 3H), 7.59-7.44 (m, 2H), 7.24-7.07 (m, 2H), 6.64-6.53 (m, 1H), 4.28-4.23 (m, 2H), 4.17-3.86 (m, 4H), 3.74-3.43 (m, 3H), 3.16 (br s, 2H), 3.27 (br s, 1H) | 522.2 |
| 8 |  | 522.2 |
| 9 |  | 587.2 |
| 10 | ¹H NMR (400 MHz, METHANOL-d₄) δ = 7.81-7.68 (m, 5H), 7.48 (dd, J = 6.1, 11.2 Hz, 1H), 7.22 (br d, J = 7.4 Hz, 2H), 6.61 (br t, J = 9.2 Hz, 1H), 4.14 (br d, J = 12.1 Hz, 2H), 3.91 (br d, J = 12.1 Hz, 2H), 3.80 (br d, J = 13.3 Hz, 2H), 3.71 (t, J = 5.9 Hz, 2H), 3.24-3.15 (m, 4H), 3.06 (br s, 2H), 2.71 (s, 3H) | 586.2 |
| 11 | ¹H NMR (400 MHz, METHANOL-d₄) δ = 7.75 (d, J = 8.4 Hz, 2H), 7.59 (br d, J = 7.9 Hz, 2H), 7.25-7.17 (m, 4H), 6.61-6.56 (m, 1H), 4.94-4.89 (m, 1H), 4.19-4.13 (m, 4H), 3.91 (br d, J = 12.6 Hz, 2H), 3.62 (s, 1H), 3.64-3.58 (m, 1H), 3.60-3.57 (m, 1H), 3.24 (br d, J = 14.3 Hz, 2H), 3.01 (br s, 2H) | 515.1 |
| 12 | ¹H NMR (400 MHz, METHANOL-d₄) δ = 7.73 (s, 4H), 7.62 (t, J = 8.0 Hz, 1H), 7.43-7.34 (m, 2H), 7.23 (br d, J = 7.7 Hz, 2H), 6.58 (br t, J = 9.0 Hz, 1H), 4.23-4.09 (m, 4H), 3.95-3.79 (m, 4H), 3.21 (br d, J = 13.5 Hz, 2H), 3.06 (br s, 2H), 2.71 (s, 2H), 2.64-2.61 (m, 1H) | 511.2 |
| 13 | ¹H NMR (400 MHz, METHANOL-d₄) δ = 8.87 (s, 1H), 8.17 (d, J = 7.6 Hz, 1H), 7.89 (d, J = 8.2 Hz, 1H), 7.72 (t, J = 7.9 Hz, 1H), 7.51-7.41 (m, 2H), 7.28-7.21 (m, 2H), 6.63 (tt, J = 2.3, 9.1 Hz, 1H), 4.24 (s, 2H), 4.16 (br d, J = 11.8 Hz, 2H), 3.93 (br d, J = 11.9 Hz, 2H), 3.82 (br d, J = 12.9 Hz, 2H), 3.48 (br d, J = 13.4 Hz, 2H), 3.37 (br s, 1H), 3.06 (br s, 2H), 2.76 (s, 3H) | 512.2 |
| 14 |  | 526.2 |
| 15 |  | 525.2 |
| 16 | ¹H NMR (400 MHz, METHANOL-d₄) δ = ppm 8.94 (d, J = 2.21 Hz, 1 H) 8.20-8.25 (m, 1 H) 7.84 (d, J = 8.60 Hz, 1 H) 7.64-7.70 (m, 3 H) 7.20 (br d, J = 9.70 Hz, 2 H) 6.56-6.65 (m, 1 H) 4.33 (s, 2 H) 4.10 (d, J = 10.58 Hz, 2 H) 3.89 (br | 526.2 |

TABLE 4-continued

| Compound | NMR Chemical Shifts (δ(ppm)) | ESI peak (m/z) |
|---|---|---|
| | d, J = 12.35 Hz, 2 H) 3.75 (br d, J = 13.23 Hz, 2 H) 3.46 (br s, 2 H) 3.01 (s, 2 H) 2.77 (s, 3 H) 2.71 (s, 3 H) | |
| 17 | $^1$H NMR (400 MHz, METHANOL-$d_4$) δ = 8.91-8.81 (m, 1H), 8.19 (td, J = 1.2, 8.2 Hz, 1H), 8.05 (s, 1H), 7.93 (d, J = 8.4 Hz, 2H), 7.79 (d, J = 7.9 Hz, 1H), 7.25-7.16 (m, 2H), 6.62-6.54 (m, 1H), 4.34 (s, 2H), 4.14 (br d, J = 11.9 Hz, 2H), 3.94-3.76 (m, 4H), 3.46 (br d, J = 13.2 Hz, 2H), 3.31 (br d, J = 1.3 Hz, 2H), 2.79 (s, 3H), 2.73 (s, 3H) | 533.2 |
| 18 | $^1$H NMR (400 MHz, METHANOL-$d_4$) δ = ppm 8.05 (s, 1 H) 7.91 (br d, J = 8.16 Hz, 1 H) 7.73-7.84 (m, 5 H) 7.22 (br d, J = 9.26 Hz, 2 H) 6.61 (br t, J = 9.15 Hz, 1 H) 4.45 (s, 2 H) 4.15 (br d, J = 12.35 Hz, 2 H) 3.93 (br d, J = 12.35 Hz, 2 H) 3.81 (br d, J = 13.01 Hz, 2H) 3.23 (br d, J = 13.23 Hz, 2 H) 2.93 (s, 6 H) 2.73 (s, 3 H) | 546.2 |
| 19 | $^1$H NMR (400 MHz, METHANOL-$d_4$) δ = 8.95 (d, J = 2.0 Hz, 1H), 8.23 (dd, J = 2.3, 8.2 Hz, 1H), 7.85 (d, J = 8.6 Hz, 1H), 7.68-7.64 (m, 2H), 7.70-7.62 (m, 1H), 7.21 (br d, J = 7.8 Hz, 2H), 6.61 (br t, J = 9.2 Hz, 1H), 4.26 (s, 2H), 4.11 (br d, J = 11.7 Hz, 2H), 3.91 (br d, J = 12.1 Hz, 2H), 3.72 (br s, 2H), 3.17 (s, 2H), 3.03 (br s, 2H), 2.69 (s, 3H) | 512.2 |
| 20 | $^1$H NMR (400 MHz, METHANOL-$d_4$) δ = 7.84-7.79 (m, 2H), 7.74-7.68 (m, 2H), 7.62-7.54 (m, 3H), 7.20 (dd, J = 2.1, 9.4 Hz, 2H), 6.63-6.55 (m, 1H), 4.23 (s, 2H), 4.12 (br d, J = 12.1 Hz, 2H), 3.90 (br d, J = 11.5 Hz, 2H), 3.77 (br d, J = 13.0 Hz, 2H), 3.18 (br d, J = 13.5 Hz, 2H), 3.04 (br s, 2H), 2.68 (s, 3H) | 511.2 |
| 21 | | 523.1 |
| 22 | | 522.2 |
| 23 | $^1$H NMR (400 MHz, METHANOL-$d_4$) δ = 7.97 (d, J = 1.8 Hz, 1H), 7.84 (dd, J = 2.0, 8.2 Hz, 1H), 7.81-7.68 (m, 5H), 7.20 (dd, J = 2.2, 9.7 Hz, 2H), 6.58 (tt, J = 2.3, 9.1 Hz, 1H), 4.24 (s, 2H), 4.14 (d, J = 11.5 Hz, 2H), 3.90 (br d, J = 12.3 Hz, 2H), 3.80 (br d, J = 13.0 Hz, 2H), 3.20 (br d, J = 13.5 Hz, 2H), 3.06 (br s, 2H), 2.70 (s, 3H) | 518.2 |
| 24 | $^1$H NMR (400 MHz, METHANOL-$d_4$) δ = 8.85 (dd, J = 0.7, 2.4 Hz, 1H), 8.18 (dd, J = 2.4, 8.4 Hz, 1H), 8.01 (d, J = 1.5 Hz, 1H), 7.94-7.87 (m, 2H), $^1$H NMR (400 MHz, METHANOL-$d_4$) 7.77 (d, J = 8.2 Hz, 1H), 7.20 (d, J = 9.2 Hz, 2H), 6.62-6.56 (m, 1H), 4.26 (s, 2H), 4.11 (d, J = 11.2 Hz, 2H), 3.90 (br d, J = 12.6 Hz, 2H), 3.78 (br d, J = 13.2 Hz, 2H), 3.46 (br d, J = 13.2 Hz, 2H), 3.02 (br s, 2H), 2.72 (s, 3H) | 519.2 |

Example 3

The activity profiles of compounds 17, 23, and 24 were assessed by various in vitro measurements. The minimum inhibitory concentration (MIC), MIC in the presence of normal human serum (NHS), microsome $CL_{int}$, the % of free compounds following a plasma protein biding (PPB) assay, and the concentration of drug where the human-ether-à-go-go-related gene (hERG gene) channel block is halved ($IC_{50}$ (hERG)) were measured using standard in vitro protocols for compounds 17, 23, and 24. Unless otherwise indicated, measurements (e.g., microsomal clearance) were performed using a standard microsomal stability assay using LC/MS/MS techniques.

Microsomal Stability Assay

Test compounds were incubated at 37° C. with liver microsomes pooled from multiple donors at 1 μM in the presence of a NADPH regenerating system at 0.5 mg/ml microsomal protein. Positive of testosterone (a 3A4 substrate), propafenone (a 2D6 substrate), and diclofenac (a 2c9 substrate) were similarly incubated with microsomes in the presence of a NADPH regenerating system. Samples are removed at 0, 5, 10, 20, 30, and 60 minutes of incubation and immediately mixed with cold acetonitrile containing an internal standard (IS). Samples are then analyzed by LC/MS/MS to determine the disappearance of the test compound and are assessed based on the peak area ratios of analyte/IS (no standard curve).

MIC Assays

The MIC tests were based on broth microdilution method in CLSI-M7.

On the day of testing, test compounds were dissolved in pure DMSO (Sigma 276855-2 L) to 6.4 mg/ml as stock. Solutions of varying concentrations of DMSO were prepared in wells of a v-bottom 96-well plate (Axygen-WIPP02280). A multi-pipette was used to perform serial dilutions as necessary. From well to well, the drug concentrations were 6.4, 3.2, 1.6, 0.8, 0.4, 0.2, 0.1, 0.05, 0.025, 0.0125, 0.00625 and 0 mg/ml in DMSO. For extremely potent antibiotic, the starting concentrations were adjusted accordingly. This was the drug mother plate.

Daughter plates were prepared by placing 98 μl of a testing medium into each well of a u-bottom 96-well plate (Costar 3788). An aliquot of each 2 μl solution from each well of the mother plate was then transferred into the corresponding wells of the daughter plate using a multi-pipette work station (CyBi®-SELMA). Testing media were selected based on CLSI-M7, M11 and M45. Cation adjusted Mueller Hinton Broth (CA-MHB-212322) was the testing medium for majority of bacterial species. Brucella medium (BD-211088) supplemented with 5% LHB, 0.5% hemin and 0.1% vitamin K1 (Sigma-95271) was the testing medium for anaerobic bacteria.

One day prior to the day of MIC test, bacterial strains were streaked out from −80° C. glycerol stock onto Trypticase Soy Agar (TSA) plates (Brucella blood agar for anaerobic bacteria) and incubated at 37° C. for 20 hours (in anaerobic condition for anaerobic bacteria, e.g., 80% $N_2$, 10% $H_2$ and 10% $CO_2$). Single colonies of bacteria were picked by using an inoculation loop (Greiner-731175) and suspended into 5 ml sterile saline. The turbidity of the suspension was adjusted to 0.10 (Siemens MicroS can turbidity meter), which implies a concentration of colony forming units ("CFU") of approximately $1.0 \times 10^8$ CFU/ml. The bacterial suspension was diluted 100× in testing media.

For MIC experiments with NHS, testing medium and human serum (Equitech Bio Inc. BRH-949908) were mixed in the ratio of 1:1. This was used for inoculation of the daughter plates. An aliquot of 100 μl of the bacterial suspension was inoculated into each well of the daughter plates using a multi-pipette. Following preparation, each well comprised approximately $5.0 \times 10^5$ CFU/ml bacteria, 1% DMSO, and serially diluted compounds at final concentrations of 64, 32, 16, 8, 4, 2, 1, 0.5, 0.25, 0.125, 0.0625, and 200 μl testing media.

The plates were incubated in ambient atmosphere and at 37° C. in an incubator for 20 hours (for anaerobic bacteria in an anaerobic condition as described above for 48 hours). The MIC values were determined and based on the standards of CLSI methods M7-A7, broth microdilution method. MIC is the lowest compound concentration that completely or significantly inhibits the growth of bacteria in the testing medium. Test compounds were compared to control antibiotics Penicillin G (Sigma-13752) and levofloxacin (Sigma-28266).

$IC_{50}$ measurements for hERG Potassium Ion Channel

Blockade of the cardiac ion channel coded by the hERG gene can lead to cardiac arrhythmia. Many small compounds have been found to bind to the hERG gene leading to problems in the QT response. To determine the viability of inventive compounds as pharmacological agents that would not affect the hERG channel blockade, a standard automated planar clamp method was employed to determine the $IC_{50}$ for various test compounds on their inhibition of the channel. An electrophysiological assay was prepared to measure the electric current passing through the hERG channel expressed in a stable CHO cell line by applying the planar clamp method. This assay was performed using the automated QPatch platform (Sophion, Denmark) which allows fast and accurate electrophysiological characterization of the hERG ion channel and the determination of $IC_{50}$ values for the test compounds.

Table 5 shows the results of the in vitro activity profile measurements for these compounds as measured with *Escherichia coli* ATC-25922.

TABLE 5

|  | Compound 17 | Compound 23 | Compound 24 |
|---|---|---|---|
| MIC (μg/ml) | 4.0 | 2.0 | 2.0 |
| MIC (50% NHS) (μg/ml) | 0.5 | 0.5 | 0.25 |
| human $CL_{int}$ (μg/ml/min) | 138 | 93 | 144 |
| mouse $CL_{int}$ (μg/ml/min) | >145 | 105 | >145 |
| PPB - % free | 45 | 27 | 38 |
| hERG:$IC_{50}$ (μM) | >30 | >30 | >30 |

As can be seen in Table 5, compounds of the invention show significant activity against *Escherichia coli* ATCC 25922. Additionally, the compounds of the invention do not provide a significant block to the hERG ion channel blockade, and the similarity in intrinsic clearance values between human and mouse microsomes indicates the compounds may have a similar pharmacokinetic profile in those species.

The MIC in the presence of added serum (50% NHS) of selected inventive compounds were screened against several bacterial strains recited in Table 6. Additionally, the MIC's of another gyrase inhibitor ("GSK") with a structure different from the inventive compounds and the antibacterial levofloxin was measured. MIC are given in μg/mL.

TABLE 6

| Bacterial Species | Strain Code | Compound 17 | Compound 23 | Compound 24 | GSK | Levofloxin (0.2 μg/mL) |
|---|---|---|---|---|---|---|
| *Klebsiella pneumonia* | ATCC-43816 | 1.78 | 2 | 4 | 1 | 0.13 |
| *Klebsiella pneumonia* | ATCC-700603 | 7.12 | 8 | 16 | 4 | 0.5 |
| *Escherichia coli* | ATCC-25922 | 0.22 | 0.5 | 1 | 0.5 | 0.031 |
| *Escherichia coli* | CCUG-59353 | 1.78 | 2 | 4 | 2 | >2 |
| *Escherichia coli* | NCTC-13476 | 1.78 | 2 | 4 | 2 | >2 |
| *Escherichia coli* | ATCC-BAA-2340 | 0.22 | 0.25 | 0.25 | 0.25 | >2 |
| *Acinetobacter baumannii* | ATCC 17978 | 28.5 | 64 | 64 | 8 | 1 |
| *Pseudomonas aeruginosa* | ATCC-BAA-47 (PAO1) | 1.78 | 2 | 2 | 2 | 1 |
| *Enterobacter aerogenes* | ATCC-13048 | 0.45 | 1 | 2 | 0.5 | 0.13 |

TABLE 6-continued

| Bacterial Species | Strain Code | Compound 17 | Compound 23 | Compound 24 | GSK | Levofloxin (0.2 µg/mL) |
|---|---|---|---|---|---|---|
| Enterobacter cloacae | ATCC-222 | 0.45 | 0.5 | 0.5 | 0.25 | 0.06 |
| Enterobacter cloacae | ATCC-BAA-1143 | 3.56 | 2 | 2 | 1 | 0.06 |
| Citrobacter werkmanii Brenner | ATCC-51114 | 3.56 | 4 | 4 | 2 | 0.25 |
| Serratia marcescens Bizio | ATCC-29021 | 3.56 | 4 | 16 | 1 | 0.13 |
| Proteus mirabilis | ATCC-29906 | 7.12 | 4 | 32 | 2 | 0.25 |
| Enterococcus faecalis | ATCC-29212 | 0.45 | 0.5 | 1 | 0.5 | 2 |
| Enterococcus faecium | ATCC-700221 | 0.89 | 1 | 4 | 2 | >2 |
| Staphylococcus aureus | ATCC-29213 | ≤0.11 | 0.13 | 0.25 | 0.06 | 0.5 |
| Staphylococcus aureus | NRS-384 | 0.22 | 0.13 | 0.5 | 0.06 | 1 |
| Staphylococcus aureus | NRS-100 | 0.22 | 0.13 | 0.25 | 0.06 | 0.5 |
| Staphylococcus aureus | WX1-009 | ≤0.11 | ≤0.06 | 0.25 | ≤0.02 | >2 |

As can be seen the inventive compounds show significant activity against a variety of bacterial strains. For example, each tested compound showed MIC's similar to or greater than the control compounds for bacterial strains tested.

Example 4

The in vivo activity of compounds 17 ("WXL-6440"), 23 ("WXL-6360"), and 24 ("WXL-6361") was measured using a standard pharmacokinetic study to determine the in vivo half life ($T_{1/2}$) of compounds. The in vivo activity was also measured to determine the number of colony forming units ("CFU") formed in the presence of antibiotic composition comprising various compounds.

Pharmacokinetic Study

Compounds were tested in a pharmacokinetic ("PK") study to determine the $T_{1/2}$ of test compounds in mice. The PK study was performed at an approved contract research organization. Each test compound was dissolved in a vehicle to make a test antibiotic composition. The vehicle may be, for example, a water or a 5% solutol in saline solution Administration to each mouse is performed via intravenous (IV) cannulation of the tail vein. Blood is collected over K2-EDTA anticoagulant from the submandibular or sapheneous vein at predetermined time points. Following collection, the blood samples are stored at −70° C. until analysis by LC-MS and comparison to a standard calibration curve results in the $T_{1/2}$ for each compound. The blood concentration of test compounds was measured at various times following 10 mg/kg (mouse) intravenous (IV) administration of each tested compound. FIG. 1 shows the concentrations of compound 17 in the blood of mice at various times following administration. As can be seen following comparison to the standard calibration curve, Compound 17 has a 34 hour $T_{1/2}$ after IV administration. The $T_{1/2}$ for compound 17 was 34.2 hours, for compound 23 was 22.0 hours, and for compound 24 was 22.5 hours. Correspondingly, the in vivo clearance for compound 17 is 8.86 mL/min/kg, for compound 23 is 9.78 mL/min/kg, and for compound 24 is 13.9 mL/min/kg. As can be seen, the in vivo studies indicate these compounds have a long half life and a low clearance.

Colony Forming Units

The in vivo activity to determine the CFU following administration of the test compounds was determined on a deep thigh infection caused by Escherichia coli ATCC 25922 in mice. The in vivo efficacy of various compounds was measured using a modified version of the deep-thigh infection model disclosed in Selbie, F R, et al., Br. J. Exp. Pathol. 33 (1952), 315-26 and Zuluaga, A F, et al., BMC Infect. Dis. 6 (2005) 55, each of which is hereby incorporated by reference. The efficacy was determined measuring the number of bacterial colony forming units ("CFU") of mice injected with Escherichia coli ATCC 29522 on Day 0 following administration of the compounds.

Female CD-1 mice, aged 6-8-weeks, were purchased from local licensed supplier. The mice were allowed to acclimate for 3 days in the animal facility before experimentation began. The mice were then rendered neutropenic by intraperitoneal ("I.P.") injection of 150 mg/kg cyclophosphamide on Day-4 (4 days prior to the injection of bacteria), and a maintaining dose of 100 mg/kg cyclophosphamide on Day-1 (1 day prior to the injection of bacteria). This regimen conditioned mice to neutropenia during the study. On the day of bacterial challenge (Day 0), Escherichia coli ATCC 29522 was injected into each mouse. Prior to injection, the bacterium was streaked out from −80° C. glycerol stock onto a tryptone soya agar ("TSA") plate on Day-1. On the day of bacterial challenging (Day 0), single colonies on the agar plate were suspended in sterile saline and the final bacterial concentration was adjusted to approximately $1\times10^6$ CFU/ml based on turbidity readout of the bacterial solution from a Siemens MicroScan turbidity meter. The bacterial suspension was kept on ice temporarily prior to injection once the desired concentration was achieved.

On Day 0, 100 µl of bacterial suspension as prepared above was injected into the posterior quadriceps muscles of the right thigh. Antibiotic compositions comprising a tested compound in a vehicle were given to mice through tail vein injection at one hours, three hours, five hours and 7 hours post of infection ("P.I."). The vehicle for each antibiotic composition is 5% (w/v) solutol HS15 in water. At 24 h P.I., all mice were euthanized. Infected thigh muscles for each tested mouse were excised and stored in ice-cold sterile saline for transfer to a Biosafety Level 2 ("BSL-2") laboratory for subsequent CFU counting. Within one hour following sample collection, the muscles from mice tested with the same antibiotic composition were homogenized by a homogenizer (IKA T10 basic S25), serially diluted in sterile saline, and plated on TSA plates. The plates were incubated at 30° C. for approximately 18 h. The CFU were counted and calculated as CFU/mouse. The animal facility was AAALAC accredited, and the animal welfare in this experiment was in compliance of IACUC.

Figure 2:
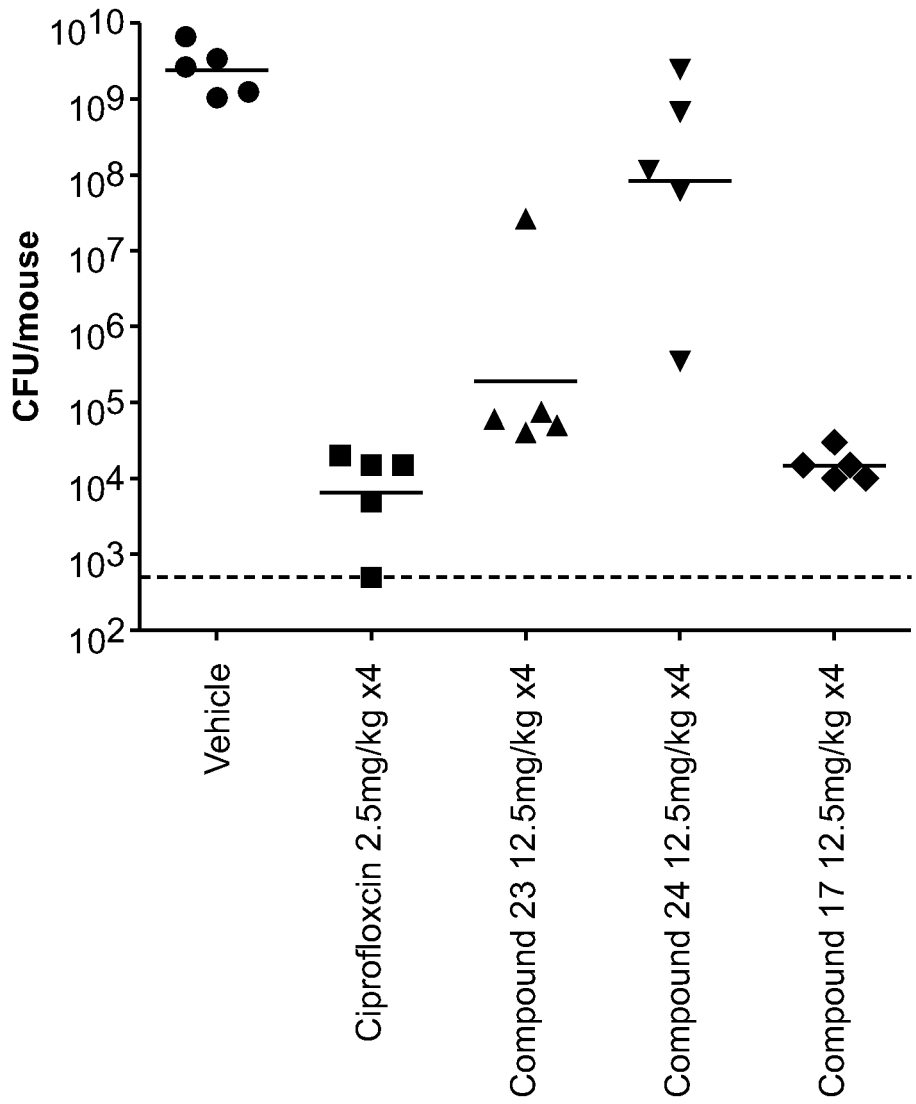
FIG. 2 is a plot of the number of colony forming units (CFU) of E. coli ATC-25922 in a mouse model of infection. The mice were treated with either vehicle (negative control), or four doses of the specified agent at the specified concentration.

The number of colony forming units was independently measured in five different mice per composition administered. Each mouse was administered a mass of active compound per kg weight of the mouse four times a day. Mice were administered a composition without a test compound, compositions comprising 2.5 mg(ciprofloxacin)/kg, 12.5 mg(Compound 17)/kg, 12.5 mg(Compound 23)/kg, and 12.5 mg(Compound 24)/kg). FIG. 2 shows number of colony forming units in each mouse per active given. As can be seen, antibiotics composing compounds 17, 23, or 24 decrease the amount of colony forming units of *Escherichia coli* ATCC 25933 as compared to the control. Comparable results to ciprofloxacin are found for Compounds 17 and 23.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound for treating bacterial infections having the structure of formula (I):

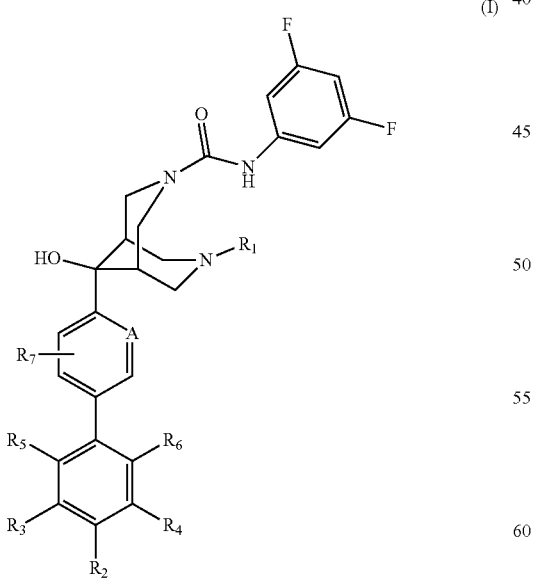

(I)

wherein A is N or $CR_7$;
$R_1$ is hydrogen or $C_{1-5}$ linear or branched alkyl;
$R_7$ is independently hydrogen, $C_{1-5}$ linear or branched alkyl, or F; and $R_2$-$R_6$ are independently selected at each occurrence from hydrogen, —X, -$L_1$-X, or -$L_1$-R;

where

—X is independently selected at each occurrence from —CN, —N(R)$_2$, or —F;

$L_1$ is selected independently at each occurrence from —NH—, —N(R)—, —C(O)—, —(CH$_2$)$_{1-4}$—, —C(O)—N(R)—, —(C(R)$_2$)$_{1-3}$—N(R)—, or —(C(R)$_2$)$_{1-3}$—;

R is independently selected at each occurrence from hydrogen, or $C_{1-5}$ linear or branched alkyl;

wherein at least one of $R_2$-$R_4$ is a group -$L_1$-R;

or a pharmaceutically acceptable salt thereof.

2. The compound according to claim 1, wherein R is independently selected at each occurrence from hydrogen, methyl, or ethyl.

3. The compound according to claim 1, wherein only one of $R_2$-$R_6$ is -$L_1$-R or -$L_1$-X.

4. The compound according to claim 1, wherein $R_1$ is hydrogen or methyl.

5. The compound according to claim 1, wherein $R_2$ is -$L_1$-R or -$L_1$-X.

6. The compound according to claim 1, wherein $R_3$ or $R_4$ is -$L_1$-R or -$L_1$-X.

7. The compound according to claim 1, wherein —X is —NH$_2$ or —N(R)$_2$.

8. The compound according to claim 1, wherein $R_3$-$R_6$ are independently selected at each occurrence from hydrogen, —CN, or —F.

9. The compound according to claim 1 having the structure

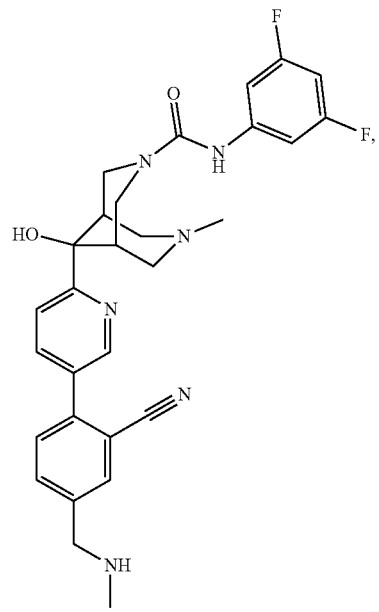

109
-continued
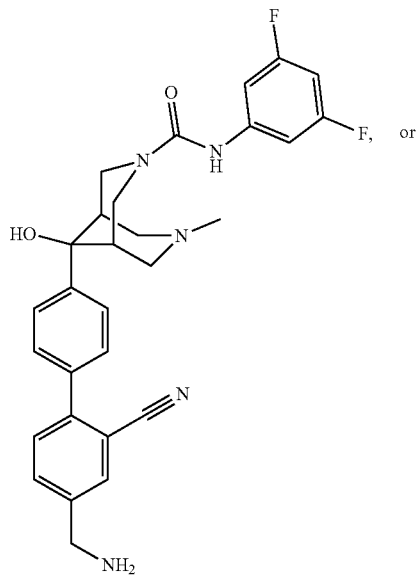
, or
110
-continued
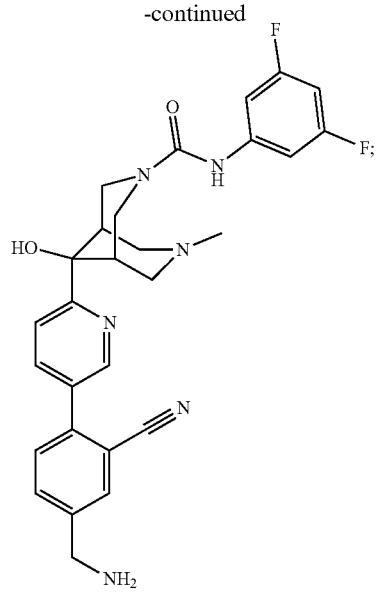
or a pharmaceutically acceptable salt thereof.
* * * * *